US011337994B2

(12) United States Patent
Ghandehari et al.

(10) Patent No.: US 11,337,994 B2
(45) Date of Patent: May 24, 2022

(54) IN SITU GELLING COMPOSITIONS FOR THE TREATMENT OR PREVENTION OF INFLAMMATION AND TISSUE DAMAGE

(71) Applicant: UNIVERSITY OF UTAH RESEARCH FOUNDATION, Salt Lake City, UT (US)

(72) Inventors: Hamidreza Ghandehari, Salt Lake City, UT (US); Siam Oottamasathien, Salt Lake City, UT (US); Mark Martin Jensen, Salt Lake City, UT (US); Joseph Cappello, Salt Lake City, UT (US); Wanjian Jia, Salt Lake City, UT (US); Glenn D. Prestwich, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 16/333,434

(22) PCT Filed: Sep. 14, 2017

(86) PCT No.: PCT/US2017/051538
§ 371 (c)(1),
(2) Date: Mar. 14, 2019

(87) PCT Pub. No.: WO2018/053111
PCT Pub. Date: Mar. 22, 2018

(65) Prior Publication Data
US 2019/0209606 A1  Jul. 11, 2019

Related U.S. Application Data

(60) Provisional application No. 62/458,618, filed on Feb. 14, 2017, provisional application No. 62/395,313, filed on Sep. 15, 2016.

(51) Int. Cl.
*A61K 31/737* (2006.01)
*A61K 31/728* (2006.01)
(Continued)

(52) U.S. Cl.
CPC .......... *A61K 31/737* (2013.01); *A61K 9/0019* (2013.01); *A61K 9/06* (2013.01);
(Continued)

(58) Field of Classification Search
None
See application file for complete search history.

(56) References Cited

U.S. PATENT DOCUMENTS 2,599,172 A   6/1952  Hadidian
4,240,163 A  12/1980  Galin
(Continued)

FOREIGN PATENT DOCUMENTS

DE     19813234      9/1999
DE    102005004643   8/2006
(Continued)

OTHER PUBLICATIONS

Tazawa et al., "Portal Vein Thrombus, Portal Hemodynamicsand Portal Vein Invasion: Radiation therapy in combination with transcatheter arterial chemoembolization for hepatocellular carcinoma with extensive portal vein involvement" Journal of Gastroenterology and Hepatology vol. 16 pp. 660-665 (Year: 2001).*
(Continued)

*Primary Examiner* — Eric Olson
(74) *Attorney, Agent, or Firm* — Michael Best & Friedrich LLP

(57) ABSTRACT

Described herein are in situ gelling compositions. The compositions include an anti-inflammatory polysaccharide and a gelling polymer, wherein the composition is a liquid prior to administration to a subject but converts to a gel upon
(Continued)

administration to the subject. The compositions described herein have numerous applications with respect to the local treatment (reduction or prevention) of inflammation and/or tissue damage.

14 Claims, 8 Drawing Sheets

Specification includes a Sequence Listing.

(51) Int. Cl.

| | | |
|---|---|---|
| *A61K 47/42* | (2017.01) | |
| *A61M 31/00* | (2006.01) | |
| *A61K 45/06* | (2006.01) | |
| *A61K 9/00* | (2006.01) | |
| *C07K 14/78* | (2006.01) | |
| *A61K 47/36* | (2006.01) | |
| *A61P 29/00* | (2006.01) | |
| *A61K 9/06* | (2006.01) | |

(52) U.S. Cl.
CPC ............ *A61K 31/728* (2013.01); *A61K 45/06* (2013.01); *A61K 47/36* (2013.01); *A61K 47/42* (2013.01); *A61M 31/002* (2013.01); *A61P 29/00* (2018.01); *C07K 14/78* (2013.01)

(56) References Cited

U.S. PATENT DOCUMENTS

| | | |
|---|---|---|
| 4,814,437 A | 3/1989 | De Belder |
| 4,851,521 A | 7/1989 | Della Valle |
| 5,008,253 A | 4/1991 | Casu |
| 5,166,331 A | 11/1992 | Della Valle |
| 5,442,053 A | 8/1995 | Della Valle |
| 5,559,104 A | 9/1996 | Romeo |
| 5,981,509 A | 11/1999 | Akima |
| 6,288,043 B1 | 9/2001 | Spiro |
| 6,339,074 B1 | 1/2002 | Cialdi |
| 6,803,037 B2 | 10/2004 | Abatangelo |
| 6,828,308 B2 | 12/2004 | Mastradonato |
| 6,833,363 B2 | 12/2004 | Renier |
| 7,202,230 B2 | 4/2007 | Rivarossa |
| 7,642,240 B2 * | 1/2010 | Cohen .................... A61K 47/61 514/1.1 |
| 7,683,036 B2 | 3/2010 | Bellin |
| 7,855,187 B1 | 12/2010 | Prestwich |
| 8,329,673 B2 | 12/2012 | Prestwich |
| 8,343,942 B2 | 1/2013 | Oottamasathien |
| 8,399,430 B2 | 3/2013 | Prestwich |
| 8,951,990 B2 | 2/2015 | Prestwich |
| 8,993,536 B2 | 3/2015 | Kakehi |
| 9,549,945 B2 | 1/2017 | Prestwich |
| 9,932,389 B2 | 4/2018 | Cappello et al. |
| 10,226,481 B2 | 3/2019 | Prestwich |
| 2001/0018445 A1 | 8/2001 | Huang et al. |
| 2002/0049183 A1 | 4/2002 | Yedgar |
| 2003/0176355 A1 | 9/2003 | Cappello et al. |
| 2003/0198599 A1 | 10/2003 | Yalpani |
| 2003/0199687 A1 | 10/2003 | Yalpani |
| 2004/0053885 A1 | 3/2004 | Venbrocks |
| 2005/0119219 A1 | 6/2005 | Bellini |
| 2005/0203056 A1 | 9/2005 | Ulmer |
| 2005/0227910 A1 | 10/2005 | Yang et al. |
| 2006/0009840 A1 | 1/2006 | Hossainy |
| 2006/0172967 A1 | 8/2006 | Toida |
| 2006/0223781 A1 | 10/2006 | Guo |
| 2007/0054878 A1 | 3/2007 | Venbrocks |
| 2008/0025950 A1 | 1/2008 | Prestwich |
| 2008/0032920 A1 | 2/2008 | Prestwich |
| 2008/0050335 A1 | 2/2008 | Faour |
| 2008/0182982 A1 | 7/2008 | Kumar |
| 2008/0306022 A1 | 12/2008 | Miyamoto |
| 2008/0306023 A1 | 12/2008 | Rinaudo |
| 2009/0105463 A1 | 4/2009 | Berry |
| 2009/0197807 A1 | 8/2009 | Callegaro |
| 2009/0202639 A1 | 8/2009 | Bellin |
| 2009/0226499 A1 | 9/2009 | Wisniewski |
| 2009/0246283 A1 | 10/2009 | Kumar |
| 2009/0252810 A1 | 10/2009 | Tommeraas |
| 2009/0285850 A1 | 11/2009 | Dillon |
| 2010/0143304 A1 | 6/2010 | Lowenstein |
| 2010/0204325 A1 | 8/2010 | Blanda |
| 2010/0278877 A1 | 11/2010 | Tamura |
| 2010/0317616 A1 | 12/2010 | Prestwich |
| 2011/0082104 A1 | 4/2011 | Prestwich |
| 2011/0129531 A1 | 6/2011 | Collette et al. |
| 2011/0287517 A1 | 11/2011 | Steward |
| 2012/0149032 A1 | 6/2012 | Davis |
| 2012/0282300 A1 | 11/2012 | Masters et al. |
| 2013/0011467 A1 | 1/2013 | Zhang et al. |
| 2013/0022545 A1 | 1/2013 | Lee et al. |
| 2013/0059772 A1 | 3/2013 | Kumar |
| 2013/0190234 A1 | 7/2013 | Prestwich |
| 2013/0195988 A1 | 8/2013 | Duan et al. |
| 2014/0086976 A1 | 3/2014 | Szalay |
| 2014/0194370 A1 | 7/2014 | Cappello et al. |
| 2014/0206022 A1 | 7/2014 | Nuti |
| 2014/0343011 A1 | 11/2014 | Prestwich et al. |
| 2015/0152165 A1 | 6/2015 | Ghandehari et al. |
| 2015/0209385 A1 | 7/2015 | Prestwich et al. |
| 2018/0353522 A1 | 12/2018 | Ghandehari et al. |

FOREIGN PATENT DOCUMENTS

| | | |
|---|---|---|
| EP | 0244178 | 11/1987 |
| EP | 0285357 | 10/1989 |
| EP | 0214879 | 11/1990 |
| EP | 0889055 | 4/2000 |
| EP | 0601055 | 6/2000 |
| EP | 0925310 | 8/2000 |
| EP | 0754460 | 6/2002 |
| EP | 1169387 | 3/2003 |
| EP | 1022289 | 7/2004 |
| EP | 1365777 | 4/2006 |
| EP | 1087797 | 7/2009 |
| EP | 1994062 | 7/2009 |
| EP | 1901786 | 12/2010 |
| EP | 1144459 | 2/2011 |
| FR | 2864090 | 6/2005 |
| JP | 11279042 | 10/1999 |
| JP | H11269077 | 10/1999 |
| JP | 2001097997 | 4/2001 |
| JP | 2001163789 | 6/2001 |
| WO | 1989007932 | 9/1989 |
| WO | 1999043728 | 9/1999 |
| WO | 2004004744 | 1/2004 |
| WO | 2005056608 | 6/2005 |
| WO | 2007006403 | 1/2007 |
| WO | 2007043050 | 4/2007 |
| WO | 2008008859 | 1/2008 |
| WO | 2005046562 | 12/2008 |
| WO | 2009013162 | 1/2009 |
| WO | 2009059748 | 9/2009 |
| WO | 2009124266 | 12/2009 |
| WO | 2009158704 | 12/2009 |
| WO | 2010121700 | 10/2010 |
| WO | 2010130466 | 11/2010 |
| WO | 2010130468 | 11/2010 |
| WO | 2011140024 | 11/2011 |
| WO | 2011156445 | 12/2011 |
| WO | 2013181471 | 12/2013 |
| WO | 2014031693 | 2/2014 |
| WO | 2018053111 | 3/2018 |

OTHER PUBLICATIONS

English Summary of Notice of Rejection from Japanese Patnet Office for Application 2014-501262 dated Jan. 15, 2016.
English translation of Israeli Office Action for Patent Application No. 228605 dated May 1, 2016.

(56) References Cited

OTHER PUBLICATIONS

English translation of Korean Office Action for KR 10-2013-7027636 dated Mar. 21, 2018.
English Translation of Office Action for Japanese Patent Application 2013-514324 dated Apr. 24, 2015.
English Translation of Office Action for Japanese Patent Application 2015-253460 dated Sep. 21, 2016.
European Office Action for 12761460.0 dated May 12, 2015.
European Search Report for Application No. 1179068.5 dated Jul. 10, 2013.
Extended European Search Report for European Application No. 12761460.0 dated Aug. 27, 2014.
Extended European Search Report for European Application No. 13795353.6 dated Nov. 13, 2015.
International Preliminary Report on Patentability for PCT/US09/39498 dated Dec. 8, 2010.
International Preliminary Report on Patentability for PCT/US13/43487 dated Dec. 2, 2014.
International Search Report and Written Opinion for PCT/US17/51538 dated Feb. 6, 2018.
International Search Report for PCT/US09/39498 dated Oct. 29, 2009.
International Search Report for PCT/US11/39550 dated Sep. 29, 2011.
International Search Report for PCT/US12/30233 dated Jul. 3, 2012.
International Search Report for PCT/US13/43487 dated Jan. 7, 2014.
New Zealand First Examination Report for 616678 dated Jun. 13, 2014.
Response to U.S. Office Action for U.S. Appl. No. 14/150,652 dated Aug. 25, 2015.
U.S. Office Action for U.S. Appl. No. 12/870,763 dated Sep. 17, 2010.
U.S. Office Action for U.S. Appl. No. 12/870,774 dated Jul. 17, 2012.
U.S. Office Action for U.S. Appl. No. 12/870,774 dated Mar. 5, 2012.
U.S. Office Action for U.S. Appl. No. 13/069,860 dated Mar. 29, 2012.
U.S. Office Action for U.S. Appl. No. 13/304,292 dated Feb. 21, 2012.
U.S. Office Action for U.S. Appl. No. 14/150,652 dated Mar. 25, 2015.
U.S. Office Action for U.S. Appl. No. 14/150,652 dated Sep. 8, 2015.
U.S. Office Action for U.S. Appl. No. 15/205,093 dated Nov. 24, 2017.
Written Opinion for PCT/US09/39498 dated Apr. 10, 2010.
Abatangelo et al., "Biocompatibility and enzymatic degradation studies on sulphated hyaluronic acid derivatives," 1997, Biomaterials, 18:1411-1415.
Allmen et al., "V domain of RAGE interacts with AGEs on prostate carcinoma cells," 2008, The Prostate, 68:748-758.
Anderson et al., "Pentosan polysulfate: a review of its use in the relief of bladder pain or discomfort in interstitial cystitis," 2006, Drugs, 66:821-835.
Anumolu et al., "Fabrication of highly uniform nanoparticles from recombinant silk-elastin-like protein polymers for therapeutic agent delivery," 2011, ACS Nano, 5:5374-5382.
Barbucci, "Low- and high-resolution nuclear magnetic resonance (NMR) characterisation of hyaluronan-based native and sulfated hydrogels," 2006, Carbohydrate Res., 341:1848-1858.
Baykal et al., "Intravesical heparin and peripheral neuromodulation on interstitial cystitis," 2005, Urol. Int., 74:361-364.
Benck et al., "Proteinuria-lowering effect of heparin therapy in diabetic nephropathy without affecting the renin-angiotensin-aldosterone system," 2007, Clin. J. Am. Soc. Nephrol., 2:58-67.

Benesova et al., "Stability evaluation of n-alkyl hyaluronic acid derivatives by DSC and TG measurement," 2006, J. Therm. Analys. Calorim., 83:341-348.
Benitez et al., "Targeting hyaluronidase for cancer therapy: antitumor activity of sulfated hyaluronic acid in prostate cancer cells," 2011, Canc. Res., 71:4085-4095.
Bohlender et al., "Advanced glycation end products in the kidney," 2005, Am. J. Renal. Physiol., 289-F645-F659.
Cappello et al., "In-situ self-assembling protein polymer gel systems for administration, delivery, and release of drugs," 1998, J. Controlled Release, 53:105-117.
Cen et al., "Assessment of in vitro Bioactivity of Hyaluronic Acid and Sulfated Hyaluronic Acid Functionalized Electroactive Polymer," 2004, Biomacromolecules, 5:2238-2246.
Chang et al., "Nanochemical stimulus accelerates and directs the self assembly of silk-elastin-like nanofibers," 2011, J. Am. Chem. Soc., 133:1745-1747.
Cheng et al., "Expression profiling of endogenous secretory receptor for advanced glycation end products in human organs," 2005, Modern Pathol., 18:1385-1396.
Dausse et al., "Cartilage Repair Using New Polysaccharidic Biomaterials: Macroscopic, Histological and Biochemical Approaches in a Rat Model of Cartilage Defect," 2003, Osteoarthritis and Cartilage, 11:16-28.
Dinerman et al., "Swelling behavior of a genetically engineered silk-elastinlike protein polymer hydrogel," 2002, Biomaterials, 4203-4210.
Dubbini et al., "Injectable hyaluronic acid/PEG-p(HPMAm-lac)-based hydrogels dually cross-linked by thermal gelling and Michael addition," 2015, European Polymer J., 72:423-437.
Greish et al., "Silk-elastinlike protein polymers improve the efficiency of adenovirus thymidine kinase enzyme prodrug therapy of head and neck tumors," 2010, J. Gene Med., 12:572-579.
Gustafson et al., "Silk-elastinlike hydrogel improves the safety of adenovirus-mediated gene-directed enzyme-prodrug therapy," 2010, Mol. Pharm., 7:1050-1056.
Gustafson et al., "Silk-elastinlike protein polymers for matrix-mediated cancer gene therapy," 2010, Advanced Drug Delivery Rev., 62:1509-1523.
Gustafson et al., "Silk-elastinlike recombinant polymers for gene therapy of head and neck cancer: from molecular definition to controlled gene expression," 2009, J. Controlled Release, 140:256-261.
Gustafson et al., "Synthesis and characterization of a matrix-metalloproteinase responsive silk-elastinlike protein polymer," 2013, Biomacromolecules, 14:618-625.
Gustafson, "Silk-elastinlike protein polymers for adenoviral cancer gene therapy," 2012, PhD Dissertation, University of Utah Doc. No. 3547213.
Toft et al., "Recent developments of intravesical therapy of painful bladder syndrome/interstitial cystitis: a review," 2006, Curr. Opin. Urol., 16:268-272.
Varela et al., "Chemoembolization of hepatocellular carcinoma with drug eluting beads: Efficacy and doxorubicin pharmacokinetics," 2007, J. Hepatology, 46:474-481.
Vartak et al., "Matrix metal loproteases: underutilized targets for durg delivery," 2007, J. Drug Target., 15:1-20.
Vemula et al., "Self-assembled prodrugs: an enzymatically triggered drug-delivery platform," 2009, 30:383-393.
Wirostko et al., "Ophthalmic usesofa thiol-modified hyaluronan-based hydrogel," 2014, Adv. Wound Care, 3:708-716.
Yamamoto et al., "Absorption of water-soluble compounds with different molecular weights and [Asu1.7]-eel calcitonin from various mucosal administration sites," 2001, J. Controlled Release, 76:363-374.
Hammer, "Viscous corneal protection by sodium hyaluronate, chondroitin sulfate, and methylcellulose," 1984, Invest. Ophthalmol. Vis. Sci., 25:1329-1332.
Hermani et al., "Calcium-binding proteins S100A8 and S100A9 as Novel Diagnostic Markers in Human Prostate Cancer," 2005, Clin. Cancer Res., 11:5146-5152.

(56) References Cited

OTHER PUBLICATIONS

Hinize et al., "Modifications of hyaluronan influence the interaction with human bone morphogenetic protein-4 (hBMP-4)," 2009, Biomacromolecules, 10:3290-3297.
Hu et al., "Biomaterials derived from silk-tropoelastin protein systems," 2010, Biomater., 31:8121-8131.
Iavazzo et al., "Hyaluronic acid; an effective alternative treatment of interstitial cystitis, recurrent urinary tract infections, and hemorrhagic cystitis?" 2007, Europ. Urol., 51:1534-1541.
Ishiguro et al., "Receptor for advanced glycation end products (RAGE) and its ligand, amphoterin, are overexpressed and associated with prostate cancer development," 2005, The Prostate, 64:92-100.
Jeanloz, "The methyl ester of methylated hyaluronic acid," 1952, J. Biol. Chem., 197:141-150.
Jones et al., "Epidemiology of interstitial cystitis," 1997, Urology, 49 (5A Suppl.):2-9.
Kaye et al., "Methylation studies on hyaluronic acid," 1951, Biochem. J., 48:249-255.
Kyyronen, "Methylprednisolone esters of hyaluronic acid in ophthalmic drug delivery: in vitro and in vivo release studies," 1992, Int. J. Pharmaceutics, 80:161-169.
Limberg et al., "Topical application of hyaluronic acid and chondroitin sulfate in the treatment of dry eyes," 1987, Am. J. Ophthalmol., 103:194-197.
Llovet et al., "Systematic review of randomized trials for unresectable hepatocellular carcinoma: Chemoembolization improves survival," 2003, Hepatology, 37:429-442.
Lukban et al., "Current management of interstitial cystitis," 2002, Urol. Clin. N. Am., 29:649-660.
Macrae et al., "The effects of sodium hyaluronate, chondroitin sulfate, and methyl cellulose on the corenal endothelium and intraocular pressure," 1983, Am. J. Ophthalmol., 95:332-341.
Maruyama et al., "Conformational changes and anticoagulant activity of chondroitin sulfate following its O-sulfonation," 1998, Carb. Res., 306-35-43.
Matsuda et al., "Therapeutic effect of sulphated hyaluronic acid, a potential selectin-blocking agent, on experimental progressive mesangial proliferatie glomerulonephritis," 2002, J. Pathol., 198:407-414.
Mecham et al., "Elastin degradation by matrix metalloproteinases," 1997, J. Biol. Chem., 272:18071-18076.
Megeed et al., "Genetically engineered silk-elastinlike protein polymers for controlled drug delivery," 2002, Adv. Drug Delivery Rev., 54:1075-1091.
Megeed et al., "In vitro and in vivo evaluation of recombinant silk-elastinlike hydrogels for cancer gene therapy," 2004, J. Controlled Release, 94:433-445.
Mracek et al., "The Diffusion Process of Sodium Hyaluronate (Na-HA) and Na-HA-n-alkyl Derivatives Films Swelling," 2007, J. Biomed. Mater. Res. Part A, 83A/1:184-190.
Myint et al., "RAGE Control of Diabetic Nephropathy in a Mouse Model: Effects of RAGE Gene Disruption and Administration of Low-Molecular Weight Heparin," 2006, Diabetes, 55:2510-2522.
Nagira et al., "Effects of sulfated hyaluronan on keratinocyte differentiation and Wnt and Notch gene expression," 2007, Biomaterials, 2:844-850.
Nakamura et al., "Concentration and molecular weight dependency of rabbit corneal epithelial wound healing on hyaluronan," 1992, Curr. Eye Res., 11:981-986.
Nasagawa et al., "Chemical sulfation of preparations of chondroitin 4- and 6-sulfate, and dermatan sulfate. Preparation of chondroitin sulfate like materials from chondroitin 4-sulfate," 1986, Carb. Res., 158:183-190.
Nepp et al., "The clinical use of viscoelastic artificial tears and sodium chloride in dry-eye syndrome," 2001, Biomaterials, 22:3305-3310.
Netzel-Arnett et al., "Comparative sequence specificities of human 72- and 92-kDa gelatinases (type IV collagenases) and PUMP (matrilysin)," 1993, Biochemistry, 32:6427-6432.
Numata et al., "Silk-based delivery systems of bioactive molecules," 2010, Adv. Drug Delivery Rev., 62:1497-1508.
Ogawa et al., "Sulfated Hyaluronic Acid, a Potential Selectin Inhibitor, Ameliorates Experimentally Induced Crescentic Glomerulonephritis," 2005, Experimental Nephrology, 99:e26-e32.
Parsons et al., "Treatment of interstitial cystitis with intravesical heparin," 1994, Br. J. Urol., 73:504-507.
Parsons, "Successful downregulation of bladder sensory nerves with combination of heparin and alkalinized lidocaine in patients with interstitial cystitis," 2005, Urology, 74:45-48.
Payne et al., "Interstitial cystitis and painful bladder syndrome," 2007, J. Urol., 177:2042-2049.
Petit et al., "Controlled sulfation of natural anionic bacterial polysaccharides can yield agents With specific regenerating activity in vivo," 2004, Biomacromolecules, 5:445-452.
Poursaid et al., "In situ gelling silk-elastinlike protein polymer for transarterial chemoembolization," 2015, Biomaterials, 57:142-152.
Poursaid et al., "Silk-elastinlike protein polymer liquid chemoembolic for localized release of doxorubicin and sorafenib," 2016, Mol. Pharm., 13:2736-2748.
Poursaid, "Design and development of silk-elastinlike protein polymer liquid embolics for treatment of hepatocellular carcinoma," 2016, PhD Dissertation (partial), University of Utah.
Price, "Effect of shear on physicochemical properties of matrix metallorproteinase responsive silk-elastinlike hydrogels," 2014, J. Controlled Release, 195:92-98.
Sant et al., "A pilot clinical trial of oral pentosan polysulfate and oral hydroxyzine in patients with interstitial cystitis," 2003, J. Urol., 170:810-815.
Satoh et al., "The Basic Research on Physiological Property of Functionalized Hyaluronan (II): Effect of Sulfated Hyaluronan on Histamine Release from the Mast Cell," 2004, Fiber, 60:137-143.
Satoh et al., "The research on physiological property of functionalized hyaluronan: interaction between sulfated hyaluronan and plasma proteins," 2004, Polymers for Advanced Technologies, 15:720-725.
SBIR Award ID 93482, "Sulfated Polysaccharide Derivatives for the Treatment of Rosacea," Glycomira, 2009, Abstract Only, <http://www.sbir.gov/sbiresearch/detail/192860>, Accessed Jun. 27, 2014.
SBIR Award ID 93781, "Sulfated Polysaccharide Derivatives for the Treatment of Macular Degeneration," Glycomira, 2009, Abstract Only, <http://www.sbir.gov/sbiresearch/detail/192862>, Accessed Jun. 27, 2014.
Skjot-Arkil et al., "Measurement of MMP-9 and -12 degraded elastin (ELM) provides unique information on lung tissue degradation," 2012, BMC Pulmonary Medicine, 46:1-12.
Steinhoff et al., "The efficacy of chondroitin sulfate 0.2% in treating interstitial cystitis," 2002, Can. J. Urol., 9:1454-1458.
Suzuki et al., "Preparation and inhibitory activity on hyaluronidase of fully O-sulfated hyaluro-oligosaccharides," 2001, Glycobiol., 11:57-64.
Talman et al. "Ocular changes induced by polysaccharides. II. Detection of hyaluronic acid sulfate after injection into ocular tissues," 1959, Am. J. Ophthalmol., 47:428-437.
Talman et al., "Ocular changes induced by polysaccharides. III. Paper chromatographic fractionation of a biologically active hyaluronic acid sulfate preparation," 1959, Am. J. Ophthalmol., 48:560-572.
Theoharides et al., "A pilot open label of CystoProtek in interstitial cystitis," 2005, Int. J. Immunopathol. Pharmacol., 18:183-188.
Theoharides et al., "Critical role of mast cells in inflammatory diseases and the effect of acute stress," 2004, J. Neuroimmunol., 146:1-12.
Theoharides et al. "New agents for the medical treatment of interstitial cystitis," 2001, Expert Opin. Investig. Drugs, 10:521-546.
Theoharides, "Treatment approaches for painful bladder syndrome/interstitial cystitis," 2007, Drugs, 67:215-235.
U.S. Appl. No. 15/064,142, U.S. Pat. No. 9,932,389.
U.S. Appl. No. 14/403,979, 2015/0152165.
U.S. Appl. No. 16/006,015, 2018/0353522.
U.S. Appl. No. 14/613,523, U.S. Pat. No. 9,549,945.
U.S. Appl. No. 15/381,187, U.S. Pat. No. 10,226,481.

(56) References Cited

OTHER PUBLICATIONS

PCT/US2017/051538, WO 2018/053111.

* cited by examiner

FIG. 7A-F

IN SITU GELLING COMPOSITIONS FOR THE TREATMENT OR PREVENTION OF INFLAMMATION AND TISSUE DAMAGE

CROSS REFERENCE TO RELATED APPLICATIONS

This application claims priority upon U.S. provisional application Ser. Nos. 62/395,313 filed on Sep. 15, 2016 and 62/458,618 filed Feb. 14, 2017. These applications are hereby incorporated by reference in their entirety.

ACKNOWLEDGMENTS

This invention was made with government support under Grant R01 CA107621 awarded by the National Institutes of Health. The government has certain rights in the invention.

BACKGROUND

The treatment of inflammation in patients has been the subject of extensive research. Conventionally accepted treatments of inflammation may involve UV phototherapy, corticosteroids and glucocorticoids, acitretin, cyclosporine, and methotrexate. However, each of these treatments may cause serious side effects ranging from immune suppression and liver disease to thinning skin and causing birth defects. Due to partial or complete ineffectiveness, these treatments often leave patients unsatisfied with their results.

One problem associated with the treatment of inflammation is the local delivery of an anti-inflammatory agent at the site of inflammation. An example of this is the delivery of anti-inflammatory agents to a body cavity in the subject where inflammation is present. In situations like this, it would desirable to deliver a solution composed of the anti-inflammatory agent into the body cavity where it subsequently forms a gel under physiological conditions. Thus, the gel would remain in the body cavity and locally deliver the anti-inflammatory agent at the site of inflammation. The compositions described herein address this approach.

SUMMARY

Described herein are in situ gelling compositions. The compositions include an anti-inflammatory polysaccharide and a gelling polymer, wherein the composition is a liquid prior to administration to a subject but converts to a gel upon administration to the subject. The compositions described herein have numerous applications with respect to the local treatment (reduction or prevention) of inflammation and/or tissue damage.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
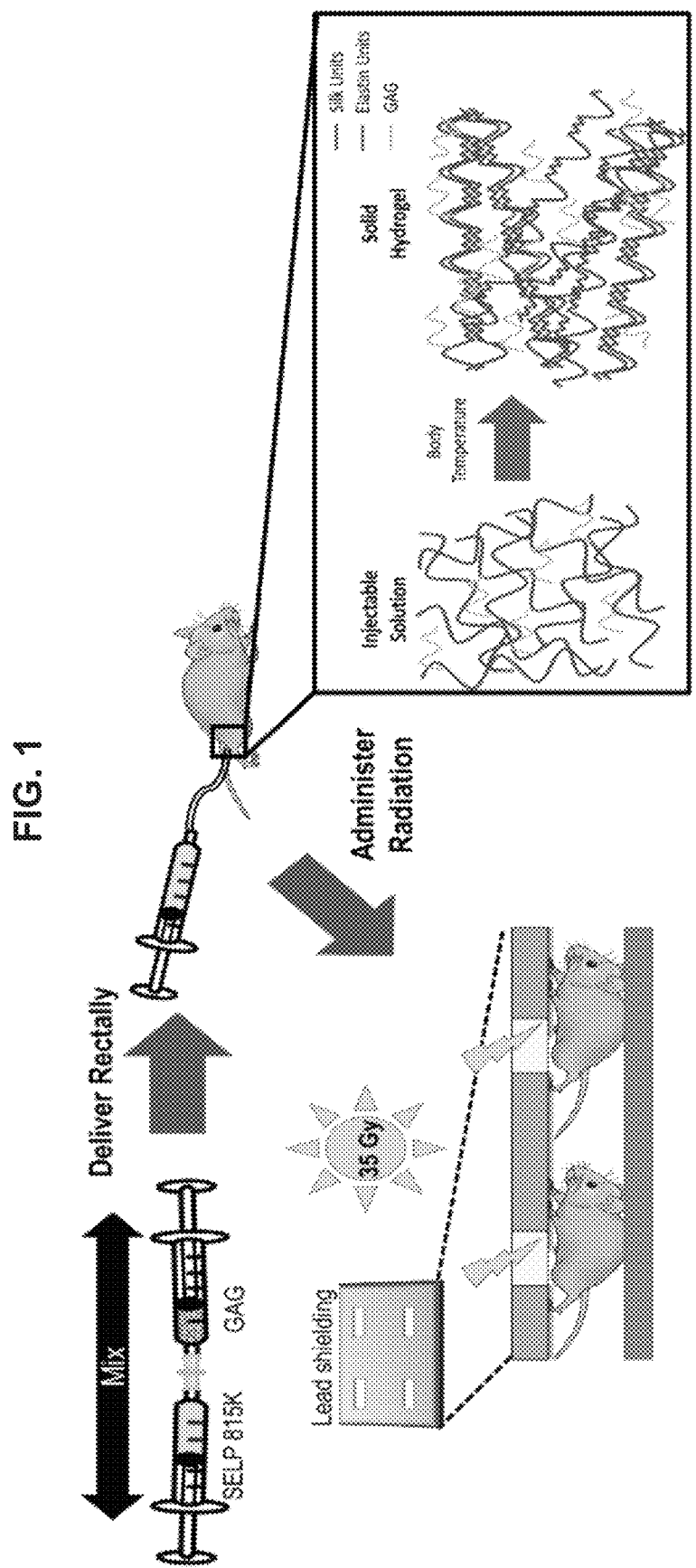
FIG. 1 shows a schematic of an experimental treatment protocol in which mice are injected rectally with a solution of silk-elastinlike protein polymer (SELP 815K) and semi-synthetic glycosaminoglycan (GAG GM-0111) prior to treatment of the lower abdomen with radiation. The administration of this SELP 815K/GAG GM-0111 enema protects the rectum from radiation-induced damage.

Before the present materials, articles, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In the specification and in the claims that follow, reference will be made to a number of terms that shall be defined to have the following meanings:

It must be noted that, as used in the specification and appended claims, the singular forms "a," "an," and "the" include plural referents unless the context clearly dictates otherwise. Thus, for example, reference to "an excipient" includes mixtures of two or more excipients, and the like.

"Optional" or "optionally" means that the subsequently described event or circumstance can or cannot occur, and that the description includes instances where the event or circumstance occurs and instances where it does not. For example, the pharmaceutical compositions described herein may optionally contain biologically active ingredients, where the biologically active ingredients may or may not be present.

As used herein, the term "about" is used to provide flexibility to a numerical range endpoint by providing that a given value may be "a little above" or "a little below" the endpoint without affecting the desired result.

Throughout this specification, unless the context dictates otherwise, the word "comprise," or variations such as "comprises" or "comprising," will be understood to imply the inclusion of a stated element, integer or step, or group of elements, integers or steps but not the exclusion of any other element, integer or step, or group of elements, integers or steps.

A "subject" as used in the specification and concluding claims, refers to a human or non-human animal. For example, the subject is a non-human animal (domesticated, wild, farm) such as, for example, a horse, cat, dog, cow, pig, sheep, goat, mouse, rabbit, chicken, rat, or guinea pig.

A "residue" of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, hyaluronan that contains at least one —OH group can be represented by the formula Y—OH, where the Y is the remainder (i.e., residue) of the hyaluronan molecule.

A "hydrogel" as used in the specification and concluding claims, refers to a semisolid composition constituting a substantial amount of water. A hydrogel can be formed from a network of polymer chains in which polymers or mixtures thereof are dissolved or dispersed. Hydrogels are composed of three dimensional polymer networks that will swell without dissolving when placed in water or other biological fluids. A hydrogel is significantly more viscous than water or other similar liquid. Hence, for purposes herein, a hydrogel is generally a non-liquid form.

The term "treat" as used herein is defined as maintaining or reducing the symptoms of a pre-existing condition. The term "prevent" as used herein is defined as eliminating or reducing the likelihood of the occurrence of one or more symptoms of a disease or disorder. The term "inhibit" as used herein is the ability of the compounds described herein to completely eliminate the activity or reduce the activity when compared to the same activity in the absence of the compound.

The term "admixing" is defined as mixing two components together so that there is no chemical reaction or physical interaction. The term "admixing" also includes the chemical reaction or physical interaction between the two components. As an example, covalent bonding to reactive therapeutic drugs, e.g., those having nucleophilic groups, can be undertaken with respect to the compounds in the compositions disclosed herein. Second, non-covalent entrapment of a pharmacologically active agent in a cross-linked polysaccharide or cross-linked protein matrix is also possible. Third, electrostatic or hydrophobic interactions or physical constraint by the matrix can facilitate retention of a pharmaceutically-acceptable compound in the compositions disclosed herein.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the individual range. Thus, included in this numerical range are individual values such as 2, 3, and 4, the sub ranges such as from 1-3, from 2-4, from 3-5, etc., as well as 1, 2, 3, 4, and 5 individually. The same principle applies to ranges reciting only one numerical value as a minimum or maximum.

Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a class of silk-elastinlike proteins A, B, and C are disclosed, as well as a class of semi-synthetic glycosaminoglycans (GAGs) D, E, and F, and an example combination of A+D is disclosed, then even if each is not individually recited, each is individually and collectively contemplated. Thus, in this example, each of the combinations A+E, A+F, B+D, B+E, B+F, C+D, C+E, and C+F is specifically contemplated and should be considered from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered from disclosure of A, B, and C; D, E, and F; and the example combination of A+D. This concept applies to all aspects of the disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Described herein are in situ gelling compositions for the treatment or prevention of inflammation. Each component used to prepare the in situ gelling compositions as well as methods for preparing and using the compositions are described in detail below.

Anti-Inflammatory Polysaccharides

The compositions described herein include one or more anti-inflammatory polysaccharides. In one aspect, the polysaccharide is a glycosaminoglycan (GAG). Glycosaminoglycans can be sulfated or non-sulfated. A GAG is one molecule with many alternating subunits. For example, hyaluronan is (GlcNAc-GlcUA-)x. Other GAGs are sulfated at different sugars. Generically, GAGs are represented by the formula A-B-A-B-A-B, where A is an uronic acid and B is an amino sugar that is either O- or N-sulfated, where the A and B units can be heterogeneous with respect to epimeric content or sulfation. Any natural or synthetic polymer containing uronic acid can be used. Examples of glycosaminoglycans include, but are not limited to, chondroitin sulfate, dermatan, heparan, heparin, dermatan sulfate, and heparan sulfate.

In one aspect, the anti-inflammatory polysaccharide is a sulfated hyaluronan or the pharmaceutically acceptable salt or ester thereof. In one aspect, the sulfated hyaluronan has a degree of sulfation from 0.1 to 4.0 per disaccharide unit. In another aspect, the sulfated hyaluronan has a degree of sulfation from 0.1, 0.5, 1.0, 1.5, 2.0, 2.5, 3.0, 3.1, 3.2, 3.3, 3.4, 3.5, 3.6, 3.7, 3.8, 3.9, or 4.0 per disaccharide unit, where any value can be a lower and upper end-point of a range (e.g., 3.0 to 4.0, 3.2 to 3.8, etc.).

In another aspect, the average molecular weight of the sulfated hyaluronan is less than 1,000 kDa, less than 900 kDa, less than 800 kDa, less than 700 kDa, less than 600 kDa, less than 500 kDa, less than 400 kDa, less than 300 kDa, less than 200 kDa, less than 100 kDa, less than 50 kDa, less than 25 kDa, less than 10 kDa, or less than 5 kDa. In another aspect, the sulfated hyaluronan has an average molecular size from 0.5 kDa to less than 50 kDa, 2 Da to 20 kDa, or 3 kDa to 10 kDa. In a further aspect, the sulfated hyaluronan has an average molecular size from 0.5 kDa to 10 kDa or 1 kDa to 5 kDa. Depending upon reaction conditions, one or more different hydroxyl groups present in the low molecular hyaluronan or hyaluronan oligosaccharide can be sulfated. In one aspect, the primary C-6 hydroxyl proton of the N-acetyl-glucosamine residue of the low molecular hyaluronan or hyaluronan oligosaccharide is sulfated. In another aspect, the primary C-6 hydroxyl proton of the N-acetyl-glucosamine residue of hyaluronan and at least one C-2 hydroxyl proton or C-3 hydroxyl proton of a uronic acid residue or at least one C-4 hydroxyl proton of an N-acetyl-glucosamine residue is substituted with a sulfate group. In another aspect, the primary C-6 hydroxyl proton of the N-acetyl-glucosamine residue of the low molecular hyaluronan or hyaluronan oligosaccharide and at least one C-2 hydroxyl proton and C-3 hydroxyl proton of a uronic acid residue and at least one C-4 hydroxyl proton of an N-acetyl-glucosamine residue is substituted with a sulfate group. In another aspect, 0.001%, 0.01%, 0.1%, 1%, 5%, 10%, 20%, 30%, 40%, 50%, 60%, 70%, 80%, 90%, 95%, or less than 100%, or any range thereof of hydroxyl protons present on the low molecular hyaluronan or hyaluronan oligosaccharide can be deprotonated and subsequently sulfated.

In another aspect, the sulfated hyaluronan has (1) 100% of the primary C-6 hydroxyl protons of the N-acetyl-glucosamine residue of the sulfated hyaluronan are substituted with a sulfate group, (2) a degree of sulfation from 3.0 to 4.0, and (3) an average molecular weight from 1 kDa to 3 kDa.

The hyaluronan starting material used to produce the sulfated hyaluronan can exist as the free acid or the salt thereof. Derivatives of hyaluronan starting material can also be used herein. The derivatives include any modification of the hyaluronan prior to sulfation. A wide variety of molecular weight hyaluronans can be used herein for the depolymerization step. In one aspect, the hyaluronan has a molecular weight greater than 1,000 kDa prior to depolymerization. In another aspect, the hyaluronan can have a molecular weight of 10 kDa to 1,000 kDa prior to depolymerization. A wide variety of hyaluronan molecular weights can also be employed for the sulfation step. In one aspect, the hyaluronan starting material can be converted to low molecular hyaluronan or a hyaluronan oligosaccharide prior to sulfation to produce the partially or fully sulfated hyaluronan. As will be discussed in greater detail below, low molecular weight hyaluronan is hyaluronan that has been degraded with an acid or base. Alternatively, hyaluronan oligosaccharide is produced by degrading hyaluronan with an enzyme such as, for example, hyaluronan synthase or hyaluronidase in a controlled fashion. Subsequently, hyaluronan oligosaccharides having different molecular weights can be separated by GPC or ion exchange separation. Exemplary procedures for producing low molecular weight hyaluronan or hyaluronan oligosaccharide from hyaluronan are provided in WO 2011/156445.

In one aspect, the low molecular hyaluronan or hyaluronan oligosaccharide being sulfated has a molecular weight from 1 kDa to 2,000 kDa. In another aspect, the low molecular hyaluronan or hyaluronan oligosaccharide being sulfated has a molecular weight from 5 kDa to 500 kDa, 10 kDa to 200 kDa, or 20 kDa to 100 kDa. Exemplary procedures for preparing low molecular weight hyaluronan are provided in WO 2011/156445. As discussed above, the molecular weight of the hyaluronan can be modified by cleaving hyaluronan with an acid or base to produce lower molecular weight hyaluronan. In certain aspects, the hyaluronan starting material or a derivative thereof is not derived from an animal source. In these aspects, the hyaluronan can be derived from other sources such as bacteria. For example, a recombinant *B. subtilis* expression system can be used to produce the hyaluronan starting material.

After the low molecular hyaluronan or hyaluronan oligosaccharide has been treated with a base, it is reacted with a sulfating agent to produce the partially or fully sulfated hyaluronan. Sulfating agents commonly used in organic synthesis can be used herein. Examples of sulfating agents include, but are not limited to, pyridine-sulfur trioxide complex or the triethylamine-sulfur trioxide complex. In one aspect, low molecular hyaluronan or hyaluronan oligosaccharide can be converted to the tributylamine salt, lyophilized, resuspended in dimethylformamide, and subsequently treated with a sulfating agent (e.g., pyridine-sulfur trioxide complex) to sulfate one or more hydroxyl protons.

In one aspect, when the sulfating agent is a pyridine-sulfur trioxide complex, a pyridinium adduct of the sulfated hyaluronan is produced, where pyridine is covalently attached to the sulfated hyaluronan. Not wishing to be bound by theory, when hyaluronan is reacted with the pyridine-sulfur trioxide complex in a solvent such as, for example, DMF, a small amount of acid is produced from traces of water present in situ, which causes partial depolymerization resulting in a free reducing end group. The hydroxyl group of the hemiketal can ultimately be sulfated to produce a sulfated intermediate, which subsequently reacts with free pyridine produced in situ to produce the pyridinium adduct. Thus, the sulfated hyaluronan used herein can include a mixture of sulfated hyaluronan that does not have pyridine covalently attached to the molecule and sulfated hyaluronan that does have pyridine covalently attached to the molecule. In one aspect, from 0.01% to 100%, 0.1% to 10%, or 0.15% to 2.5% of the sulfated hyaluronan has pyridine covalently attached to the molecule. In another aspect, the molecular weight of the pyridinium adduct of the sulfated hyaluronan is less than or equal to 10 kDa. In other aspects, the molecular weight is 0.1 kDa, 0.5 kDa, 1 kDa, 2 kDa, 3 kDa, 4 kDa, 5 kDa, 6 kDa, 7 kDa, 8 kDa, 9 kDa, or 10 kDa, where any value can for the lower and upper end-point of a molecular weight range.

In another aspect, the anti-inflammatory polysaccharide is a modified hyaluronan or a pharmaceutically acceptable salt or ester thereof, wherein said hyaluronan or its pharmaceutically acceptable salt or ester comprises at least one sulfate group and at least one primary C-6 hydroxyl position of an N-acetyl-glucosamine residue comprising an alkyl group or fluoroalkyl group (referred to herein as "SAGE").

In one aspect, at least one primary C-6 hydroxyl proton of the N-acetyl-glucosamine residue of hyaluronan is substituted with an alkyl group. The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. In one aspect, the alkyl group is a $C_1$-$C_{10}$ branched or straight chain alkyl group. In a further aspect, the alkyl group is methyl. The alkyl group can be unsubstituted or substituted. In the case when the alkyl group is substituted, one or more hydrogen atoms present on the alkyl group can be replaced with or more groups including, but not limited to, alkynyl, alkenyl, aryl, halide, nitro, amino, ester, ketone, aldehyde, hydroxy, carboxylic acid, aralkyl, or alkoxy.

In another aspect, at least one primary C-6 hydroxyl proton of the N-acetyl-glucosamine residue of hyaluronan is substituted with a fluoroalkyl group. The term "fluoroalkyl group" as used herein is a branched or unbranched saturated hydrocarbon group of 1 to 24 carbon atoms, wherein at least one of the hydrogen atoms is substituted with fluorine. In certain aspects, the fluoroalkyl group includes at least one trifluoromethyl group. In other aspects, the fluoroalkyl group has the formula —$CH_2(CF_2)_nCF_3$, wherein n is an integer of 1, 2, 3, 4, 5, 6, 7, 8, 9, or 10. In one aspect, the fluoroalkyl group is —$CH_2CF_2CF_3$ or —$CH_2CF_2CF_2CF_3$.

Alkylated and fluoroalkylated hyaluronan useful herein as well as methods for making the same are provided in WO2009/124266. The hyaluronan starting material can exist as the free acid or the salt thereof. Derivatives of hyaluronan starting material can also be used herein. The derivatives include any modification of the hyaluronan prior to the alkylation or fluoroalkylation step. A wide variety of molecular weight hyaluronan can be used herein. In one aspect, the hyaluronan has a molecular weight greater than 10 kDa prior to alkylation or fluoroalkylation. In another aspect, the hyaluronan has a molecular weight from 25 kDa to 1,000 kDa, 100 kDa to 1,000 kDa, 25 kDa to 500 kDa, 25 kDa to 250 kDa, or 25 kDa to 100 kDa prior to alkylation or fluoroalkylation. In certain aspects, the hyaluronan starting material or a derivative thereof is not derived from an animal source. In these aspects, the hyaluronan can be derived from other sources such as bacteria. For example, a recombinant *B. subtilis* expression system can be used to produce the hyaluronan starting material.

The hyaluronan starting material or derivative thereof is initially reacted with a sufficient amount of base to deprotonate at least one primary C-6 hydroxyl proton of the N-acetyl-glucosamine residue. The selection of the base can vary. For example, an alkali hydroxide such as sodium hydroxide or potassium hydroxide can be used herein. The concentration or amount of base can vary depending upon the desired degree of alkylation or fluoroalkylation. In one aspect, the amount of base is sufficient to deprotonate at least 0.001% of the primary C-6 hydroxyl protons of the N-acetyl-glucosamine residue of the hyaluronan starting material or derivative thereof. In other aspects, the amount of base is sufficient to deprotonate from 0.001% to 50%, 1% to 50% 5% to 45%, 5% to 40%, 5% to 30%, 5% to 20%, 10% to 50%, 20% to 50%, or 30% to 50% of the primary C-6 hydroxyl protons of the N-acetyl-glucosamine residue of the hyaluronan starting material or derivative thereof. It is understood that the more basic the solution, the more likely are chain cleavage reactions and the higher the degree of alkylation/fluoroalkylation that can be achieved. For example, other hydroxyl groups present on hyaluronan (e.g., 2-OH and/or 3-OH can be alkylated or fluoroalkylated). In one aspect, all of the hydroxyl groups present on hyaluronan can be alkylated or fluoroalkylated. In other aspects, 0.001%, 0.01%, 0.1%, 1%, 5%, 10%, 20%, 30%, 40%, 50%, 60%, 70%, 80%, 90%, 95%, 100%, or any range thereof of hydroxyl protons present on hyaluronan can be deprotonated and subsequently alkylated or fluoroalkylated.

After the hyaluronan starting material or derivative thereof has been treated with a base, the deprotonated hyaluronan is reacted with an alkylating agent or fluoroalkylating agent to produce the SAGE. Examples of alkylating agents include, but are not limited to, an alkyl halide. Alkyl bromides and iodides are particularly useful. Similarly, the fluoroalkylating agent can include a fluoroalkyl halide. Alkylating agents and fluoroalkylating agents commonly used in organic synthesis can be used herein.

In certain aspects, it is desirable to sulfate the alkylated or fluoroalkylated SAGEs described above. In one aspect, the alkylated or fluoroalkylated SAGE is sulfated by reacting the alkylated or fluoroalkylated SAGE with a sulfating agent to produce a sulfated product. The degree of sulfation can vary from partial sulfation to complete sulfation. In general, free hydroxyl groups present on the alkylated or fluoroalkylated hyaluronan or a derivative thereof can be sulfated. In one aspect, at least one C-2 hydroxyl proton and/or C-3 hydroxyl proton is substituted with a sulfate group. In another aspect, the degree of sulfation is from 0.5, 1.0, 1.5, 2.0, 2.5, 3.0, 3.5 or any range thereof per disaccharide unit of the alkylated or fluoroalkylated SAGE. In one aspect, the alkylated or fluoroalkylated SAGE can be treated with a base to deprotonate one or more hydroxyl protons followed by the addition of the sulfating agent. The sulfating agent is any compound that reacts with a hydroxyl group or deprotonated hydroxyl group to produce a sulfate group. The molecular weight of the SAGE can vary depending upon reaction conditions. In one aspect, the molecular weight of the SAGE is from 2 kDa to 500 kDa, 2 kDa to 250 kDa, 2 kDa to 100 kDa, 2 kDa to 50 kDa, 2 kDa to 25 kDa, or from 2 kDa to 10 kDa.

In one aspect, the alkyl group of the SAGE is methyl and at least one C-2 hydroxyl proton and/or C-3 hydroxyl proton of hyaluronan is substituted with a sulfate group. In another aspect, the alkyl group of the SAGE is methyl, at least one C-2 hydroxyl proton and/or C-3 hydroxyl proton of hyaluronan is substituted with a sulfate group, and the compound has a molecular weight of 2 kDa to 200 kDa after alkylation.

Any of the sulfated and alkylated/fluoroalkylated hyaluronan useful herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine. Also, the esters can be fatty acid esters. For example, the palmitic ester has been prepared and can be used as an alternative esterase-activated prodrug.

Gelling Polymers

The compositions described herein include a gelling polymer. The function of the gelling polymer is to permit the in situ gelling compositions described herein to transform from a liquid at room temperature (approximately 18-23° C.) to a gel at physiological temperature (approximately 37° C.). The viscosity and gelation rate of the in situ gelling composition can be adjusted by varying the selection and amount of the gelling polymer present in the in situ gelling composition.

In one aspect, the gelling polymer is an elastin like protein, a copolymer of N-isopropylacrylamide, alginate, a copolymer of poly-vinyl alcohol, a poloxomer, carboxymethyl cellulose, chitosan, amylum, gelatin, collagen memetic peptide, acrylates (e.g., methacrylates, methyl acrylate, ethyl acrylate, 2-chloroethyl vinyl ether, 2-ethylhexyl acrylate, hydroxyethyl methacrylate, butyl acrylate, butyl methacrylate, trimethylolpropane triacrylate, cyanoacrylate, or any combination thereof), hydroxymethylropylmercapturic acid, polyethylene glycol, phosphazene, or any combination thereof.

In another aspect, the gelling polymer is a silk-elastinlike protein (SELP). SELPs are a class of genetically engineered protein polymers composed of repeating "blocks" of amino acids, referred to as "silk blocks" (Gly-Ala-Gly-Ala-Gly-Ser; SEQ ID NO. 1) and "elastin blocks" (Gly-Val-Gly-Val-Pro; SEQ ID NO. 2). By varying the number of silk and elastin blocks, the rheological properties of the in situ gelling composition can be modified to fit specific applications. For example, the silk to elastin ratio and the length of the silk and elastin block domains as well as the SELP concentration can be modified to optimize gelling upon administration of the in situ gelling composition to the subject.

Examples SELPs useful herein include, but are not limited to,

[(VPGVG)$_8$(GAGAGS)$_2$]$_{18}$; (SEQ ID NO. 3)

[(GVGVP)$_4$(GAGAGS)$_9$]$_{13}$; (SEQ ID NO. 4)

[(VPGVG)$_8$(GAGAGS)$_4$]$_{12}$; (SEQ ID NO. 5)

[(VPGVG)$_8$(GAGAGS)$_6$]$_{12}$; (SEQ ID NO. 6)

[(VPGVG)$_8$(GAGAGS)$_8$]$_{11}$; (SEQ ID NO. 7)

[(VPGVG)$_{12}$(GAGAGS)$_8$]$_8$; (SEQ ID NO. 8)

[(VPGVG)$_{16}$(GAGAGS)$_8$]$_7$; (SEQ ID NO. 9)

[(VPGVG)$_{32}$(GAGAGS)$_8$]$_5$; (SEQ ID NO. 10)

[(GAGAGS)$_{12}$GAAVTGRGDSPASAAGY(GAGAGS)$_5$(GVGVGP)$_8$]$_6$; (SEQ ID NO. 11)

[(GAGAGS)$_2$(GVGVP)$_4$GKGVP(GVGVP)$_3$]$_6$; (SEQ ID NO. 12)

[(GAGAGS)$_2$(GVGVP)$_4$GKGVP(GVGVP)$_3$]$_{12}$; (SEQ ID NO. 13)

[(GAGAGS)$_2$(GVGVP)$_4$GKGVP(GVGVP)$_3$]$_{18}$; (SEQ ID NO. 14)

-continued (SEQ ID NO. 15)
[(GAGAGS)$_2$(GVGVP)$_4$GKGVP(GVGVP)$_3$]$_{17}$(GAGAGS)$_2$;

(SEQ ID NO. 16)
[(GAGAGS)$_2$-(GVGVP)$_4$-(GKGVP)-(GVGVP)$_3$-(GAGAGS)$_2$]$_{1-3}$;

(SEQ ID NO. 17)
[(GAGAGS(GVGVP)$_4$GKGVP(GVGVP)$_3$(GAGAGS)$_2$]$_{12}$;

(SEQ ID NO. 18)
[(GVGVP)$_4$GKGVP(GVGVP)$_{11}$(GAGAGS)$_4$]$_5$(GVGVP)$_4$GKGVP(-GVGVP)$_{11}$(GAGAGS)$_2$;

(SEQ ID NO. 19)
[(GVGVP)$_4$(GKGVP)(GVGVP)$_{11}$(GAGAGS)$_4$]$_7$(GVGVP)$_4$GKGV-P(GVGVP)$_{11}$(GAGAGS)$_2$;

(SEQ ID NO. 20)
[(GVGVP)$_4$GKGVP(GVGVP)$_{11}$(GAGAGS)$_4$]$_9$(GVGVP)$_4$GKGVP(-GVGVP)$_{11}$(GAGAGS)$_2$;

(SEQ ID NO. 21)
[(GAGS(GAGAGS)$_2$(GVGVP)$_4$GKGVP(GVGVP)$_{11}$(GAGAGS)$_5$GA]$_6$;

(SEQ ID NO. 22)
[(GAGAGS)$_2$(GVGVP)$_1$LGPLGP(GVGVP)$_3$GKGVP(GVGVP)$_3$]$_{15}$(GAGAGS)$_2$;

(SEQ ID NO. 23)
[(GAGAGS)$_2$(GVGVP)$_1$GFFVRARR(GVGVP)$_3$GKGVP(GVGVP)$_3$]$_{15}$(GAGAGS)$_2$.

In one aspect, the SELP is 27k, 415K, pSE8Y, pS2E8Y, pS4E8Y, or any combination thereof. In another aspect, the SELP is (815K; SEQ ID NO. 24)
MDPVVLQRRDWENPGVTQLNRLAAHPPFASDPM[GAGS(GAGAGS)$_2$(GVGVP)$_4$GKGVP(GVGVP)$_{11}$(GAGAGS)$_5$GA]$_6$GAMDPGRYQDLRSHHHHHH
or (47K; SEQ ID NO. 25)
MDPVVLQRRDWENPGVTQLVRLAAHPPFASDPMGAGSGAGAGS
[(GVGVP)$_4$GKGVP(GVGVP)$_3$(GAGAGS)$_4$]$_{12}$(GVGVP)$_4$GKGVP(GVGVP)$_2$(GAGAGS)$_2$GAMDPGRYQDLRSHHHHHH.

In another aspect, the gelling polymer can be a variant of a SELP. A "variant" with reference to a silk-like unit or elastin-like unit refers to a silk-like unit or elastin-like unit that has an amino acid sequence that is altered by one or more amino acids. Typically, a unit sequence is altered by 1, 2 or 3 amino acids. The variant can have an amino acid replacement(s), deletions or insertions. For example, the variant can have "conservative" changes, wherein a substituted amino acid has similar structural or chemical properties (e.g. replacement of leucine with isoleucine). In some cases, a variant can have "nonconservative" changes (e.g., replacement of a glycine with a tryptophan). Similar minor variations can also include amino acid deletions or insertions, or both. In addition to the teaching herein, guidance in determining which amino acid residues can be substituted, inserted, or deleted without abolishing bioactivity can be found using computer programs well known in the art, for example, DNASTAR software.

In another aspect, the gelling polymer is a SELP with one or more matrix metalloproteinase (MMP) cleavage sites. MMPs are a family of structurally related endopeptidases that exist in a dynamic balance with tissue inhibitors of metalloproteases (TIMPs) to control a myriad biological functions requiring ECM degradation. Proper function and regulation of MMPs is responsible for diverse biological functions such as angiogenesis, embryonic development, and wound healing. There are over 20 known specific MMPs, divided into subgroups based on their additional domains and known biological functions. The main classes of MMPs are collagenases, gelatinases, stromelysins, matrilysins, membrane-type MMPs, and other unclassified MMPs.

In one aspect, the MMP cleavage site is MMP-2, MMP-9, or a combination thereof. MMPs-2 and -9 are known as gelatinase type A and B, respectively, due to their known ability to degrade gelatin (denatured collagen). In normal situations, MMPs-2 and -9 contribute to several processes involving cell migration and signaling, for example angiogenesis and inflammation/innate immunity. However, these MMPs have also been shown to be overexpressed in certain disease states relative to their expression in healthy tissue.

In addition to MMP-2 and -9 cleavage sites, other protease cleavage sites may be incorporated in the protein polymer (see Table 1). Protease-specific sites can be chosen to target a specific response in the desired microenvironment. The reorganization that occurs during wound healing, if predicted to be a normal response, will use known enzymes during various stages. The breakdown of the matrix will react to the enzymes released during a particular stage to have the most beneficial effect. This includes incorporation of specifically recognized cleavage sites for particular MMPs and other proteases. Sequences that are cleaved by specific enzymes used for extracellular matrix remodeling can be optimized for the release and degradation of recombinant protein hydrogels based on site preferences. The sequence will depend on the MMP or other proteases, regardless of the protein polymer used, and may be inserted in an advantageous location within the protein polymer.

TABLE 1

| MMP Substrates and Cleavage Sequences Cleavage Substrate Sequence | |
|---|---|
| MMP-1, -8 (collagenases) | |
| Substrate | Cleavage Sequence |
| Type I collagen | APGQIAGQ (SEQ ID NO. 26) |
| Type II collagen | GPQGLAGQ (SEQ ID NO. 27) |
| Type III collagen | GPLGIAGI (SEQ ID NO. 28) |
| Aggrecan | IPENFFGV (SEQ ID NO. 29) |

TABLE 1-continued

| MMP Substrates and Cleavage Sequences | Cleavage Substrate Sequence |
|---|---|
| MMP-3 (stromelysins) | |
| Type IX collagen | MAASAKRE (SEQ ID NO. 30) |
| Fibronectin | PFSPLVAT (SEQ ID NO. 31) |
| MMP-2, 9 (gelatinases) | |
| Type IV collagen | GPQGIFGQ (SEQ ID NO. 32) |
| Cartilage link protein | RAIHIQAE (SEQ ID NO. 33) |
| MMP-7 (matrilysin) | |
| Laminin | GPLGIAGQ (SEQ ID NO. 34) |
| Elastin | GPQAIAGQ (SEQ ID NO. 35) |

In another aspect, the gelling polymer is the sequence below, where the MMP-responsive sequence in indicated in bold.

(SEQ ID NO. 36)
[GAGS(GAGAGS)$_2$(GVGVP)$_3$GVGGPQGIFGQPGKGVP(GVGVP)$_{11}$(GAGAGS)$_5$GA]$_6$.

Methods for producing SELPs with one or more matrix metalloproteinase (MMP) cleavage sites is provided in WO 2013181471, which is incorporated by reference.

In one aspect, when the gelling polymer is a SELP, the SELP is sheared prior to formulating the in situ gelling composition. In one aspect, a solution of the SELP is introduced into a homogenizer through a needle valve at a pressure of from 1,500 psi to 17,000 psi. Exemplary methods for producing sheared SELPs is provided in Price et al., "Effect of shear on physicochemical properties of matrix metalloproteinase responsive silk-elastinlike hydrogels." *J. Control. Release* 195, 92-98 (2014). Not wishing to be bound by theory, the shearing of the SELP solution breaks intramolecular hydrogen bonds between the silk-like motifs. Shearing linearizes the protein, which causes reduction in solution viscosity and increases the opportunity for the formation of intermolecular interactions between the silk-like domains of distinct SELP polymers. Shearing can ultimately increase the peak modulus and gelation rate of the gelling polymer. Increased intermolecular bonding enables the formation of a stiffer and more homogenous network.

In another aspect, the anti-inflammatory polysaccharide and gelling polymer can be admixed, and the resulting composition is sheared as described above. In this aspect, the composition of anti-inflammatory polysaccharide and gelling polymer is sheared, filled into a delivery device, packaged and stored frozen. The composition would then be thawed at time of administration.

Preparation of In Situ Gelling Compositions

The anti-inflammatory polysaccharide and gelling polymer can be admixed by any method that is known to one of skill in the art such that the resulting mixture is a liquid solution containing the components therein. The term "admixing" is defined as mixing the two components together so that there is no chemical reaction or physical interaction. The term "admixing" also includes the chemical reaction or physical interaction between the two components. Third, electrostatic interactions, hydrophobic interactions, or physical entrapment can occur between the two components.

Typically, the components are admixed in a biocompatible solute or liquid such as, but not limited to, water, saline, phosphate buffered saline, SELP solution, tris(hydroxymethyl)methylamine (Tris), minimum essential medium (MEM) or other buffer, barium contrast, or isotonic aqueous solution. Typically, mixing occurs at temperatures less than 30° C. and most typically at room temperature of about or between about 18° C. to 25° C., but could also be performed at temperatures ranging from 1° C. to 5° C. Gentle mixing is generally desired. For example, the components can be combined at room temperature and the solution gently swirled or inverted periodically for a sufficient time to mix the components. The mixture or combination can be incubated together for at least 10 seconds, 30 seconds, 1 minute, 5 minutes, 10 minutes, 20 minutes, 30 minutes, 40 minutes, 50 minutes, 60 minutes or longer. Generally, incubation and mixing is performed in a sufficient time before the composition acquires a non-liquid form. Alternatively, components may be admixed and the solution frozen using liquid nitrogen, methanol or other volatile organic solvent chilled with dry ice, blast freezer, or other method for freezing liquids. The solution can then be stored at temperatures from −80° C. to −20° C. until use. The solution may then be thawed in saline, water, air, or other medium prior to administration. Exemplary procedures for producing the in situ gelling compositions are provided in the Examples.

In another aspect, the components may be admixed as powers and reconstituted as a solution using, but not limited to, water, saline, phosphate buffered saline, SELP solution, tris(hydroxymethyl)methylamine (Tris), minimum essential medium (MEM), barium contrast, organic solvents such as mineral oil or DMSO, or other buffer or isotonic aqueous solution. This may occur with a syringe preloaded with the powder mixture being used to draw up a solution prior to administration. Additionally, the powder may be reconstituted in a bowl, jar, vessel, bag, vial, or other container and subsequently loaded into a delivery device. In one aspect, mixing occurs at temperatures less than 30° C., at room temperature of about or between about 18° C. to 25° C., or in the alternative at a temperature ranging from 1° C. to 5° C. Such a device may include, but is not limited to, a catheter, luer-lock syringe, bulb syringe, enema syringe, clyster syringe, "banana bag", "drip bag", tube, dropper, enema bottle, or other device for delivery.

The in situ gelling composition is a liquid at 18 to 23° C. that converts to a hydrogel at 37° C. In one aspect, the composition has a viscosity of less than or equal to 2,500 cP, less than or equal to 2,000 cP, less than or equal to 1,500 cP, less than or equal to 1,000 cP, or less than or equal to 700 cP at 18 to 23° C. Due to the fact that composition is a liquid at 18 to 23° C., it can be injected using techniques known in the art.

In one aspect, when the gelling polymer is a SELP, the SELP is present in the composition at a weight percentage (wt %) of the in situ gelling composition of from 2% (w/w) to about 20% (w/w), from 2% (w/w) to 18% (w/w), from 2% (w/w) to 16% (w/w), from 2% (w/w) to 14% (w/w), from 2% (w/w) to 12% (w/w), from 4% (w/w) to 12% w/w, from 6% (w/w) to 12%, from 8% (w/w) to 12% (w/w), or from about 10% (w/w) to 12% (w/w). For example, the SELP is present in the in situ gelling composition at a weight percentage (wt %) of the composition of from 4%, 5%, 6%, 7%, 8%, 9%, 10%, 11%, 12%, 13%, 14%, 15% or 20% (w/w).

It will be appreciated that the actual preferred amounts of the anti-inflammatory polysaccharide in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

In one aspect, the concentration of the anti-inflammatory polysaccharide within the in situ gelling composition can modify gelation kinetics, viscosity, and final modulus. In one aspect, when the anti-inflammatory polysaccharide is a sulfated hyaluronan (SAGE), the SAGE is at a weight percentage (wt %) of the in situ gelling composition of from 0.01% (w/w) to about 20% (w/w), 1% (w/w) to about 20% (w/w), from 0.01% (w/w) to 0.1% (w/w), from 0.01% (w/w) to 0.5% (w/w), from 0.01% (w/w) to 1% (w/w), from 0.01% (w/w) to 2% (w/w), from 0.01% (w/w) to 5% (w/w), from 0.01% (w/w) to 10% (w/w), from 1% (w/w) to 5% (w/w), from 1% (w/w) to 10% w/w, from 1% (w/w) to 12%, from 5% (w/w) to 15% (w/w), or from about 5% (w/w) to 20% (w/w) can be used herein. For example, the SAGE is present in the in situ gelling composition at a weight percentage (wt %) of the composition of from 0.01%, 0.1%, 0.5% 1%, 2%, 3%, 4%, 5%, 6%, 7%, 8%, 9%, 10%, 11%, 12%, 13%, 14%, 15% or 20% (w/w), while the in situ gelling polymer may comprise from 1% to 20% of the remaining solution.

The in situ gelling compositions can also include one or more active ingredients used in combination with the in situ gelling compositions described herein. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the compounds described herein can contain combinations of two or more pharmaceutically-acceptable compounds. Examples of such compounds include, but are not limited to, further comprises an antioxidant (e.g., vitamin E), a mucoadhesive agent, an anti-inflammatory agent, an anti-pyretic agent, steroidal and non-steroidal drugs for anti-inflammatory use, a hormone, a growth factor, a contraceptive agent, an antiviral, an antibacterial, an antifungal, an analgesics, a hypnotic, a sedative, a tranquilizer, an anti-convulsant, a muscle relaxant, a local anesthetic, an antispasmodic, an antiulcer drug, a peptidic agonist, a sympathiomimetic agent, a cardiovascular agent, an antitumor agent, or an oligonucleotide.

In other aspects, the in situ gelling compositions can include a contrast agent that can be detected using techniques known in the art. Here, the contrast agent can be used to observe the location and duration of the gel once administered to the subject.

The in situ gelling composition, or components thereof, can be packaged as kits for preparing the composition. For example, the kit can include an anti-inflammatory polysaccharide and a gelling polymer. The kits can optionally include one or more components such as instructions for preparation and use, devices and additional reagents, and components, such as tubes, containers, syringes and other devices for delivering the composition to the subject. For example, the kit also can contain an aqueous solution such as a solvent or buffer for suspending or dissolving the components.

Applications of In Situ Gelling Compositions

The in situ gelling compositions described herein are liquids at room temperature but convert to hydrogels upon administration to the subject. The in situ gelling compositions are very useful in treating and/or prevention of inflammation in a subject where the liquid in situ gelling composition can be readily administered to a subject. For example, in situ gelling composition can be administered intravenously, intramuscularly, transmucosally, or subcutaneously. In other aspects, the in situ gelling composition is applied to a mucosal tissue or membrane in the subject. Thus, in one aspect, the in situ gelling composition can be administered ophthalmically, vaginally, rectally, intranasally, or applied directly to the oral mucosa, gingival, or periodontal pocket.

The in situ gelling compositions described herein can be administered in a number of ways depending on whether local or systemic treatment is desired, and on the area to be treated. When the in situ gelling composition is to be administered to a subject as a liquid, the composition can be formulated with sterile aqueous or non-aqueous solutions, suspensions, and emulsions. Examples of aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. In the case when in situ gelling composition is administered as a liquid, the composition can be administered by a syringe (with or without a needle), enema, catheter, or bulb syringe.

In other aspects, the in situ gelling composition can be formulated in a number of different formulations depending upon the application of the in situ gelling composition (e.g., ophthalmic, vaginal, rectal, intranasal, oral, or directly to the skin). The in situ gelling composition can be formulated as an ointment, lotion, cream, gel, drops, suppositories, sprays, liquids, powders, or an aerosol or dry micronized powder for inhalation. Conventional pharmaceutical carriers, aqueous, powder or oily bases, thickeners and the like can be necessary or desirable.

The in situ gelling composition is useful in treating and/or preventing inflammation in a body cavity of a subject where the composition can be introduced into the cavity. In one aspect, the in situ gelling composition is useful in treating and/or preventing inflammation in the rectum of a subject. One source of inflammation in the rectum is radiation-induced proctitis (RIP). RIP is the most common clinical issue for patients receiving radiotherapy as part of the standard course of treatment for ovarian, prostate, colon, and bladder cancers. RIP limits radiation dosages, interrupts treatment, and reduces patient quality of life. More than 200,000 cancer patients receive abdominal or pelvic radiation therapy annually, and the number of cancer survivors with post-radiation intestinal dysfunction continues to grow. Acute RIP occurs in greater than 75% of patients receiving radiotherapy for prostate cancer and progresses to debilitating chronic RIP in 5-10% of cases. RIP is manifested by bleeding, pain, abdominal cramping, mucoid discharge, diarrhea, fecal urgency, and tenesmus.

During radiotherapy for prostate, cervical, ovarian, and bladder cancer, portions of the colon and rectum often fall within the radiation field due to anatomical proximity. Even with image-guided placement of the beams and protective shielding, irradiation of the cancerous tissue without also irradiating the rectum or other sensitive organs is not feasible.

The exact etiology and pathophysiology of RIP is not completely understood, but it is widely accepted that radiation-induced damage to lipids and DNA triggers mucosal atrophy, submucosal edema, and inflammation that cause RIP. Symptoms of RIP can emerge immediately or months after radiotherapy and can persist for 20 years post-diagnosis. Chronic RIP can lead to life-threatening complications including fistula formation, sepsis, perforation, and internal bleeding.

A prophylactic treatment that protects the gastrointestinal tract from the deleterious effects of radiotherapy would improve patient quality of life during and after treatment and would allow for higher doses of radiation to be administered more regularly, leading to improved clinical outcomes. No effective clinical prophylactic treatment options exist for the prevention of RIP in spite of its prevalence and clinical significance. Current treatments for RIP are reactionary and typically administered only after the onset of RIP. Previously investigated treatments such as sucralfate, 5-aminosalicylic acid, short-chain fatty acids, sodium butyrate, hydrocortisone, vitamin E, epinephrine, hyaluronic acid, and topical application of formalin frequently fail to make significant improvement in patient quality of life and have even been shown to exacerbate the disease in rare cases. After the failure of pharmacological treatments, physicians utilize surgical interventions, including laser ablation, electrocauterization, sclerotic injections, argon plasma coagulation, and radiofrequency ablation, all of which carry significant risks of morbidity and mortality. These surgical interventions frequently increase rectal pain, diarrhea, tenesmus, ulcers, fistula, rectal stenosis, and anal strictures. The in situ gelling compositions described herein provide a much needed solution to this long-standing problem.

In addition to treating and/preventing inflammation in the rectum, the in situ gelling compositions described herein are useful in other applications as well. The in situ gelling compositions can be used in a variety of applications related to the treatment and/or prevention of inflammatory skin disorders, dental disorders, respiratory disorders, inflammatory eye disorders, burn injury healing, and tissue regeneration/engineering. In one aspect, the in situ gelling compositions can improve wound healing in a subject in need of such improvement. The in situ gelling compositions can be placed directly in or on any biological system. Examples of sites the partially sulfated hyaluronan can be placed include, but are not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the joint space, the cul-de-sac of the eye, and the like; the peritoneal cavity and organs contained within, and other sites into or onto which the compounds can be placed including a skin surface defect such as a cut, scrape or burn area. It is contemplated that the tissue can be damaged due to injury or a degenerative condition or, in the alternative, the in situ gelling compositions described herein can be applied to undamaged tissue to prevent inflammation and/or injury to the tissue.

In the case of inflammatory skin disorders such as psoriasis, acne, atopic dermatitis, rosacea or UV light dependent photo-aging (i.e., photo-dermal ageing), the in situ gelling composition can be applied topically as part of an emollient to prevent or treat the intended condition. In the case of respiratory disorders such as asthma, chronic obstructive pulmonary disease, acute lung injury or cystic fibrosis, the in situ gelling compositions can be formulated as water-soluble isotonic vehicle compatible with airway lining fluid and delivered to the lung or nasal passages as an inhaled aerosol. Alternatively, the in situ gelling composition can be formulated into a micronized powder and inhaled into the lung as a dry powder. In the case of eye diseases, the in situ gelling composition can be formulated with an aqueous vehicle and applied to the eye topically as drops, or injected directly into the eye either by needle or using an implanted constant drug delivery device. In the case of dental disorders such as periodontal disease, the in situ gelling compositions can be formulated into creams or gingival packing materials to be applied directly to the gingival crevice.

In further aspects, the in situ gelling composition can be used in genitourinary applications (e.g., prevention of urinary tract infection, treatment of the transitional cell cancer of the bladder and uroepithelial system; treatment of interstitial cystitis; and use as a vaginal lubricant/protective to prevent transmission of sexually transmitted diseases). In one aspect, the in situ gelling composition can be administered topically to the vagina in order to reduce or prevent bacterial, fungal, viral or mechanical or biologically-induced inflammation.

In another aspect, the in situ gelling composition can be used to treat a number of respiratory disorders including cystic fibrosis, bronchiectasis, rhinitis (both allergic and perennial), sinusitis, emphysema and chronic bronchitis (COPD), acute lung injury/adult respiratory distress syndrome, interstitial lung fibrosis, SARS, asthma, and respiratory syncytial virus. In other aspects, the partially or fully sulfated hyaluronan can prevent and treat snoring and obstructive sleep apnea, prevent infection by common respiratory pathogens (*Streptococcus pneumoniae, Hemophilus influenzae, Staphylococcus, Mycoplasma pneumoniae, Chlamydial pneumonia*, Gram negative enteric infections) in immune suppressed hosts such as subjects who are HIV positive or who have hematopoietic malignancies, or prevent and treat otitis media.

The in situ gelling composition can be used in cardiovascular applications (e.g., treating or preventing acute coronary syndrome or atherosclerosis); hematological/oncological applications (e.g., prevention and treatment of sickle cell anemia; prevention and treatment of metastatic disease; and prevention of hypercoagulable state of malignancy (Trousseau's syndrome)); treatment of infectious diseases (e.g., cerebral vascular occlusive syndromes and nephritis in *Falciparum* malaria, Yellow fever, Denge fever, systemic sepsis, and adjunctive treatment of HIV to prevent viral fusion with and infection of target cells); treatment of gastrointestinal diseases (e.g., ulcerative colitis, Crohn's disease of the bowel, Hemorrhoids, and the prevention of stress ulceration of the stomach and esophagus); treatment of rheumatological and immunological diseases (e.g., prevention and treatment of osteoarthritis, rheumatoid arthritis, systemic lupus erythematosis, prevention and treatment of angioneurotic edema, Sjogren's syndrome, systemic sclerosis, systemic amyloidosis, and systemic mastocytosis); renal diseases (e.g., prevention and treatment of diabetic nephropathy and glomerulonephritis); and neurologic diseases (e.g., multiple sclerosis and Alzheimer's dementia).

In one aspect, the in situ gelling composition can be used to treat or prevent urological inflammation. The term "urological inflammation" as used herein is defined as inflammation associated with any part or region of the genitourinary system. Urological inflammation includes, but is not limited to, inflammation of the bladder, urethra, urothelium lining, kidney, prostate, vagina, uterus, or any combination thereof. In this aspect, the partially or fully sulfated hyaluronan can be injected parenterally, either intravenously, intramuscularly or subcutaneously, to treat or prevent systemic urological inflammatory disorders. Alternatively, the in situ gelling composition can be administered by intravesical installation (i.e., via a catheter).

In other aspects, in situ gelling composition can be used in ophthalmological applications such as, for example, in the treatment of age-related macular degeneration, diabetic retinopathy, dry eye syndrome and other inflammatory conjunctivitis, iritis, uveitis, allergic conjunctivitis, anti-inflammatory aid in surgery (e.g., cataract surgery), or in the prevention of inflammation and scarring (e.g., corneal). In one aspect, the in situ gelling composition can be administered intraocularly or directly to the surface of the eye.

In other aspects, in situ gelling composition can be used in the treatment and/or prevention of inflammation present in the ear. Thus, the composition can be directly administered into the sinuses or into the outer, middle or inner ear.

The in situ gelling composition can be administered prophylactically either immediately prior to exposing the subject to a source of inflammation and/or tissue damage (e.g., radiation). In one aspect, the in situ gelling composition is administered to the subject from 0.5 to 48 hours prior to exposing the subject to the source of inflammation and/or tissue damage. In addition to addition to be administered to a subject prior to inflammation insult, the in situ gelling composition can be administered prophylactically to the subject after the inflammation insult to prevent or reduce inflammation and/or tissue damage. The prophylactic pretreatment may be supplemented with daily, every other day, or weekly administration after the initial treatment.

The compositions described herein are useful in reducing or preventing tissue damage in a subject. In one aspect, the in situ composition can be administered to a subject prior to exposure to radiation or another source of inflammation in order reduce or prevent damage to a mucosal membrane or epithelium of the subject. In other aspects, the in situ composition can be used to reduce or prevent tissue damage in the thyroid of the subject.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions) can be used to optimize the product purity and yield obtained from the described process. Only reasonable and routine experimentation will be required to optimize such process conditions.

I. Materials and Methods

A. Materials

A silk-elastinlike protein polymer was synthesized with 6 repeats of blocks comprised of 8 silk-like units, 15 elastin-like units, and 1 lysine-substituted elastin-like unit (SELP 815K) according to a previously-published procedure. The SELP 815K was sheared at >17,000 psi to enhance homogeneity and improve material properties. A semi-synthetic glycosaminoglycan construct was generated from the sulfation of hyaluronic acid (GAG GM-0111), a sulfated HA meeting the specifications above and having a degree of sulfation from 3.5-4.0 and molecular size range from 1 kDa to 10 kDa. Poly(ethylene glycol) (PEG)-based suppositories were formulated and used as controls.

B. In Vitro Release

The release of GAG from a SELP matrix was quantified using an Azure A base colorimetric assay. Samples of SELP 12% and GAG-GM-0111 (lyophilized form) were mixed to create a 100 mg/mL GAG in SELP (final SELP concentrations of 4 wt % or 11 wt %) solution and loaded into 500 µL insulin syringes (obtained from Becton Dickenson and Company), and incubated overnight at 37° C. The tip was severed from the syringe and the gel sectioned into 20 µL disks. The masses of the disks were measured and recorded. Samples were placed into test tubes (obtained from Bioexpress) containing 4 mL of simulated intestinal fluid without enzyme (Sigma Aldrich). Samples were incubated in a STEADYSHAKE™ 757 incubator (Amerex Instruments, Inc.) at 37° C. and 175 rpm. At 15 min, 30 min, 1 hr, 2 hr, 3 hr, 12 hr, and 24 hr, 100 µL of release media were combined with 190 µL of 0.025 mg/mL Azure A in a 96-well plate. Absorbance at 620 nm was measured on a Spectramax M2 spectrophotometer (Molecular Devices). The concentration of GAG in the solution was determined from an experimentally-obtained concentration curve.

C. Rheology

Rheological testing was performed using an AR550-Stress Controlled Rheometer (New Castle, Del.). A cone-and-plate configuration with a 20 mm 4° cone geometry was used. An aluminum cover and mineral oil (Sigma Aldrich) were used to seal the environment and prevent dehydration of the samples during testing. Viscosity was measured from 18 to 37° C. (5.76° C./min) using an oscillatory procedure at an angular frequency of 6.283 rad/s. This was immediately followed by a 3 hr oscillatory sweep at 37° C. using 0.1% strain and an angular frequency of 6.283 rad/s. Samples were prepared by thawing flash-frozen 12 wt % SELP solutions in room temperature water. The SELP was diluted with chilled solutions of phosphate buffered saline (PBS) containing GAG GM-0111 to achieve final concentrations of 4 wt % or 11 wt % SELP-815K and 100 mg/mL GAG GM-0111. All tests were performed in triplicate using separately prepared samples.

D. Scanning Electron Microscopy

Samples of the hydrogel matrices were examined using scanning electron microscopy performed on an FEI Quanta 600F. Samples were prepared from the same hydrogels used in Example I.B. and flash frozen in liquid nitrogen and then lyophilized on a FreeZone 12 (Labconco) at ≤−50° C. and ≤mBar for 4 days. The lyophilized disks were mounted onto carbon tape and sputter coated with a 5 nm layer of gold palladium (Gatan 682 precision etching coating system) prior to imaging. Images were acquired using secondary electrons at 1000× magnification.

E. In Vivo Accumulation

The accumulation of GAG GM-0111 within the rectum was evaluated by fluorescence microscopy. GAG GM-0111 was fluorescently labeled with ALEXA FLUOR®-633 (Thermo-Fisher Scientific) according to a published procedure. The labeled GAG GM-0111-Alexa633 was combined with non-labeled GAG at a ratio of 1:3 to generate sufficient material for the study. The GAG GM-0111-Alexa633 was combined with SELP immediately prior to administration. Female BDF-1 mice of 8-10 weeks in age were randomly assigned into three experimental arms (n=6) GAG GM-0111-Alexa633 at 100 mg/mL in PBS, GAG GM-0111-Alexa633 at 100 mg/mL in an 11 wt % SELP 815K solution, and unlabeled GAG GM-0111 in an 11 wt % SELP-815K solution to serve as an auto fluorescence control. Mice were anesthetized with 600 µL of a 1.2% solution made from 2,2,2-tribromoethanol (Sigma Aldrich) and 2-methyl-2-butanol, tertiary amyl alcohol >99% (Sigma Aldrich) injected intraperitoneally. After anesthetization, a SILASTIC® 0.94 mm outer diameter, 0.51 mm inner diameter catheter (Dow Corning) was gently inserted 4 cm through the anus into the rectum of the mice. As the catheter was slowly withdrawn, 80-100 µL of the enema solution was injected and the animals were placed supine in their cages to recover. The mice were sacrificed at either 3 hr or 12 hr after the treatment was administered.

At necropsy, 1.5 cm of rectum was removed and fixed in 10% formalin (Ted Pella, CA) overnight at 4° C. The tissue was then stained with Hoechst 33342b (Invitrogen) per the manufacturer's protocol. Standard dehydration methods were then used, employing serially increasing concentrations of ethanol (70%, 95%, 100%) and xylene. The fixed tissues were then embedded into paraffin blocks and sectioned into 0.5 µm thick slices. The samples were imaged on an Olympux BS40 fluoro-microscope via an Infinity 3 amera (Lumenear Corp., Ottawa, Canada) at 350±15 nm excitation and 460±15 nm emission for Hoechst 33342 and 640±15 nm excitation and 690±15 nm emission for Alexa 633. The images were then composited in Infinity Analyze software (Lumenear Corp., Ottawa, Canada).

F. In Vivo Efficacy

The efficacy of the SELP/GAG system was evaluated in a murine model of radiation-induced proctitis. FIG. 1 shows a schematic of an experimental treatment protocol in which mice are injected rectally with a solution of silk-elastin like protein polymer (SELP 815K) and semi-synthetic glycosaminoglycan (GM-0111) prior to treatment of the lower abdomen with radiation. The administration of this SELP 815K/GM-0111 enema protects the rectum from radiation-induced damage.

Female BDF-1 mice of 8-10 weeks in age were randomly assigned into 4 groups (n=18): no treatment control, 100 mg/mL GAG GM-0111 in phosphate buffered saline (PBS), SELP 815K 11 wt % sheared, and SELP 815K 11 wt % with 100 mg/mL GAG GM-0111.

Within each treatment group, animals were designated for sacrifice after 3, 7, or 21 days (n=6). The treatments were administered as described in Example I.E. Mice were then affixed to a steel plate in a supine position and a 6.35 mm thick lead plate with 1 cm by 4 cm windows was positioned such that the windows extended from the anus along the median plane of the mice, limiting the radiation exposure to just the lower abdomen. The mice were then placed in an RS 2000 X-Ray Irradiator (RAD SOURCE Technologies, GA, USA) set to level 3 for 16 min, 17 sec to receive 35 Gy of radiation. Following the procedure, mice were returned to their enclosures.

G. Behavioral Pain Assessment

The pain response of the mice was behaviorally assessed prior to treatment and prior to sacrifice on days 3, 7, and 21. The mice were placed into individual enclosures composed of a wire mesh floor and clear polycarbonate sides and allowed to acclimatize for at least 10 min prior to testing.

The degree of referred hyperalgesia and tactile allodynia were assessed using von Frey filaments corresponding to 0.04, 0.16, 0.4, 1, and 4 g, according to previously published protocols. The lower abdomen of each mouse was stimulated with each filament for approximately 1 second with at least 3 seconds between 10 successive tests. Care was taken to ensure that each stimulus was in a distinct location from previous stimuli to avoid pain wind-up effects. A sharp retraction of the abdomen, immediate licking or scratching of the stimulated area, or a jump was considered a positive indication of pain.

The response rate was taken as the proportion of positive indications out of 10 stimulations. The percent reduction of pain response for each treatment group was calculated from the average percent change of all 5 stimulus levels compared to the no treatment control.

H. Tissue Collection and Histology

Tissue was collected and fixed as described in Example I.E. Samples were then washed with distilled water and stained with hematoxylin solution (Ricca Chemical Company, TX, USA) for 45 seconds and rinsed for 5 minutes with running DI water. The samples were then rinsed with 95% ethanol (Decon Labs Corp., MA, USA) and counterstained with eosin solution for 1 min, 30 sec, dehydrated, embedded in paraffin blocks, and sectioned as described in Example I.E.

I. Statistical Analysis

A one-way paired student's T-test was used to compute statistical significance between samples and controls. A two-way ANOVA with a Bonferroni post-test was used to assess the significance of data containing greater than two experimental groups for comparison. Graphs and charts were created in GraphPad Prism (GraphPad Software, Inc., La Jolla, Calif., USA). All data is reported as the mean±standard deviation unless otherwise specified. A value of p≤0.05 (*) was considered statistically significant, p≤0.01 () highly significant, and p≤0.0001 (*) very highly significant.

J. Fabrication of GAG-Embedded SELF Hydrogels for Imaging and Release

Samples were fabricated to evaluate the effect of SELP concentration and shear processing on the release of GAG GM-0111. SELP 815K 12% (w/v) in phosphate buffered saline (PBS) was sheared at >17,000 psi as described in Price, R., Poursaid, A., Cappello, J. & Ghandehari, H. Effect of shear on physicochemical properties of matrix metalloproteinase responsive silk-elastinlike hydrogels. *J. Control. Release* 195, 92-98 (2014). Material from the same batch that was not subjected to shear processing was used to fabricate samples with unsheared SELP.

Syringes were prepared with homogeneous solutions of sheared and unsheared SELP 815K combined with GAG GM-0111 and PBS comprising 100 mg/mL GAG GM-0111 and 4 wt % or 11 wt % SELP 815K. The samples were then incubated overnight at 37° C.

II. Results

A. Characterization of Sheared Hydrogels

Figure 2:
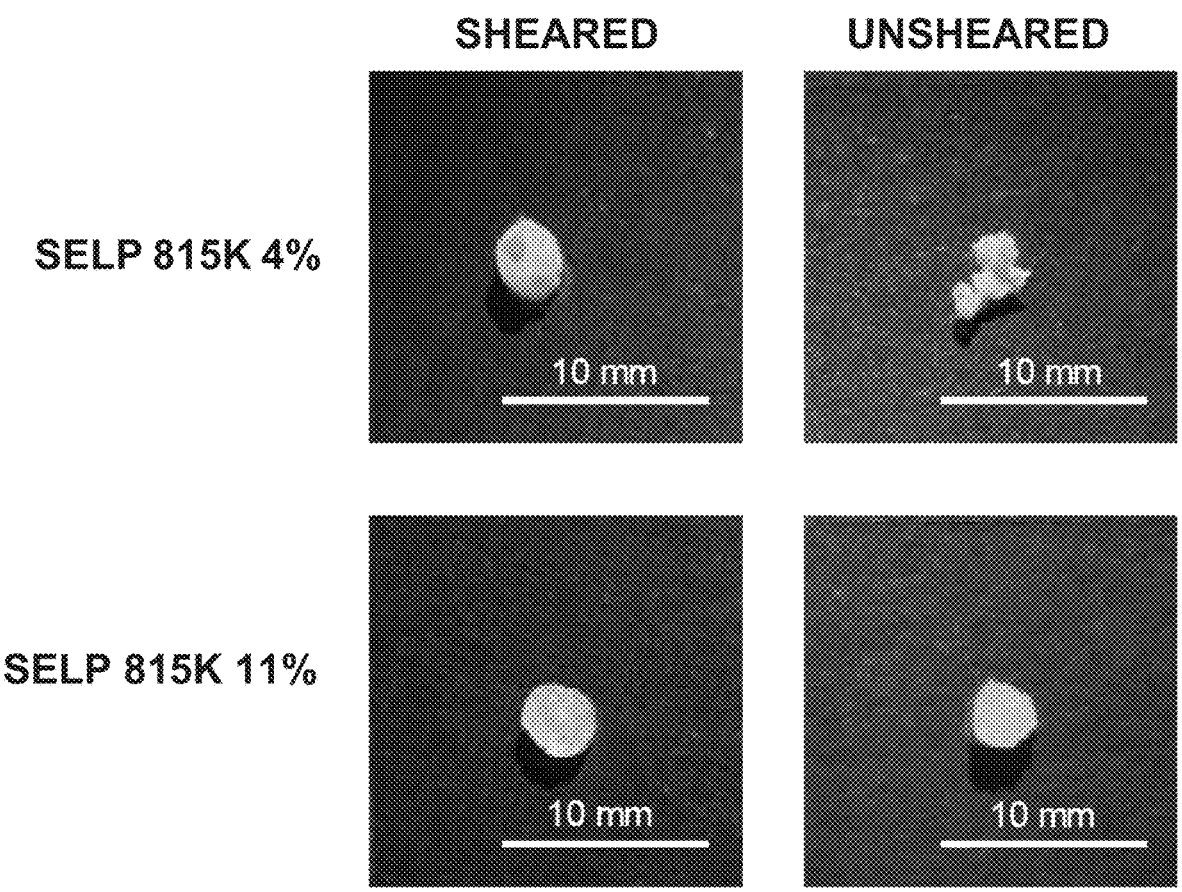
FIG. 2 shows scanning electron micrographs of SELP 815K gels. Unsheared SELP 815K (right-hand photos, top and bottom) at two different weight percentages did not produce consistent samples due to phase separation during curing. Sheared SELP 815K gels (left-hand photos, top and bottom) at two different weight percentages formed consistent gels without macroscopic phase separation.

Unsheared SELP 815K formed two distinct layers within a syringe, one a liquid and the other a gel. Sheared SELP 815K formed a single phase solid gel matrix. For analysis, gel specimens were sectioned into 20 µL disks. For unsheared specimens, the liquid phase was removed and the gel portion was analyzed (FIG. 2). Scanning electron microscopy as previously described was used to image the sheared and unsheared hydrogels.

Figure 3:
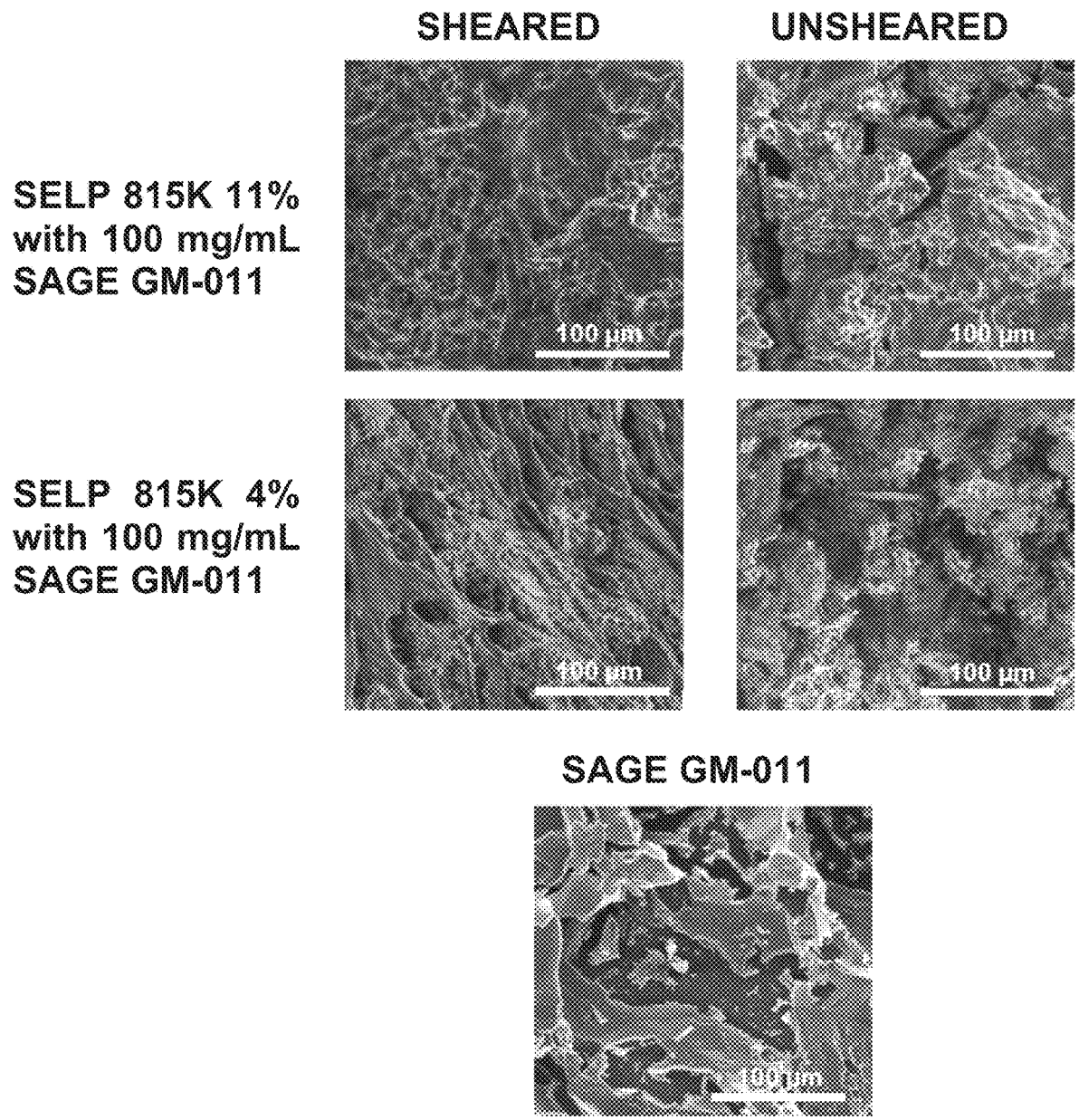
FIG. 3 shows SEM micrographs of SELP 815K gels containing GAG GM-0111. GAG on its own formed a thin, flaky film. The sheared SELP 815K gels formed fibrous networks with GAG films interpenetrating within the SELP. When the SELP was not sheared, deep cracks and pitting were observed and the fibers tended to form a less homogeneous matrix with interspersed zones of high fiber density.

SEM images of the gels showed higher density fiber networks in the SELP 11 wt % solutions compared to the SELP 4 wt % solutions, consistent with the notion that the fiber network was composed of SELP. The GAG formed localized deposits interspersed within the fibrous network of the SELP hydrogels in similar fashions among the various groups. Deep fissures and cracks were observed in the unsheared SELP samples but not within the sheared samples (FIG. 3). Due to the observed phase separation and mechanical instability, the unsheared samples were not tested further.

B. In Vitro Release of GAG from SELP 815K Matrices

Figure 4:
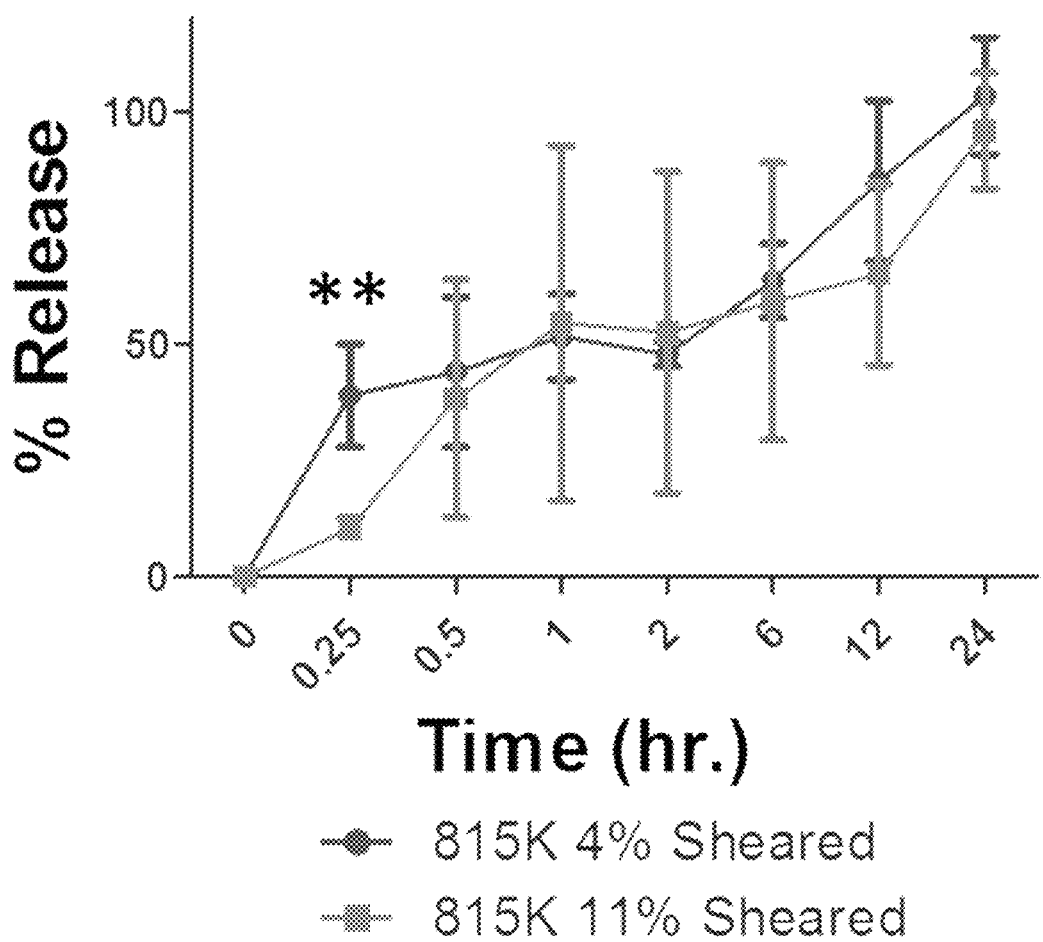
FIG. 4 shows release of GAG GM-0111 from SELP 815K hydrogels. Increasing the concentration of SELP 815K reduced the burst release of GAG GM-0111 from hydrogels upon initial administration. Both 4% and 11% SELP 815K gels release their entire payloads within 24 hours in simulated intestinal fluid. (** indicates $p<0.01$.)

Release testing was carried out using gels produced with sheared 11 wt % and 4 wt % SELP 815K and 100 mg/mL GAG GM-0111. The 4 wt % gel released 39±11% (n=3) while the 11 wt % gels released only 10±2% (n=4) after 15 minutes (p<0.01). In spite of the higher burst release from the 4 wt % gel, the 4 wt % and 11 wt % gels released 51±9% and 54±38%, respectively, after 1 hr (FIG. 4). Within 24 hr there was complete release of GAG from both the 11 wt % and 4 wt % hydrogels. No statistical difference was observed between the 11 wt % and 4 wt % groups after the 15 min time point, indicating that varying the concentration of SELP impacts only the initial burst release of GAG from the matrix, not the timing of total cumulative release.

C. Rheological Evaluation of In Situ Gelling SELF Formulations

To determine the injectability of the in situ gelling system, solution viscosities were measured from 18 to 37° C. The sheared 4 wt % SELP 815K and 11 wt % SELP 815K with 100 mg/mL of GAG were selected for rheological evaluation and compared to sheared SELP 815K at 4 wt % and 11 wt % without GAG, GAG dissolved in PBS at 100 mg/mL, and a PEG suppository. Flash frozen liquid stocks of sheared SELP 815K were used for the production of each sample. After thawing, the SELP 815K was combined with GAG GM-0111 to create the 4 wt % and 11 wt % SELP 815K solutions.

Figures 5A, 5B, 5C:
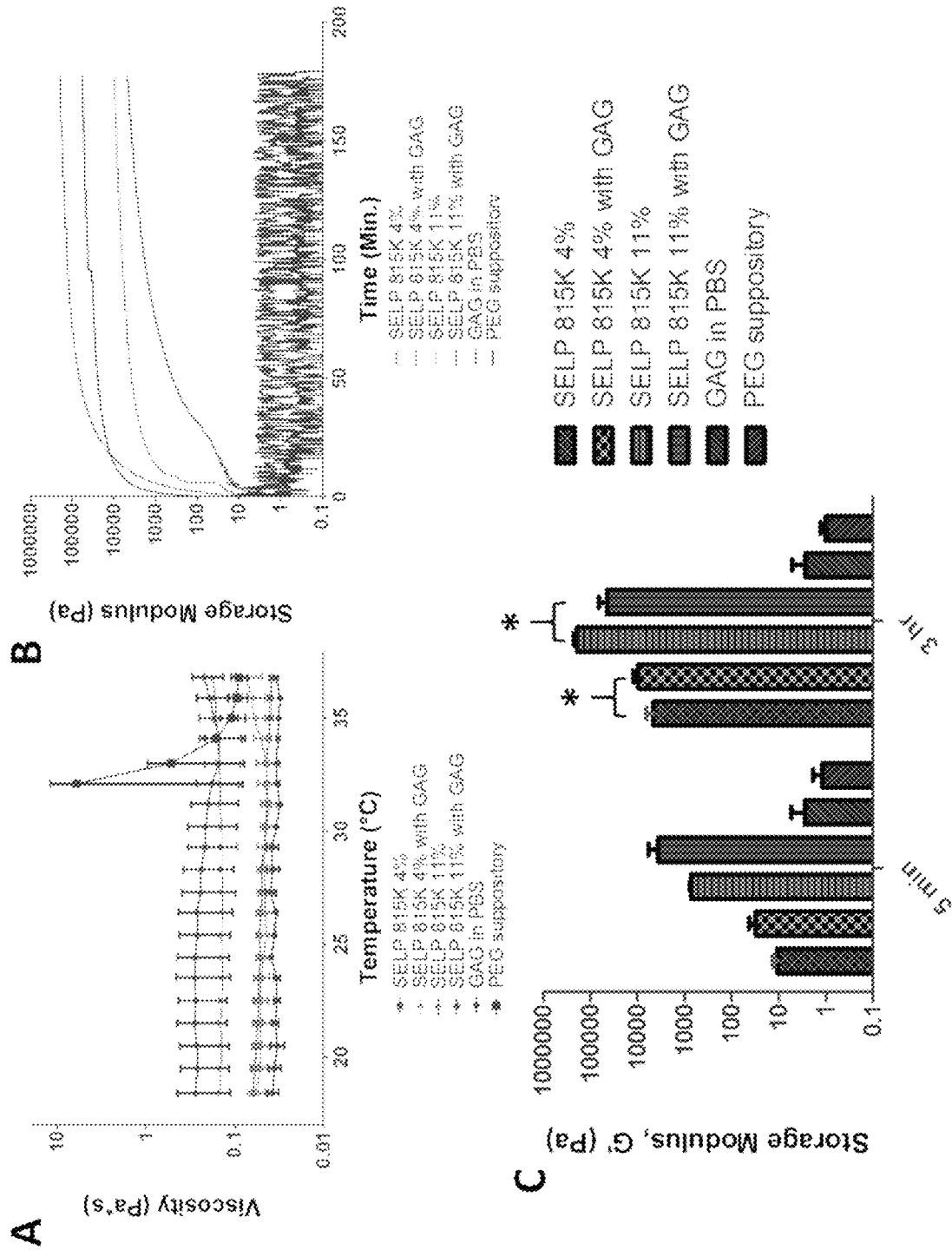
FIG. 5A shows viscosity curves from 18 to 37° C.
FIG. 5B shows a plot of the mean storage modulus (n=3) as an indication of gel stiffness for each of the treatment groups over a 3 hour period.
FIG. 5C shows the storage modulus at 5 min as an indicator of gelation rate and at 3 hr as an indicator of peak stiffness. All vertical axes are on a log scale.

The addition of GAG to the SELP 11 wt % solution increased the viscosity at 25° C. from 140±10 cP with SELP alone to 380±250 cP. In the 4 wt % SELP samples at 25° C., the viscosity changed from 53±6 cP to 44±16 cP. Even though the same amount of GAG was added to both the 11 wt % and 4 wt % SELP solutions, only the 11 wt % SELP solution increased substantially in viscosity. Even so, the observed viscosities of all solutions were within a range that could be easily administered by hand from typical enema administration devices. An upward trend in the viscosity of the SELP solutions was observed as the temperature increased above 33° C., consistent with an SELP response to temperature (FIG. 5A). However, this trend was only statistically significant between 25° C. and 37° C. for SELP 815K 11 wt % (p=0.002). The PEG suppository was solid until melting at 32-34° C. (FIG. 5A). After melting, the viscosity of the PEG suppository at 37° C., 90±27 cP, was less than either the viscosity of the SELP 815K 11 wt % or 4 wt % at 25° C., but still nearly three times as viscous as the GAG in PBS, which was 34±3 cP.

The transition from polymer solution to a three dimensional polymer network was evaluated rheologically using an oscillatory time sweep at 37° C. One way to define the gelation point is the time at which the storage modulus (G') exceeds the loss modulus (G"). All SELP containing solutions achieved a G'>G" within 5 minutes of the start of the time sweep. This was not true for either the PEG suppository or the GAG dissolved in PBS, which exhibited a G">G' at 37° C. throughout the entire 3 hour sweep.

The addition of GAG GM-0111 to SELP 815K accelerated the solution-gel transition and increased mechanical stiffness at the 5 min time point (FIG. 5C). After 5 min at 37° C., SELP 815K 4 wt % and SELP 815K 11 wt % solutions with GAG had 3-fold and 5-fold greater stiffness, respectively, than the SELP solutions without GAG. The modulus continued to rise for the SELP gels (p<0.05 for both the 4 wt % and 11 wt % SELP solutions). However, at 3 hr, GAG had different effects on the storage modulus of the solutions. GAG decreased the stiffness of the 11 wt % SELP 815K solution by 76.8% (p<0.05) but increased the stiffness of the 4 wt % SELP 815K solution by 212% (p<0.05). Both GAG in PBS and the PEG suppository maintained their liquid states, G'<G", throughout the 37° C. sweep (FIG. 5C) and had storage moduli of 3±4 Pa and 1.0±0.4 Pa, respectively.

D. GAG Accumulation in Colorectal Tissue

To evaluate the accumulation of GAG within the rectum, fluorescently-labeled GAG was administered in two enema formulations, one representing a standard enema (PBS) and the other the in situ gelling enema (SELP enema) system. Large dark blue streaks were observed in the bedding material in treatment groups that received the GAG-GM-0111-Alexa633 in PBS 3 hours after administration. Similar streaking was not observed in groups receiving the SELP enema. During necropsy, half of the mice treated with SELP enemas still had visible SELP gels within their rectums. There was no observable retention of SELP gels at 12 hours.

Figure 6:
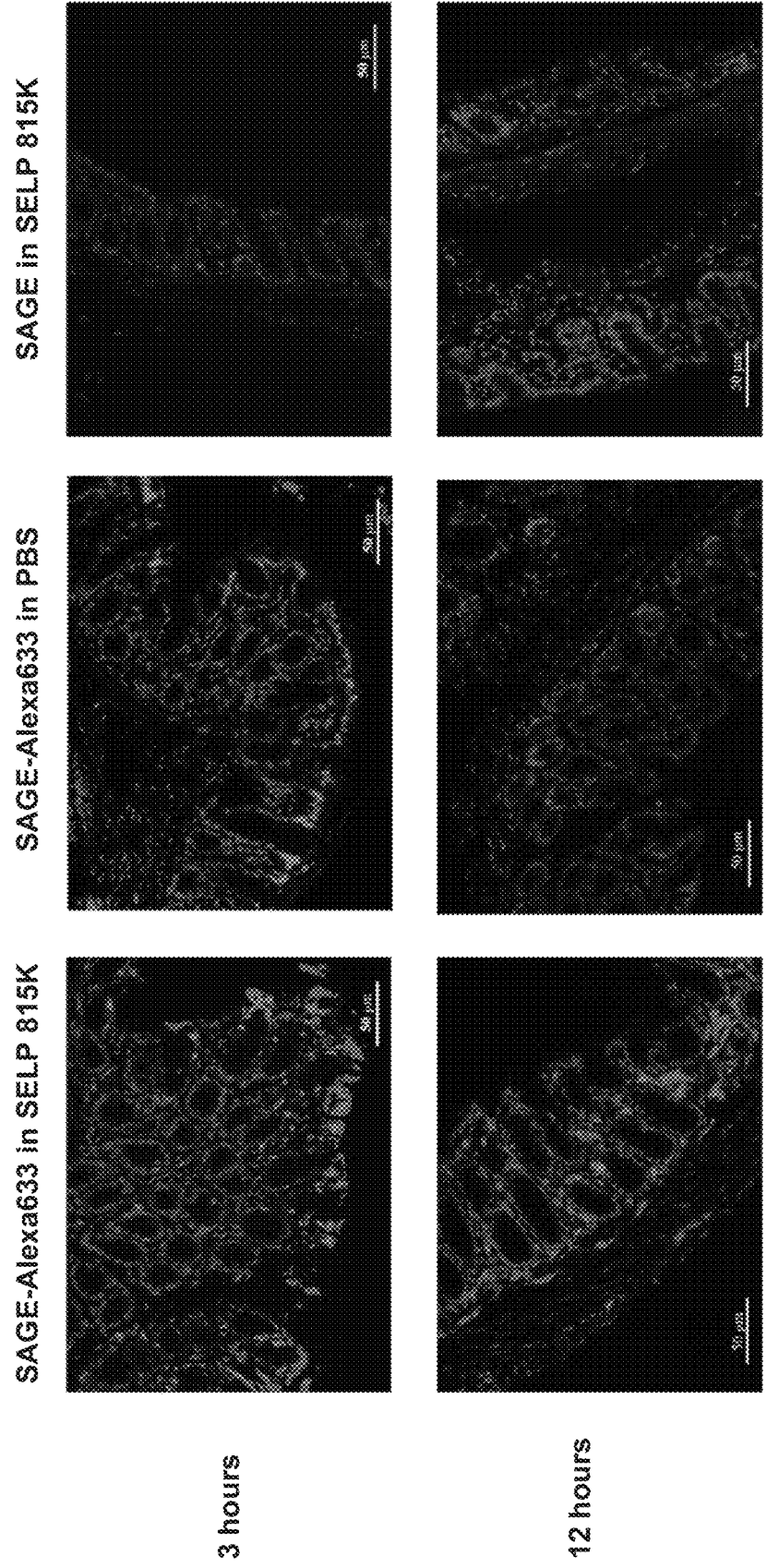
FIG. 6 shows representative fluorescence micrographs of rectal tissue samples. GAG accumulation is enhanced when delivered via a SELP matrix after 3 hours (left) compared to when delivered in phosphate buffered saline (PBS, center). An autofluorescent control is shown on the right. A GAG-Alexa633 construct is shown in red, while rectal tissue stained with Hoechst 33342 is shown in blue. The large amount of GAG in the leftmost images is an indication of enhanced accumulation due to administration with SELP 815K at 11 wt %.

After histological preparation and staining with Hoechst 33342, the tissue samples were fluorescently imaged at 200× magnification for both Alexa 633 (shown in red in FIG. 6) and Hoechst 33342 (shown in blue in FIG. 6). All animals showed substantially greater accumulation of GAG-GM-0111-Alexa633 in the rectum when they received the SELP 815K 11 wt % enema compared to the PBS enema. After 12 hours, no SELP gels were observed in any of the tissues, consistent with SELP elimination from the bowels.

Fluorescent evaluation of the tissues harvested 12 hours post-administration showed significant amounts of GAG-GM-0111-Alexa633 remained in the tissue and had migrated further along the crypts of Lieberkühn all the way to the muscularis mucosae. This penetration was greater than observed for the GAG-GM-0111-Alexa633 administered in the SELP enema at 3 hours, indicating continued penetration. In the animals that received the PBS enema, no fluorescent indication of GAG-GM-0111-Alexa633 was observed at 12 hr. SELP 815K 11 wt % increased the accumulation of GAG-GM-0111 in the walls of the rectum and prolonged its residence time compared to a PBS enema.

E. In Vivo Pain Response

Figure 7:
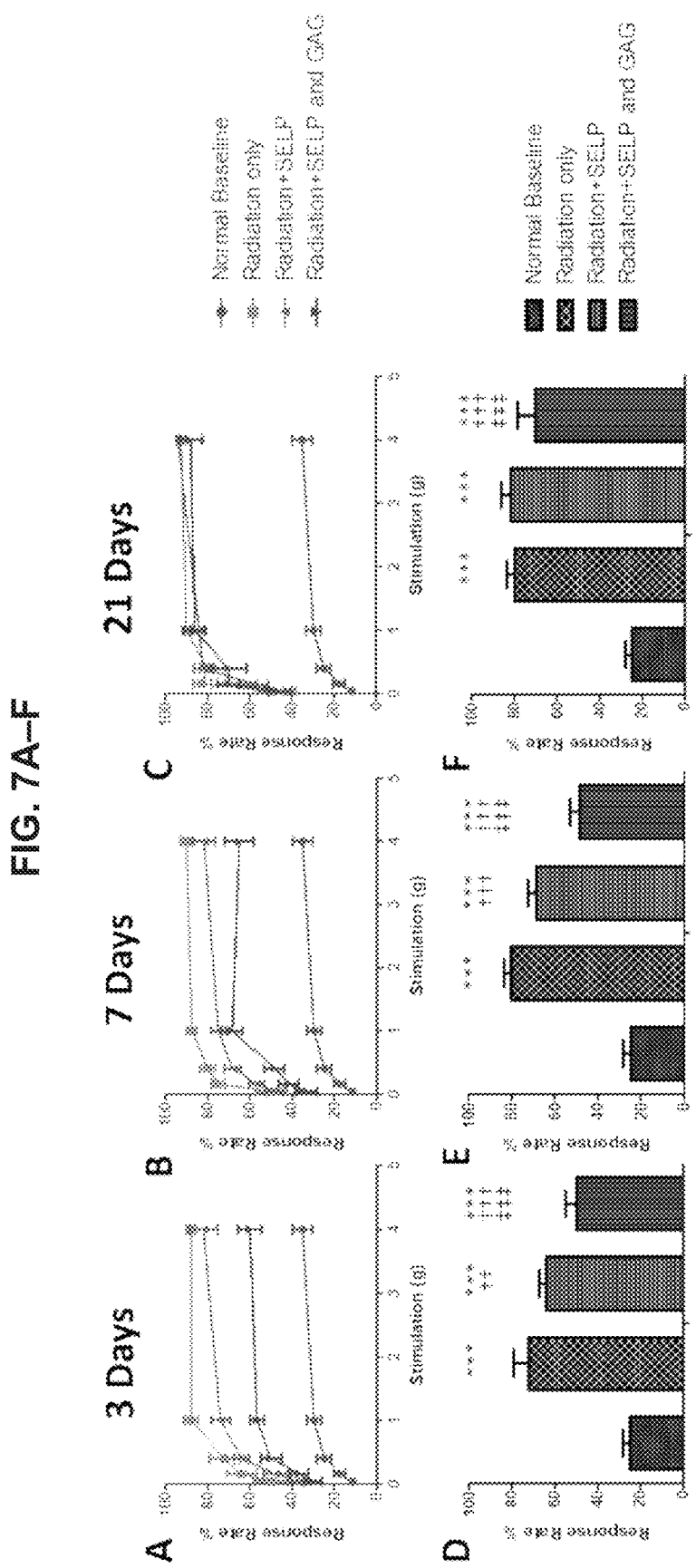
FIG. 7 shows attenuation of pain response by SELP and GAG in an in vivo radiation-induced proctitis mouse model. The left-hand column shows mean response rates of mice to 0.04, 0.16, 0.4, 1, and 4 g von Frey filaments after 3, 7, and 21 days. The right-hand column shows response rate at 0.4 g of force for three different treatment groups (radiation only, radiation+SELP, and radiation+SELP and GAG). The normal baseline is composed of all the pretreatment tests for mice used in each of the treatment groups (n=36). Exposure to radiation sensitized the animals to pain (***, highly statistically significant at $p<0.001$). SELP significantly reduced the pain sensitization of animals exposed to 35 Gy of radiation. SELP alone (see right-hand column) significantly reduced the pain sensitization due to radiation at 3 and 7 days but offered no amelioration at day 21 ($\dagger\dagger^\vartheta$, highly significant at $p<0.01$ at d days, $\dagger\dagger\dagger$, very highly significant at $p<0.001$ at 7 days). The addition of GAG to the SELP improved the efficacy of treatment ($\ddagger\ddagger\ddagger$, very highly significant at 3, 7, and 21 days) and prolonged the efficacy to include the 21-day animals ($\dagger\dagger\dagger$, very highly significant at $p<0.001$).

To evaluate the ability of GAG and SELP enemas to alleviate pain, a mechanosensitivity-based assay using von Frey filaments was employed. An increased response rate at lower stimulation was indicative of increased hyperalgesia and malaise in mice. Baseline measurements were acquired for all the mice in the study and were used to establish a baseline response pattern. Filaments corresponding to 0.04 to 4 g were tested, but the filaments from 0.04 to 0.4 showed the greatest dynamic response as indicated by the slope seen between successive points (FIG. 7). For this reason, the response rate at 0.4 g stimulation was chosen for comparative treatments.

Radiation drastically sensitized the lower abdomen of the mice. At 0.4 g stimulus, the response rate of mice 3 days after receiving 35 Gy of radiation to the lower abdomen quadrupled from 18±3% to 72±7% ($p<0.0001$). After 7 and 21 days, the response rate rose to 80±4%. An even more profound change was observed at 0.04 g of stimulus where the mice became 8.3 times more sensitive after radiation (see orange traces in FIG. 7). These results indicate that the mice developed acute radiation-induced sensitization to mechanical stimuli, such as is observed with the onset of RIP.

GAG GM-0111 and SELP 815K enema reduced the pain response in mice exposed to 35 Gy of ionizing radiation. SELP 815K 11 wt % with and without GAG reduced the response rate at 0.4 g of stimulus from 72±7% to 48±5% and 65±3%, respectively ($p<0.001$ for SELP with GAG and $p<0.01$ for SELP without GAG) 3 days after treatment. The mean inhibition of the pain response was 53±4% for SELP with GAG and 24±10% for SELP alone ($p<0.001$).

Again, after 7 days, both SELP 815K and SELP 815K with GAG achieved significant reduction in response rate compared to the radiation only group ($p<0.001$), with average inhibition of pain response being 19±10% and 48±10%, respectively ($p<0.001$). The addition of GAG to the SELP significantly enhanced the therapeutic outcome compared to SELP alone ($p<0.01$).

After 21 days, the SELP only treatment group was not statistically different from the radiation treatment group, while the SELP and GAG combination still inhibited the pain response by 12±6% (average of all 5 stimulus levels). However, at least during this 21-day observation period, none of the treatments were able to restore the response rate to the levels observed in healthy mice (FIG. 7).

F. Histology

Figure 8:
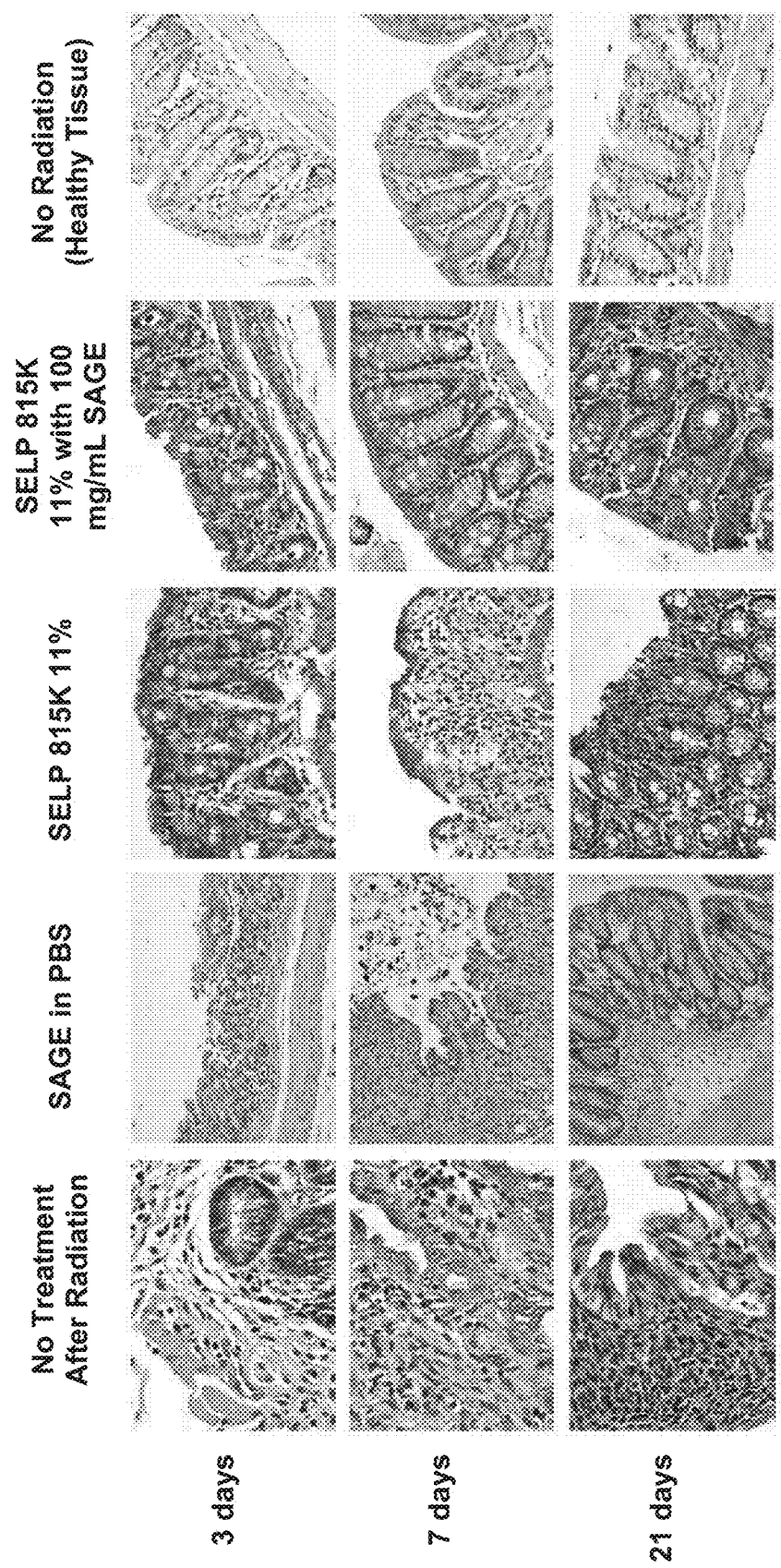
FIG. 8 displays light micrographs of representative tissue samples showing the epithelium of the rectum. Histological tissue samples were stained via hematoxylin and eosin (H & E). The "no treatment" animal shows complete breakdown of the crypts of Lieberkühn and lamina propria. GAG at 100 mg/mL in phosphate buffered saline (PBS) provided no discernible advantage over the "no treatment" group at 3 and 7 days. SELP alone provided some protection at 3 days, but no discernible advantage at 7 days. SELP with 100 mg/mL GAG displayed a protective effect as indicated by near normal histology at both 3 and 7 days. Edema was noted in all groups that received radiation.

To test the hypothesis that GAG delivered from the SELP hydrogel can protect rectal tissue from radiation damage, the following four groups were examined: (1) no GAG and no SELP (control), (2) GAG in PBS, (3) SELP alone, and (4) GAG in SELP. The GAG concentration was 100 mg/mL in all applicable groups. Indications of radiation-induced damage to the rectum include damage to the epithelial layer, mitotic arrest, damage to the crypts of Lieberkühn, damage to the mucosa, and inflammation (FIG. 8). 35 Gy radiation caused substantial damage to the rectum. This was demonstrated by the breakdown of the epithelial layer observed at days 3 and 7. The crypts of Lieberkühn and goblet cells were severely damaged in day 3 and day 7 images and were absent at 21 days. Significant edema, an indicator of inflammation, was observed in the tissue and at day 21, there was limited to no evidence of recovery from the observed histopathology.

Treatment with the SELP 815K 11 wt % enema substantially maintained the rectal epithelium, possibly by "holding" the lumen together, leading to reduced epithelial loss at 3 and 7 days compared to the GAG in PBS enema. The crypts, however, were moderately damaged, and edema was observed at day 3. By day 7, the crypts and goblet cells were virtually eliminated. The crypts recovered somewhat by day 21, showed dilation and formation of cryptic abscesses, and continued edema. SELP edema had little impact on inflammation when it was administered without GAG and the inflammatory response was similar to that observed in the GAG in PBS group. By day 21, moderate recovery was observed within the groups treated with GAG in PBS and SELP alone as evidenced by the reemergence of the crypts and goblet cells but continued moderate edema.

SELP 815K 11 wt % and GAG GM-0111 administered together had the greatest observed therapeutic effect. Mild edema was observed at day 3, but was reduced at days 7 and 21. The crypts of Lieberkühn exhibited moderate damage at day 3, but this damage was mostly ameliorated at day 7. Overall, the epithelial layers remained intact and the tissues demonstrated less inflammation. Less dilation and damage to the crypts of Lieberkühn were observed when compared to the other treatment groups. Edema was observable in the crypts at day 21, but not within the sub-mucosa, unlike the SELP only group.

Throughout this publication, various publications are referenced. The disclosures of these publications in their entireties are hereby incorporated by reference into this application in order to more fully describe the methods, compositions, and compounds herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed is:

1. A composition comprising: 10% to 20% (w/w) of a sulfated hyaluronan having an average molecular size from 2 kDa to 10 kDa, pharmaceutically acceptable salt, or ester thereof; and 3% to 12% (w/w) of a silk-elastin like protein comprising one or more silk block domains having 2, 4, 5, 7, 8, 11, 12, 13, or 18 repeats and one or more elastin block domains having 4, 5, 6, 8, 11, 12, 16, 17, or 32 repeats; wherein: the composition is a liquid prior to administration but converts to a gel upon administration to a subject's rectum; and the composition releases 100% of the sulfated hyaluronan within 24 hours in the subject's rectum.

2. The composition of claim 1, wherein:
(i) 100% of the primary C-6 hydroxyl protons of the N-acetyl-glucosamine residue of the sulfated hyaluronan are substituted with a sulfate group;
(ii) the sulfated hyaluronan has a degree of sulfation from 3.0 to 4.0; and
(iii) the sulfated hyaluronan has an average molecular weight from 1 kDa to 3 kDa.

3. The composition of claim 1, wherein the pharmaceutically acceptable ester of the sulfated hyaluronan is a prodrug.

4. The composition of claim 1, wherein the sulfated hyaluronan or a pharmaceutically-acceptable salt or ester thereof has at least one sulfate group and at least one primary C-6 hydroxyl position of an N-acetyl-glucosamine residue having a methyl group.

5. The composition of claim 1, wherein the pharmaceutically acceptable salt of the sulfated hyaluronan comprises an organic salt, a metal salt, or a combination thereof.

6. The composition of claim 1, wherein the silk-elastin like protein comprises sheared silk-elastin like protein 415K or 815K.

7. The composition of claim 1, wherein the composition further comprises an antioxidant, a mucoadhesive agent, an anti-inflammatory agent, an anti-pyretic agent, steroidal and non-steroidal drugs for anti-inflammatory use, a hormone, a growth factor, a contraceptive agent, an antiviral, an antibacterial, an antifungal, an analgesics, a hypnotic, a sedative, a tranquilizer, an anti-convulsant, a muscle relaxant, a local anesthetic, an antispasmodic, an antiulcer drug, a peptidic agonist, a sympathomimetic agent, a cardiovascular agent, an antitumor agent, or an oligonucleotide.

8. The composition of claim 1, wherein the composition further comprises a contrast agent.

9. A method for reducing or preventing inflammation and/or tissue damage in a subject comprising administering to the subject the composition of claim 1.

10. A method for prophylactically treating inflammation and/or tissue damage comprising administration to the subject the composition of claim 1 prior to administration of a source of inflammation to the subject.

11. The composition of claim 1, wherein the composition is an injectable composition from 18° C. to 23° C.

12. The composition of claim 1, wherein the composition has a viscosity of less than or equal to or less than 2500 cP at 18° C. to 23° C.

13. The composition of claim 1, wherein the composition has a viscosity of less than equal to 700 cP at 18° C. to 23° C.

14. The composition of claim 1, wherein the composition is a hydrogel at 37° C.

* * * * *

SEQUENCE LISTING

<160> NUMBER OF SEQ ID NOS: 36

<210> SEQ ID NO 1
<211> LENGTH: 6
<212> TYPE: PRT

```
<213> ORGANISM: Artificial sequence
<220> FEATURE:
<223> OTHER INFORMATION: Synthetic construct

<400> SEQUENCE: 1

Gly Ala Gly Ala Gly Ser
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic construct

<400> SEQUENCE: 2

Gly Val Gly Val Pro
1               5

<210> SEQ ID NO 3
<211> LENGTH: 884
<212> TYPE: PRT
<213> ORGANISM: Artificial sequence
<220> FEATURE:
<223> OTHER INFORMATION: Synthetic construct

<400> SEQUENCE: 3

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
                20                  25                  30

Gly Val Gly Val Pro Gly Val Gly Ala Gly Ala Gly Ser Gly Ala
        35                  40                  45

Gly Ala Gly Ser Val Pro Gly Val Gly Val Pro Gly Val Gly Val Pro
    50                  55                  60

Gly Val Gly Val Pro Gly Val Gly Val Pro Gly Val Gly Val Pro Gly
65                  70                  75                  80

Val Gly Val Pro Gly Val Gly Val Pro Gly Val Gly Ala Gly Ala
                85                  90                  95

Gly Ser Gly Ala Gly Ala Gly Ser Val Pro Gly Val Gly Val Pro Gly
            100                 105                 110

Val Gly Val Pro Gly Val Gly Val Pro Gly Val Gly Val Pro Gly Val
        115                 120                 125

Gly Val Pro Gly Val Gly Val Pro Gly Val Gly Val Pro Gly Val Gly
    130                 135                 140

Gly Ala Gly Ala Gly Ser Gly Ala Gly Ala Gly Ser Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Gly Ala Gly Ala Gly Ser Gly Ala Gly Ala Gly Ser
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Gly Ala Gly Ala Gly Ser Gly Ala
                245                 250                 255
```

```
Gly Ala Gly Ser Val Pro Gly Val Gly Val Pro Val Gly Val Pro
            260                 265                 270

Gly Val Gly Val Pro Gly Val Gly Val Pro Gly Val Gly Val Pro Gly
            275                 280                 285

Val Gly Val Pro Gly Val Gly Val Pro Gly Val Gly Gly Ala Gly Ala
            290                 295                 300

Gly Ser Gly Ala Gly Ala Gly Ser Val Pro Gly Val Gly Val Pro Gly
305                 310                 315                 320

Val Gly Val Pro Gly Val Gly Val Pro Gly Val Gly Val Pro Gly Val
            325                 330                 335

Gly Val Pro Gly Val Gly Val Pro Gly Val Gly Val Pro Gly Val Gly
            340                 345                 350

Gly Ala Gly Ala Gly Ser Gly Ala Gly Ala Gly Ser Val Pro Gly Val
            355                 360                 365

Gly Val Pro Gly Val Gly Val Pro Gly Val Gly Val Pro Gly Val Gly
            370                 375                 380

Val Pro Gly Val Gly Val Pro Gly Val Gly Val Pro Gly Val Gly Val
385                 390                 395                 400

Pro Gly Val Gly Gly Ala Gly Ala Gly Ser Gly Ala Gly Ala Gly Ser
            405                 410                 415

Val Pro Gly Val Gly Val Pro Gly Val Gly Val Pro Gly Val Gly Val
            420                 425                 430

Pro Gly Val Gly Val Pro Gly Val Gly Val Pro Gly Val Gly Val Pro
            435                 440                 445

Gly Val Gly Val Pro Gly Val Gly Gly Ala Gly Ala Gly Ser Gly Ala
            450                 455                 460

Gly Ala Gly Ser Val Pro Gly Val Gly Val Pro Gly Val Gly Val Pro
465                 470                 475                 480

Gly Val Gly Val Pro Gly Val Gly Val Pro Gly Val Gly Val Pro Gly
            485                 490                 495

Val Gly Val Pro Gly Val Gly Val Pro Gly Val Gly Gly Ala Gly Ala
            500                 505                 510

Gly Ser Gly Ala Gly Ala Gly Ser Val Pro Gly Val Gly Val Pro Gly
            515                 520                 525

Val Gly Val Pro Gly Val Gly Val Pro Gly Val Gly Val Pro Gly Val
            530                 535                 540

Gly Val Pro Gly Val Gly Val Pro Gly Val Gly Val Pro Gly Val Gly
545                 550                 555                 560

Gly Ala Gly Ala Gly Ser Gly Ala Gly Ala Gly Ser Val Pro Gly Val
            565                 570                 575

Gly Val Pro Gly Val Gly Val Pro Gly Val Gly Val Pro Gly Val Gly
            580                 585                 590

Val Pro Gly Val Gly Val Pro Gly Val Gly Val Pro Gly Val Gly Val
            595                 600                 605

Pro Gly Val Gly Gly Ala Gly Ala Gly Ser Gly Ala Gly Ala Gly Ser
            610                 615                 620

Val Pro Gly Val Gly Val Pro Gly Val Gly Val Pro Gly Val Gly Val
625                 630                 635                 640

Pro Gly Val Gly Val Pro Gly Val Gly Val Pro Gly Val Gly Val Pro
            645                 650                 655

Gly Val Gly Val Pro Gly Val Gly Gly Ala Gly Ala Gly Ser Gly Ala
            660                 665                 670
```

```
Gly Ala Gly Ser Val Pro Gly Val Gly Val Pro Gly Val Pro
            675                 680                 685

Gly Val Gly Val Pro Gly Val Gly Val Pro Gly Val Gly Val Pro Gly
    690                 695                 700

Val Gly Val Pro Gly Val Gly Val Pro Gly Val Gly Ala Gly Ala
705                 710                 715                 720

Gly Ser Gly Ala Gly Ala Gly Ser Val Pro Gly Val Gly Val Pro Gly
            725                 730                 735

Val Gly Val Pro Gly Val Gly Val Pro Gly Val Gly Val Pro Gly Val
            740                 745                 750

Gly Val Pro Gly Val Gly Val Pro Gly Val Gly Val Pro Gly Val Gly
            755                 760                 765

Gly Ala Gly Ala Gly Ser Gly Ala Gly Ala Gly Ser Val Pro Gly Val
            770                 775                 780

Gly Val Pro Gly Val Gly Val Pro Gly Val Gly Val Pro Gly Val Gly
785                 790                 795                 800

Val Pro Gly Val Gly Val Pro Gly Val Gly Val Pro Gly Val Gly Val
            805                 810                 815

Pro Gly Val Gly Gly Ala Gly Ala Gly Ser Gly Ala Gly Ala Gly Ser
            820                 825                 830

Val Pro Gly Val Gly Val Pro Gly Val Gly Val Pro Gly Val Gly Val
            835                 840                 845

Pro Gly Val Gly Val Pro Gly Val Gly Val Pro Gly Val Gly Val Pro
            850                 855                 860

Gly Val Gly Val Pro Gly Val Gly Ala Gly Ala Gly Ser Gly Ala
865                 870                 875                 880

Gly Ala Gly Ser

<210> SEQ ID NO 4
<211> LENGTH: 962
<212> TYPE: PRT
<213> ORGANISM: Artificial sequence
<220> FEATURE:
<223> OTHER INFORMATION: Synthetic construct

<400> SEQUENCE: 4

Gly Val Gly Val Pro Gly Val Gly Val Pro Gly Val Gly Val Pro Gly
1               5                   10                  15

Val Gly Val Pro Gly Ala Gly Ala Gly Ser Gly Ala Gly Ala Gly Ser
            20                  25                  30

Gly Ala Gly Ala Gly Ser Gly Ala Gly Ala Gly Ser Gly Ala Gly Ala
            35                  40                  45

Gly Ser Gly Ala Gly Ala Gly Ser Gly Ala Gly Ala Gly Ser Gly Ala
        50                  55                  60

Gly Ala Gly Ser Gly Ala Gly Ala Gly Ser Val Gly Val Pro Gly
65                  70                  75                  80

Val Gly Val Pro Gly Val Gly Val Pro Gly Val Gly Val Pro Gly Ala
            85                  90                  95

Gly Ala Gly Ser Gly Ala Gly Ala Gly Ser Gly Ala Gly Ala Gly Ser
            100                 105                 110

Gly Ala Gly Ala Gly Ser Gly Ala Gly Ala Gly Ser Gly Ala Gly Ala
            115                 120                 125

Gly Ser Gly Ala Gly Ala Gly Ser Gly Ala Gly Ala Gly Ser Gly Ala
        130                 135                 140

Gly Ala Gly Ser Gly Val Gly Val Pro Gly Val Gly Val Pro Gly Val
```

```
        145                 150                 155                 160
Gly Val Pro Gly Val Gly Val Pro Gly Ala Gly Ala Gly Ser Gly Ala
                165                 170                 175
Gly Ala Gly Ser Gly Ala Gly Ala Gly Ser Gly Ala Gly Ala Gly Ser
                180                 185                 190
Gly Ala Gly Ala Gly Ser Gly Ala Gly Ala Gly Ser Gly Ala Gly Ala
                195                 200                 205
Gly Ser Gly Ala Gly Ala Gly Ser Gly Ala Gly Ala Gly Ser Gly Val
                210                 215                 220
Gly Val Pro Gly Val Gly Val Pro Gly Val Gly Val Pro Gly Val Gly
225                 230                 235                 240
Val Pro Gly Ala Gly Ala Gly Ser Gly Ala Gly Ala Gly Ser Gly Ala
                245                 250                 255
Gly Ala Gly Ser Gly Ala Gly Ala Gly Ser Gly Ala Gly Ala Gly Ser
                260                 265                 270
Gly Ala Gly Ala Gly Ser Gly Ala Gly Ala Gly Ser Gly Ala Gly Ala
                275                 280                 285
Gly Ser Gly Ala Gly Ala Gly Ser Gly Val Gly Val Pro Gly Val Gly
                290                 295                 300
Val Pro Gly Val Gly Val Pro Gly Val Gly Val Pro Gly Ala Gly Ala
305                 310                 315                 320
Gly Ser Gly Ala Gly Ala Gly Ser Gly Ala Gly Ala Gly Ser Gly Ala
                325                 330                 335
Gly Ala Gly Ser Gly Ala Gly Ala Gly Ser Gly Ala Gly Ala Gly Ser
                340                 345                 350
Gly Ala Gly Ala Gly Ser Gly Ala Gly Ala Gly Ser Gly Ala Gly Ala
                355                 360                 365
Gly Ser Gly Val Gly Val Pro Gly Val Gly Val Pro Gly Val Gly Val
                370                 375                 380
Pro Gly Val Gly Val Pro Gly Ala Gly Ala Gly Ser Gly Ala Gly Ala
385                 390                 395                 400
Gly Ser Gly Ala Gly Ala Gly Ser Gly Ala Gly Ala Gly Ser Gly Ala
                405                 410                 415
Gly Ala Gly Ser Gly Ala Gly Ala Gly Ser Gly Ala Gly Ala Gly Ser
                420                 425                 430
Gly Ala Gly Ala Gly Ser Gly Ala Gly Ala Gly Ser Gly Val Gly Val
                435                 440                 445
Pro Gly Val Gly Val Pro Gly Val Gly Val Pro Gly Val Gly Val Pro
450                 455                 460
Gly Ala Gly Ala Gly Ser Gly Ala Gly Ala Gly Ser Gly Ala Gly Ala
465                 470                 475                 480
Gly Ser Gly Ala Gly Ala Gly Ser Gly Ala Gly Ala Gly Ser Gly Ala
                485                 490                 495
Gly Ala Gly Ser Gly Ala Gly Ala Gly Ser Gly Ala Gly Ala Gly Ser
                500                 505                 510
Gly Ala Gly Ala Gly Ser Gly Val Gly Val Pro Gly Val Gly Val Pro
                515                 520                 525
Gly Val Gly Val Pro Gly Val Gly Val Pro Gly Ala Gly Ala Gly Ser
                530                 535                 540
Gly Ala Gly Ala Gly Ser Gly Ala Gly Ala Gly Ser Gly Ala Gly Ala
545                 550                 555                 560
Gly Ser Gly Ala Gly Ala Gly Ser Gly Ala Gly Ala Gly Ser Gly Ala
                565                 570                 575
```

```
Gly Ala Gly Ser Gly Ala Gly Ala Gly Ser Gly Ala Gly Ala Gly Ser
            580                 585                 590

Gly Val Gly Val Pro Gly Val Gly Val Pro Gly Val Gly Val Pro Gly
    595                 600                 605

Val Gly Val Pro Gly Ala Gly Ala Gly Ser Gly Ala Gly Ala Gly Ser
610                 615                 620

Gly Ala Gly Ala Gly Ser Gly Ala Gly Ala Gly Ser Gly Ala Gly Ala
625                 630                 635                 640

Gly Ser Gly Ala Gly Ala Gly Ser Gly Ala Gly Ala Gly Ser Gly Ala
            645                 650                 655

Gly Ala Gly Ser Gly Ala Gly Ala Gly Ser Gly Val Gly Val Pro Gly
            660                 665                 670

Val Gly Val Pro Gly Val Gly Val Pro Gly Val Gly Val Pro Gly Ala
            675                 680                 685

Gly Ala Gly Ser Gly Ala Gly Ala Gly Ser Gly Ala Gly Ala Gly Ser
            690                 695                 700

Gly Ala Gly Ala Gly Ser Gly Ala Gly Ala Gly Ser Gly Ala Gly Ala
705                 710                 715                 720

Gly Ser Gly Ala Gly Ala Gly Ser Gly Ala Gly Ala Gly Ser Gly Ala
            725                 730                 735

Gly Ala Gly Ser Gly Val Gly Val Pro Gly Val Gly Val Pro Gly Val
            740                 745                 750

Gly Val Pro Gly Val Gly Val Pro Gly Ala Gly Ala Gly Ser Gly Ala
            755                 760                 765

Gly Ala Gly Ser Gly Ala Gly Ala Gly Ser Gly Ala Gly Ala Gly Ser
            770                 775                 780

Gly Ala Gly Ala Gly Ser Gly Ala Gly Ala Gly Ser Gly Ala Gly Ala
785                 790                 795                 800

Gly Ser Gly Ala Gly Ala Gly Ser Gly Ala Gly Ala Gly Ser Gly Val
            805                 810                 815

Gly Val Pro Gly Val Gly Val Pro Gly Val Gly Val Pro Gly Val Gly
            820                 825                 830

Val Pro Gly Ala Gly Ala Gly Ser Gly Ala Gly Ala Gly Ser Gly Ala
            835                 840                 845

Gly Ala Gly Ser Gly Ala Gly Ala Gly Ser Gly Ala Gly Ala Gly Ser
            850                 855                 860

Gly Ala Gly Ala Gly Ser Gly Ala Gly Ala Gly Ser Gly Ala Gly Ala
865                 870                 875                 880

Gly Ser Gly Ala Gly Ala Gly Ser Gly Val Gly Val Pro Gly Val Gly
            885                 890                 895

Val Pro Gly Val Gly Val Pro Gly Val Gly Val Pro Gly Ala Gly Ala
            900                 905                 910

Gly Ser Gly Ala Gly Ala Gly Ser Gly Ala Gly Ala Gly Ser Gly Ala
            915                 920                 925

Gly Ala Gly Ser Gly Ala Gly Ala Gly Ser Gly Ala Gly Ala Gly Ser
            930                 935                 940

Gly Ala Gly Ala Gly Ser Gly Ala Gly Ala Gly Ser Gly Ala Gly Ala
945                 950                 955                 960

Gly Ser
```

<210> SEQ ID NO 5
<211> LENGTH: 768
<212> TYPE: PRT

<213> ORGANISM: Artificial sequence
<220> FEATURE:
<223> OTHER INFORMATION: Synthetic construct

<400> SEQUENCE: 5

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
            85                  90                  95

Gly Val Gly Val Pro Gly Val Gly Ala Gly Ala Gly Ser Gly Ala
        100                 105                 110

Gly Ala Gly Ser Gly Ala Gly Ala Gly Ser Gly Ala Gly Ala Gly Ser
    115                 120                 125

Val Pro Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Ala Gly Ala Gly Ser Gly Ala
        165                 170                 175

Gly Ala Gly Ser Gly Ala Gly Ala Gly Ser Gly Ala Gly Ala Gly Ser
        180                 185                 190

Val Pro Gly Val Gly Val Pro Gly Val Gly Val Pro Gly Val Gly Val
        195                 200                 205

Pro Gly Val Gly Val Pro Gly Val Gly Val Pro Gly Val Gly Val Pro
    210                 215                 220

Gly Val Gly Val Pro Gly Val Gly Ala Gly Ala Gly Ser Gly Ala
225                 230                 235                 240

Gly Ala Gly Ser Gly Ala Gly Ala Gly Ser Gly Ala Gly Ala Gly Ser
            245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Ala Gly Ala Gly Ser Gly Ala
        290                 295                 300

Gly Ala Gly Ser Gly Ala Gly Ala Gly Ser Gly Ala Gly Ala Gly Ser
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Val Gly Val Pro Gly Val Gly Ala Gly Ala Gly Ser Gly Ala
        355                 360                 365

Gly Ala Gly Ser Gly Ala Gly Ala Gly Ser Gly Ala Gly Ala Gly Ser
    370                 375                 380

Val Pro Gly Val Gly Val Pro Gly Val Gly Val Pro Gly Val Gly Val
```

```
            385                 390                 395                 400
Pro Gly Val Gly Val Pro Gly Val Gly Val Pro Gly Val Gly Val Pro
                405                 410                 415
Gly Val Gly Val Pro Gly Val Gly Ala Gly Ala Gly Ser Gly Ala
            420                 425                 430
Gly Ala Gly Ser Gly Ala Gly Ala Gly Ser Gly Ala Gly Ala Gly Ser
            435                 440                 445
Val Pro Gly Val Gly Val Pro Gly Val Gly Val Pro Gly Val Gly Val
450                 455                 460
Pro Gly Val Gly Val Pro Gly Val Gly Val Pro Gly Val Gly Val Pro
465                 470                 475                 480
Gly Val Gly Val Pro Gly Val Gly Ala Gly Ala Gly Ser Gly Ala
            485                 490                 495
Gly Ala Gly Ser Gly Ala Gly Ala Gly Ser Gly Ala Gly Ala Gly Ser
            500                 505                 510
Val Pro Gly Val Gly Val Pro Gly Val Gly Val Pro Gly Val Gly Val
            515                 520                 525
Pro Gly Val Gly Val Pro Gly Val Gly Val Pro Gly Val Gly Val Pro
            530                 535                 540
Gly Val Gly Val Pro Gly Val Gly Ala Gly Ala Gly Ser Gly Ala
545                 550                 555                 560
Gly Ala Gly Ser Gly Ala Gly Ala Gly Ser Gly Ala Gly Ala Gly Ser
            565                 570                 575
Val Pro Gly Val Gly Val Pro Gly Val Gly Val Pro Gly Val Gly Val
            580                 585                 590
Pro Gly Val Gly Val Pro Gly Val Gly Val Pro Gly Val Gly Val Pro
            595                 600                 605
Gly Val Gly Val Pro Gly Val Gly Ala Gly Ala Gly Ser Gly Ala
            610                 615                 620
Gly Ala Gly Ser Gly Ala Gly Ala Gly Ser Gly Ala Gly Ala Gly Ser
625                 630                 635                 640
Val Pro Gly Val Gly Val Pro Gly Val Gly Val Pro Gly Val Gly Val
            645                 650                 655
Pro Gly Val Gly Val Pro Gly Val Gly Val Pro Gly Val Gly Val Pro
            660                 665                 670
Gly Val Gly Val Pro Gly Val Gly Ala Gly Ala Gly Ser Gly Ala
            675                 680                 685
Gly Ala Gly Ser Gly Ala Gly Ala Gly Ser Gly Ala Gly Ala Gly Ser
            690                 695                 700
Val Pro Gly Val Gly Val Pro Gly Val Gly Val Pro Gly Val Gly Val
705                 710                 715                 720
Pro Gly Val Gly Val Pro Gly Val Gly Val Pro Gly Val Gly Val Pro
            725                 730                 735
Gly Val Gly Val Pro Gly Val Gly Ala Gly Ala Gly Ser Gly Ala
            740                 745                 750
Gly Ala Gly Ser Gly Ala Gly Ala Gly Ser Gly Ala Gly Ala Gly Ser
            755                 760                 765

<210> SEQ ID NO 6
<211> LENGTH: 912
<212> TYPE: PRT
<213> ORGANISM: Artificial sequence
<220> FEATURE:
<223> OTHER INFORMATION: Synthetic construct
```

<400> SEQUENCE: 6

```
Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
            20                  25                  30
Gly Val Gly Val Pro Gly Val Gly Ala Gly Ala Gly Ser Gly Ala
        35                  40                  45
Gly Ala Gly Ser Gly Ala Gly Ala Gly Ser Gly Ala Gly Ala Gly Ser
50                  55                  60
Gly Ala Gly Ala Gly Ser Gly Ala Gly Ala Gly Ser Val Pro Gly Val
65                  70                  75                  80
Gly Val Pro Gly Val Gly Val Pro Gly Val Gly Val Pro Gly Val Gly
            85                  90                  95
Val Pro Gly Val Gly Val Pro Gly Val Gly Val Pro Gly Val Gly Val
                100                 105                 110
Pro Gly Val Gly Gly Ala Gly Ala Gly Ser Gly Ala Gly Ala Gly Ser
            115                 120                 125
Gly Ala Gly Ala Gly Ser Gly Ala Gly Ala Gly Ser Gly Ala Gly Ala
    130                 135                 140
Gly Ser Gly Ala Gly Ala Gly Ser Val Pro Gly Val Gly Val Pro Gly
145                 150                 155                 160
Val Gly Val Pro Gly Val Gly Val Pro Gly Val Gly Val Pro Gly Val
                165                 170                 175
Gly Val Pro Gly Val Gly Val Pro Gly Val Gly Val Pro Gly Val Gly
            180                 185                 190
Gly Ala Gly Ala Gly Ser Gly Ala Gly Ala Gly Ser Gly Ala Gly Ala
        195                 200                 205
Gly Ser Gly Ala Gly Ala Gly Ser Gly Ala Gly Ala Gly Ser Gly Ala
    210                 215                 220
Gly Ala Gly Ser Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Gly Ala Gly Ala
            260                 265                 270
Gly Ser Gly Ala Gly Ala Gly Ser Gly Ala Gly Ala Gly Ser Gly Ala
        275                 280                 285
Gly Ala Gly Ser Gly Ala Gly Ala Gly Ser Gly Ala Gly Ala Gly Ser
    290                 295                 300
Val Pro Gly Val Gly Val Pro Gly Val Gly Val Pro Gly Val Gly Val
305                 310                 315                 320
Pro Gly Val Gly Val Pro Gly Val Gly Val Pro Gly Val Gly Val Pro
                325                 330                 335
Gly Val Gly Val Pro Gly Val Gly Gly Ala Gly Ala Gly Ser Gly Ala
            340                 345                 350
Gly Ala Gly Ser Gly Ala Gly Ala Gly Ser Gly Ala Gly Ala Gly Ser
        355                 360                 365
Gly Ala Gly Ala Gly Ser Gly Ala Gly Ala Gly Ser Val Pro Gly Val
    370                 375                 380
Gly Val Pro Gly Val Gly Val Pro Gly Val Gly Val Pro Gly Val Gly
385                 390                 395                 400
Val Pro Gly Val Gly Val Pro Gly Val Gly Val Pro Gly Val Gly Val
                405                 410                 415
```

```
Pro Gly Val Gly Gly Ala Gly Ala Gly Ser Gly Ala Gly Ala Gly Ser
            420                 425                 430
Gly Ala Gly Ala Gly Ser Gly Ala Gly Ala Gly Ser Gly Ala Gly Ala
        435                 440                 445
Gly Ser Gly Ala Gly Ala Gly Ser Val Pro Gly Val Gly Val Pro Gly
    450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
            485                 490                 495
Gly Ala Gly Ala Gly Ser Gly Ala Gly Ala Gly Ser Gly Ala Gly Ala
        500                 505                 510
Gly Ser Gly Ala Gly Ala Gly Ser Gly Ala Gly Ala Gly Ser Gly Ala
    515                 520                 525
Gly Ala Gly Ser Val Pro Gly Val Gly Val Pro Gly Val Gly Val Pro
530                 535                 540
Gly Val Gly Val Pro Gly Val Gly Val Pro Gly Val Gly Val Pro Gly
545                 550                 555                 560
Val Gly Val Pro Gly Val Gly Val Pro Gly Val Gly Ala Gly Ala
            565                 570                 575
Gly Ser Gly Ala Gly Ala Gly Ser Gly Ala Gly Ala Gly Ser Gly Ala
        580                 585                 590
Gly Ala Gly Ser Gly Ala Gly Ala Gly Ser Gly Ala Gly Ala Gly Ser
        595                 600                 605
Val Pro Gly Val Gly Val Pro Gly Val Gly Val Pro Gly Val Gly Val
    610                 615                 620
Pro Gly Val Gly Val Pro Gly Val Gly Val Pro Gly Val Gly Val Pro
625                 630                 635                 640
Gly Val Gly Val Pro Gly Val Gly Ala Gly Ala Gly Ser Gly Ala
            645                 650                 655
Gly Ala Gly Ser Gly Ala Gly Ala Gly Ser Gly Ala Gly Ala Gly Ser
        660                 665                 670
Gly Ala Gly Ala Gly Ser Gly Ala Gly Ala Gly Ser Val Pro Gly Val
        675                 680                 685
Gly Val Pro Gly Val Gly Val Pro Gly Val Gly Val Pro Gly Val Gly
    690                 695                 700
Val Pro Gly Val Gly Val Pro Gly Val Gly Val Pro Gly Val Gly Val
705                 710                 715                 720
Pro Gly Val Gly Gly Ala Gly Ala Gly Ser Gly Ala Gly Ala Gly Ser
            725                 730                 735
Gly Ala Gly Ala Gly Ser Gly Ala Gly Ala Gly Ser Gly Ala Gly Ala
        740                 745                 750
Gly Ser Gly Ala Gly Ala Gly Ser Val Pro Gly Val Gly Val Pro Gly
    755                 760                 765
Val Gly Val Pro Gly Val Gly Val Pro Gly Val Gly Val Pro Gly Val
    770                 775                 780
Gly Val Pro Gly Val Gly Val Pro Gly Val Gly Val Pro Gly Val Gly
785                 790                 795                 800
Gly Ala Gly Ala Gly Ser Gly Ala Gly Ala Gly Ser Gly Ala Gly Ala
        805                 810                 815
Gly Ser Gly Ala Gly Ala Gly Ser Gly Ala Gly Ala Gly Ser Gly Ala
        820                 825                 830
```

-continued

Gly Ala Gly Ser Val Pro Gly Val Gly Val Pro Gly Val Pro
            835                 840                 845

Gly Val Gly Val Pro Gly Val Gly Val Pro Gly Val Gly Val Pro Gly
    850                 855                 860

Val Gly Val Pro Gly Val Gly Val Pro Gly Val Gly Ala Gly Ala
865                 870                 875                 880

Gly Ser Gly Ala Gly Ala Gly Ser Ala Gly Ala Gly Ser Gly Ala
            885                 890                 895

Gly Ala Gly Ser Gly Ala Gly Ala Gly Ser Gly Ala Gly Ala Gly Ser
            900                 905                 910

<210> SEQ ID NO 7
<211> LENGTH: 968
<212> TYPE: PRT
<213> ORGANISM: Artificial sequence
<220> FEATURE:
<223> OTHER INFORMATION: Synthetic construct

<400> SEQUENCE: 7

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Ala Gly Ala Gly Ser Gly Ala
            35                  40                  45

Gly Ala Gly Ser Gly Ala Gly Ala Gly Ser Gly Ala Gly Ala Gly Ser
        50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser Val Pro Gly Val Gly Val Pro Gly
            85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
            115                 120                 125

Gly Ala Gly Ala Gly Ser Gly Ala Gly Ala Gly Ser Gly Ala Gly Ala
    130                 135                 140

Gly Ser Gly Ala Gly Ala Gly Ser Gly Ala Gly Ala Gly Ser Gly Ala
145                 150                 155                 160

Gly Ala Gly Ser Gly Ala Gly Ala Gly Ser Gly Ala Gly Ala Gly Ser
            165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
    195                 200                 205

Gly Val Gly Val Pro Gly Val Gly Ala Gly Ala Gly Ser Gly Ala
    210                 215                 220

Gly Ala Gly Ser Gly Ala Gly Ala Gly Ser Gly Ala Gly Ala Gly Ser
225                 230                 235                 240

Gly Ala Gly Ala Gly Ser Gly Ala Gly Ala Gly Ser Gly Ala Gly Ala
            245                 250                 255

Gly Ser Gly Ala Gly Ala Gly Ser Val Pro Gly Val Gly Val Pro Gly
            260                 265                 270

Val Gly Val Pro Gly Val Gly Val Pro Gly Val Gly Val Pro Gly Val
            275                 280                 285

```
Gly Val Pro Gly Val Gly Val Pro Gly Val Gly Val Pro Gly Val Gly
        290                 295                 300
Gly Ala Gly Ala Gly Ser Gly Ala Gly Ala Gly Ser Gly Ala Gly Ala
305                 310                 315                 320
Gly Ser Gly Ala Gly Ala Gly Ser Gly Ala Gly Ala Gly Ser Gly Ala
                325                 330                 335
Gly Ala Gly Ser Gly Ala Gly Ala Gly Ser Gly Ala Gly Ala Gly Ser
                340                 345                 350
Val Pro Gly Val Gly Val Pro Gly Val Gly Val Pro Gly Val Gly Val
        355                 360                 365
Pro Gly Val Gly Val Pro Gly Val Gly Val Pro Gly Val Gly Val Pro
370                 375                 380
Gly Val Gly Val Pro Gly Val Gly Ala Gly Ala Gly Ser Gly Ala
385                 390                 395                 400
Gly Ala Gly Ser Gly Ala Gly Ala Gly Ser Gly Ala Gly Ala Gly Ser
                405                 410                 415
Gly Ala Gly Ala Gly Ser Gly Ala Gly Ala Gly Ser Gly Ala Gly Ala
                420                 425                 430
Gly Ser Gly Ala Gly Ala Gly Ser Val Pro Gly Val Gly Val Pro Gly
                435                 440                 445
Val Gly Val Pro Gly Val Gly Val Pro Gly Val Gly Val Pro Gly Val
450                 455                 460
Gly Val Pro Gly Val Gly Val Pro Gly Val Gly Val Pro Gly Val Gly
465                 470                 475                 480
Gly Ala Gly Ala Gly Ser Gly Ala Gly Ala Gly Ser Gly Ala Gly Ala
                485                 490                 495
Gly Ser Gly Ala Gly Ala Gly Ser Gly Ala Gly Ala Gly Ser Gly Ala
                500                 505                 510
Gly Ala Gly Ser Gly Ala Gly Ala Gly Ser Gly Ala Gly Ala Gly Ser
                515                 520                 525
Val Pro Gly Val Gly Val Pro Gly Val Gly Val Pro Gly Val Gly Val
        530                 535                 540
Pro Gly Val Gly Val Pro Gly Val Gly Val Pro Gly Val Gly Val Pro
545                 550                 555                 560
Gly Val Gly Val Pro Gly Val Gly Ala Gly Ala Gly Ser Gly Ala
                565                 570                 575
Gly Ala Gly Ser Gly Ala Gly Ala Gly Ser Gly Ala Gly Ala Gly Ser
                580                 585                 590
Gly Ala Gly Ala Gly Ser Gly Ala Gly Ala Gly Ser Gly Ala Gly Ala
                595                 600                 605
Gly Ser Gly Ala Gly Ala Gly Ser Val Pro Gly Val Gly Val Pro Gly
                610                 615                 620
Val Gly Val Pro Gly Val Gly Val Pro Gly Val Gly Val Pro Gly Val
625                 630                 635                 640
Gly Val Pro Gly Val Gly Val Pro Gly Val Gly Val Pro Gly Val Gly
                645                 650                 655
Gly Ala Gly Ala Gly Ser Gly Ala Gly Ala Gly Ser Gly Ala Gly Ala
                660                 665                 670
Gly Ser Gly Ala Gly Ala Gly Ser Gly Ala Gly Ala Gly Ser Gly Ala
                675                 680                 685
Gly Ala Gly Ser Gly Ala Gly Ala Gly Ser Gly Ala Gly Ala Gly Ser
                690                 695                 700
Val Pro Gly Val Gly Val Pro Gly Val Gly Val Pro Gly Val Gly Val
```

```
                    705                 710                 715                 720
Pro Gly Val Gly Val Pro Gly Val Gly Val Pro Gly Val Gly Val Pro
                725                 730                 735
Gly Val Gly Val Pro Gly Val Gly Ala Gly Ala Gly Ser Gly Ala
            740                 745                 750
Gly Ala Gly Ser Gly Ala Gly Ala Gly Ser Gly Ala Gly Ala Gly Ser
            755                 760                 765
Gly Ala Gly Ala Gly Ser Gly Ala Gly Ala Gly Ser Gly Ala Gly Ala
            770                 775                 780
Gly Ser Gly Ala Gly Ala Gly Ser Val Pro Gly Val Gly Val Pro Gly
785                 790                 795                 800
Val Gly Val Pro Gly Val Gly Val Pro Gly Val Gly Val Pro Gly Val
                805                 810                 815
Gly Val Pro Gly Val Gly Val Pro Gly Val Gly Val Pro Gly Val Gly
            820                 825                 830
Gly Ala Gly Ala Gly Ser Gly Ala Gly Ala Gly Ser Gly Ala Gly Ala
            835                 840                 845
Gly Ser Gly Ala Gly Ala Gly Ser Gly Ala Gly Ala Gly Ser Gly Ala
            850                 855                 860
Gly Ala Gly Ser Gly Ala Gly Ala Gly Ser Gly Ala Gly Ala Gly Ser
865                 870                 875                 880
Val Pro Gly Val Gly Val Pro Gly Val Gly Val Pro Gly Val Gly Val
                885                 890                 895
Pro Gly Val Gly Val Pro Gly Val Gly Val Pro Gly Val Gly Val Pro
                900                 905                 910
Gly Val Gly Val Pro Gly Val Gly Ala Gly Ala Gly Ser Gly Ala
            915                 920                 925
Gly Ala Gly Ser Gly Ala Gly Ala Gly Ser Gly Ala Gly Ala Gly Ser
            930                 935                 940
Gly Ala Gly Ala Gly Ser Gly Ala Gly Ala Gly Ser Gly Ala Gly Ala
945                 950                 955                 960
Gly Ser Gly Ala Gly Ala Gly Ser
                965

<210> SEQ ID NO 8
<211> LENGTH: 864
<212> TYPE: PRT
<213> ORGANISM: Artificial sequence
<220> FEATURE:
<223> OTHER INFORMATION: Synthetic construct

<400> SEQUENCE: 8

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
                20                  25                  30
Gly Val Gly Val Pro Gly Val Gly Val Pro Gly Val Gly Val Pro Gly
            35                  40                  45
Val Gly Val Pro Gly Val Gly Val Pro Gly Val Gly Ala Gly Ala
            50                  55                  60
Gly Ser Gly Ala Gly Ala Gly Ser Gly Ala Gly Ala Gly Ser Gly Ala
65                  70                  75                  80
Gly Ala Gly Ser Gly Ala Gly Ala Gly Ser Gly Ala Gly Ala Gly Ser
                85                  90                  95
Gly Ala Gly Ala Gly Ser Gly Ala Gly Ala Gly Ser Val Pro Gly Val
```

```
              100                 105                 110
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
            130                 135                 140
Pro Gly Val Gly Val Pro Gly Val Gly Val Pro Gly Val Gly Val Pro
145                 150                 155                 160
Gly Val Gly Val Pro Gly Val Gly Ala Gly Ala Gly Ser Gly Ala
            165                 170                 175
Gly Ala Gly Ser Gly Ala Gly Ala Gly Ser Gly Ala Gly Ala Gly Ser
            180                 185                 190
Gly Ala Gly Ala Gly Ser Gly Ala Gly Ala Gly Ser Gly Ala Gly Ala
            195                 200                 205
Gly Ser Gly Ala Gly Ala Gly Ser Val Pro Gly Val Gly Val Pro Gly
            210                 215                 220
Val Gly Val Pro Gly Val Gly Val Pro Gly Val Gly Val Pro Gly Val
225                 230                 235                 240
Gly Val Pro Gly Val Gly Val Pro Gly Val Gly Val Pro Gly Val Gly
            245                 250                 255
Val Pro Gly Val Gly Val Pro Gly Val Gly Val Pro Gly Val Gly Val
            260                 265                 270
Pro Gly Val Gly Gly Ala Gly Ala Gly Ser Gly Ala Gly Ala Gly Ser
            275                 280                 285
Gly Ala Gly Ala Gly Ser Gly Ala Gly Ala Gly Ser Gly Ala Gly Ala
            290                 295                 300
Gly Ser Gly Ala Gly Ala Gly Ser Gly Ala Gly Ala Gly Ser Gly Ala
305                 310                 315                 320
Gly Ala Gly Ser Val Pro Gly Val Gly Val Pro Gly Val Gly Val Pro
            325                 330                 335
Gly Val Gly Val Pro Gly Val Gly Val Pro Gly Val Gly Val Pro Gly
            340                 345                 350
Val Gly Val Pro Gly Val Gly Val Pro Gly Val Gly Val Pro Gly Val
            355                 360                 365
Gly Val Pro Gly Val Gly Val Pro Gly Val Gly Val Pro Gly Val Gly
            370                 375                 380
Gly Ala Gly Ala Gly Ser Gly Ala Gly Ala Gly Ser Gly Ala Gly Ala
385                 390                 395                 400
Gly Ser Gly Ala Gly Ala Gly Ser Gly Ala Gly Ala Gly Ser Gly Ala
            405                 410                 415
Gly Ala Gly Ser Gly Ala Gly Ala Gly Ser Gly Ala Gly Ala Gly Ser
            420                 425                 430
Val Pro Gly Val Gly Val Pro Gly Val Gly Val Pro Gly Val Gly Val
            435                 440                 445
Pro Gly Val Gly Val Pro Gly Val Gly Val Pro Gly Val Gly Val Pro
            450                 455                 460
Gly Val Gly Val Pro Gly Val Gly Val Pro Gly Val Gly Val Pro Gly
465                 470                 475                 480
Val Gly Val Pro Gly Val Gly Val Pro Gly Val Gly Gly Ala Gly Ala
            485                 490                 495
Gly Ser Gly Ala Gly Ala Gly Ser Gly Ala Gly Ala Gly Ser Gly Ala
            500                 505                 510
Gly Ala Gly Ser Gly Ala Gly Ala Gly Ser Gly Ala Gly Ala Gly Ser
            515                 520                 525
```

-continued

Gly Ala Gly Ala Gly Ser Gly Ala Gly Ala Gly Ser Val Pro Gly Val
            530                 535                 540

Gly Val Pro Gly Val Gly Val Pro Gly Val Gly Val Pro Gly Val Gly
545                 550                 555                 560

Val Pro Gly Val Gly Val Pro Gly Val Gly Val Pro Gly Val Gly Val
            565                 570                 575

Pro Gly Val Gly Val Pro Gly Val Gly Val Pro Gly Val Gly Val Pro
            580                 585                 590

Gly Val Gly Val Pro Gly Val Gly Ala Gly Ala Gly Ser Gly Ala
            595                 600                 605

Gly Ala Gly Ser Gly Ala Gly Ala Gly Ser Gly Ala Gly Ala Gly Ser
            610                 615                 620

Gly Ala Gly Ala Gly Ser Gly Ala Gly Ala Gly Ser Gly Ala Gly Ala
625                 630                 635                 640

Gly Ser Gly Ala Gly Ala Gly Ser Val Pro Gly Val Gly Val Pro Gly
            645                 650                 655

Val Gly Val Pro Gly Val Gly Val Pro Gly Val Gly Val Pro Gly Val
            660                 665                 670

Gly Val Pro Gly Val Gly Val Pro Gly Val Gly Val Pro Gly Val Gly
            675                 680                 685

Val Pro Gly Val Gly Val Pro Gly Val Gly Val Pro Gly Val Gly Val
            690                 695                 700

Pro Gly Val Gly Gly Ala Gly Ala Gly Ser Gly Ala Gly Ala Gly Ser
705                 710                 715                 720

Gly Ala Gly Ala Gly Ser Gly Ala Gly Ala Gly Ser Gly Ala Gly Ala
            725                 730                 735

Gly Ser Gly Ala Gly Ala Gly Ser Gly Ala Gly Ala Gly Ser Gly Ala
            740                 745                 750

Gly Ala Gly Ser Val Pro Gly Val Gly Val Pro Gly Val Gly Val Pro
            755                 760                 765

Gly Val Gly Val Pro Gly Val Gly Val Pro Gly Val Gly Val Pro Gly
            770                 775                 780

Val Gly Val Pro Gly Val Gly Val Pro Gly Val Gly Val Pro Gly Val
785                 790                 795                 800

Gly Val Pro Gly Val Gly Val Pro Gly Val Gly Val Pro Gly Val Gly
            805                 810                 815

Gly Ala Gly Ala Gly Ser Gly Ala Gly Ala Gly Ser Gly Ala Gly Ala
            820                 825                 830

Gly Ser Gly Ala Gly Ala Gly Ser Gly Ala Gly Ala Gly Ser Gly Ala
            835                 840                 845

Gly Ala Gly Ser Gly Ala Gly Ala Gly Ser Gly Ala Gly Ala Gly Ser
            850                 855                 860

<210> SEQ ID NO 9
<211> LENGTH: 896
<212> TYPE: PRT
<213> ORGANISM: Artificial sequence
<220> FEATURE:
<223> OTHER INFORMATION: Synthetic construct

<400> SEQUENCE: 9

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
            35                  40                  45

Val Gly Val Pro Gly Val Gly Val Pro Gly Val Gly Val Pro Gly Val
 50                  55                  60

Gly Val Pro Gly Val Gly Val Pro Gly Val Gly Val Pro Gly Val Gly
 65                  70                  75                  80

Gly Ala Gly Ala Gly Ser Gly Ala Gly Ala Gly Ser Gly Ala Gly Ala
            85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
            115                 120                 125

Val Pro Gly Val Gly Val Pro Gly Val Gly Val Pro Gly Val Gly Val
            130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
            165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
            195                 200                 205

Gly Ala Gly Ala Gly Ser Gly Ala Gly Ala Gly Ser Gly Ala Gly Ala
            210                 215                 220

Gly Ser Gly Ala Gly Ala Gly Ser Gly Ala Gly Ala Gly Ser Gly Ala
225                 230                 235                 240

Gly Ala Gly Ser Gly Ala Gly Ala Gly Ser Gly Ala Gly Ala Gly Ser
            245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
            275                 280                 285

Gly Val Gly Val Pro Gly Val Gly Val Pro Gly Val Gly Val Pro Gly
            290                 295                 300

Val Gly Val Pro Gly Val Gly Val Pro Gly Val Gly Val Pro Gly Val
305                 310                 315                 320

Gly Val Pro Gly Val Gly Val Pro Gly Val Gly Val Pro Gly Val Gly
            325                 330                 335

Gly Ala Gly Ala Gly Ser Gly Ala Gly Ala Gly Ser Gly Ala Gly Ala
            340                 345                 350

Gly Ser Gly Ala Gly Ala Gly Ser Gly Ala Gly Ala Gly Ser Gly Ala
            355                 360                 365

Gly Ala Gly Ser Gly Ala Gly Ala Gly Ser Gly Ala Gly Ala Gly Ser
            370                 375                 380

Val Pro Gly Val Gly Val Pro Gly Val Gly Val Pro Gly Val Gly Val
385                 390                 395                 400

Pro Gly Val Gly Val Pro Gly Val Gly Val Pro Gly Val Gly Val Pro
            405                 410                 415

Gly Val Gly Val Pro Gly Val Gly Val Pro Gly Val Gly Val Pro Gly
            420                 425                 430

Val Gly Val Pro Gly Val Gly Val Pro Gly Val Gly Val Pro Gly Val
            435                 440                 445

```
Gly Val Pro Gly Val Gly Val Pro Gly Val Gly Val Pro Gly Val Gly
    450                 455                 460
Gly Ala Gly Ala Gly Ser Gly Ala Gly Ala Gly Ser Gly Ala Gly Ala
465                 470                 475                 480
Gly Ser Gly Ala Gly Ala Gly Ser Gly Ala Gly Ala Gly Ser Gly Ala
                485                 490                 495
Gly Ala Gly Ser Gly Ala Gly Ala Gly Ser Gly Ala Gly Ala Gly Ser
            500                 505                 510
Val Pro Gly Val Gly Val Pro Gly Val Gly Val Pro Gly Val Gly Val
        515                 520                 525
Pro Gly Val Gly Val Pro Gly Val Gly Val Pro Gly Val Gly Val Pro
    530                 535                 540
Gly Val Gly Val Pro Gly Val Gly Val Pro Gly Val Gly Val Pro Gly
545                 550                 555                 560
Val Gly Val Pro Gly Val Gly Val Pro Gly Val Gly Val Pro Gly Val
                565                 570                 575
Gly Val Pro Gly Val Gly Val Pro Gly Val Gly Val Pro Gly Val Gly
            580                 585                 590
Gly Ala Gly Ala Gly Ser Gly Ala Gly Ala Gly Ser Gly Ala Gly Ala
        595                 600                 605
Gly Ser Gly Ala Gly Ala Gly Ser Gly Ala Gly Ala Gly Ser Gly Ala
    610                 615                 620
Gly Ala Gly Ser Gly Ala Gly Ala Gly Ser Gly Ala Gly Ala Gly Ser
625                 630                 635                 640
Val Pro Gly Val Gly Val Pro Gly Val Gly Val Pro Gly Val Gly Val
                645                 650                 655
Pro Gly Val Gly Val Pro Gly Val Gly Val Pro Gly Val Gly Val Pro
            660                 665                 670
Gly Val Gly Val Pro Gly Val Gly Val Pro Gly Val Gly Val Pro Gly
        675                 680                 685
Val Gly Val Pro Gly Val Gly Val Pro Gly Val Gly Val Pro Gly Val
    690                 695                 700
Gly Val Pro Gly Val Gly Val Pro Gly Val Gly Val Pro Gly Val Gly
705                 710                 715                 720
Gly Ala Gly Ala Gly Ser Gly Ala Gly Ala Gly Ser Gly Ala Gly Ala
                725                 730                 735
Gly Ser Gly Ala Gly Ala Gly Ser Gly Ala Gly Ala Gly Ser Gly Ala
            740                 745                 750
Gly Ala Gly Ser Gly Ala Gly Ala Gly Ser Gly Ala Gly Ala Gly Ser
        755                 760                 765
Val Pro Gly Val Gly Val Pro Gly Val Gly Val Pro Gly Val Gly Val
    770                 775                 780
Pro Gly Val Gly Val Pro Gly Val Gly Val Pro Gly Val Gly Val Pro
785                 790                 795                 800
Gly Val Gly Val Pro Gly Val Gly Val Pro Gly Val Gly Val Pro Gly
                805                 810                 815
Val Gly Val Pro Gly Val Gly Val Pro Gly Val Gly Val Pro Gly Val
            820                 825                 830
Gly Val Pro Gly Val Gly Val Pro Gly Val Gly Val Pro Gly Val Gly
        835                 840                 845
Gly Ala Gly Ala Gly Ser Gly Ala Gly Ala Gly Ser Gly Ala Gly Ala
    850                 855                 860
Gly Ser Gly Ala Gly Ala Gly Ser Gly Ala Gly Ala Gly Ser Gly Ala
```

Gly Ala Gly Ser Gly Ala Gly Ala Gly Ser
        865                 870                 875                 880
Gly Ala Gly Ser Gly Ala Gly Ala Gly Ser
                885                 890                 895

<210> SEQ ID NO 10
<211> LENGTH: 1040
<212> TYPE: PRT
<213> ORGANISM: Artificial sequence
<220> FEATURE:
<223> OTHER INFORMATION: Synthetic construct

<400> SEQUENCE: 10

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
            20                  25                  30
Gly Val Gly Val Pro Gly Val Gly Val Pro Gly Val Gly Val Pro Gly
        35                  40                  45
Val Gly Val Pro Gly Val Gly Val Pro Gly Val Gly Val Pro Gly Val
    50                  55                  60
Gly Val Pro Gly Val Gly Val Pro Gly Val Gly Val Pro Gly Val Gly
65                  70                  75                  80
Val Pro Gly Val Gly Val Pro Gly Val Gly Val Pro Gly Val Gly Val
                85                  90                  95
Pro Gly Val Gly Val Pro Gly Val Gly Val Pro Gly Val Gly Val Pro
            100                 105                 110
Gly Val Gly Val Pro Gly Val Gly Val Pro Gly Val Gly Val Pro Gly
        115                 120                 125
Val Gly Val Pro Gly Val Gly Val Pro Gly Val Gly Val Pro Gly Val
    130                 135                 140
Gly Val Pro Gly Val Gly Val Pro Gly Val Gly Val Pro Gly Val Gly
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
            180                 185                 190
Gly Ala Gly Ser Gly Ala Gly Ala Gly Ser Gly Ala Gly Ala Gly Ser
        195                 200                 205
Val Pro Gly Val Gly Val Pro Gly Val Gly Val Pro Gly Val Gly Val
    210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
            260                 265                 270
Gly Val Pro Gly Val Gly Val Pro Gly Val Gly Val Pro Gly Val Gly
        275                 280                 285
Val Pro Gly Val Gly Val Pro Gly Val Gly Val Pro Gly Val Gly Val
    290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
                325                 330                 335
Val Gly Val Pro Gly Val Gly Val Pro Gly Val Gly Val Pro Gly Val

```
                340                 345                 350
Gly Val Pro Gly Val Gly Val Pro Gly Val Gly Val Pro Gly Val Gly
            355                 360                 365
Gly Ala Gly Ala Gly Ser Gly Ala Gly Ala Gly Ser Gly Ala Gly Ala
            370                 375                 380
Gly Ser Gly Ala Gly Ala Gly Ser Gly Ala Gly Ala Gly Ser Gly Ala
385                 390                 395                 400
Gly Ala Gly Ser Gly Ala Gly Ala Gly Ser Gly Ala Gly Ala Gly Ser
                405                 410                 415
Val Pro Gly Val Gly Val Pro Gly Val Gly Val Pro Gly Val Gly Val
            420                 425                 430
Pro Gly Val Gly Val Pro Gly Val Gly Val Pro Gly Val Gly Val Pro
            435                 440                 445
Gly Val Gly Val Pro Gly Val Gly Val Pro Gly Val Gly Val Pro Gly
            450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
                485                 490                 495
Val Pro Gly Val Gly Val Pro Gly Val Gly Val Pro Gly Val Gly Val
            500                 505                 510
Pro Gly Val Gly Val Pro Gly Val Gly Val Pro Gly Val Gly Val Pro
            515                 520                 525
Gly Val Gly Val Pro Gly Val Gly Val Pro Gly Val Gly Val Pro Gly
            530                 535                 540
Val Gly Val Pro Gly Val Gly Val Pro Gly Val Gly Val Pro Gly Val
545                 550                 555                 560
Gly Val Pro Gly Val Gly Val Pro Gly Val Gly Val Pro Gly Val Gly
                565                 570                 575
Gly Ala Gly Ala Gly Ser Gly Ala Gly Ala Gly Ser Gly Ala Gly Ala
            580                 585                 590
Gly Ser Gly Ala Gly Ala Gly Ser Gly Ala Gly Ala Gly Ser Gly Ala
            595                 600                 605
Gly Ala Gly Ser Gly Ala Gly Ala Gly Ser Gly Ala Gly Ala Gly Ser
            610                 615                 620
Val Pro Gly Val Gly Val Pro Gly Val Gly Val Pro Gly Val Gly Val
625                 630                 635                 640
Pro Gly Val Gly Val Pro Gly Val Gly Val Pro Gly Val Gly Val Pro
                645                 650                 655
Gly Val Gly Val Pro Gly Val Gly Val Pro Gly Val Gly Val Pro Gly
            660                 665                 670
Val Gly Val Pro Gly Val Gly Val Pro Gly Val Gly Val Pro Gly Val
            675                 680                 685
Gly Val Pro Gly Val Gly Val Pro Gly Val Gly Val Pro Gly Val Gly
            690                 695                 700
Val Pro Gly Val Gly Val Pro Gly Val Gly Val Pro Gly Val Gly Val
705                 710                 715                 720
Pro Gly Val Gly Val Pro Gly Val Gly Val Pro Gly Val Gly Val Pro
                725                 730                 735
Gly Val Gly Val Pro Gly Val Gly Val Pro Gly Val Gly Val Pro Gly
            740                 745                 750
Val Gly Val Pro Gly Val Gly Val Pro Gly Val Gly Val Pro Gly Val
            755                 760                 765
```

-continued

```
Gly Val Pro Gly Val Gly Val Pro Gly Val Gly Val Pro Gly Val Gly
            770                 775                 780
Gly Ala Gly Ala Gly Ser Gly Ala Gly Ala Gly Ser Gly Ala Gly Ala
785                 790                 795                 800
Gly Ser Gly Ala Gly Ala Gly Ser Gly Ala Gly Ala Gly Ser Gly Ala
                805                 810                 815
Gly Ala Gly Ser Gly Ala Gly Ala Gly Ser Gly Ala Gly Ala Gly Ser
            820                 825                 830
Val Pro Gly Val Gly Val Pro Gly Val Gly Val Pro Gly Val Gly Val
            835                 840                 845
Pro Gly Val Gly Val Pro Gly Val Gly Val Pro Gly Val Gly Val Pro
            850                 855                 860
Gly Val Gly Val Pro Gly Val Gly Val Pro Gly Val Gly Val Pro Gly
865                 870                 875                 880
Val Gly Val Pro Gly Val Gly Val Pro Gly Val Gly Val Pro Gly Val
                885                 890                 895
Gly Val Pro Gly Val Gly Val Pro Gly Val Gly Val Pro Gly Val Gly
            900                 905                 910
Val Pro Gly Val Gly Val Pro Gly Val Gly Val Pro Gly Val Gly Val
            915                 920                 925
Pro Gly Val Gly Val Pro Gly Val Gly Val Pro Gly Val Gly Val Pro
            930                 935                 940
Gly Val Gly Val Pro Gly Val Gly Val Pro Gly Val Gly Val Pro Gly
945                 950                 955                 960
Val Gly Val Pro Gly Val Gly Val Pro Gly Val Gly Val Pro Gly Val
                965                 970                 975
Gly Val Pro Gly Val Gly Val Pro Gly Val Gly Val Pro Gly Val Gly
            980                 985                 990
Gly Ala Gly Ala Gly Ser Gly Ala  Gly Ala Gly Ser Gly  Ala Gly Ala
            995                 1000                1005
Gly Ser  Gly Ala Gly Ala Gly  Ser Gly Ala Gly Ala  Gly Ser Gly
    1010                1015                1020
Ala Gly  Ala Gly Ser Gly Ala  Gly Ala Gly Ser Gly  Ala Gly Ala
    1025                1030                1035
Gly Ser
    1040

<210> SEQ ID NO 11
<211> LENGTH: 1002
<212> TYPE: PRT
<213> ORGANISM: Artificial sequence
<220> FEATURE:
<223> OTHER INFORMATION: Synthetic construct

<400> SEQUENCE: 11

Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
            20                  25                  30
Gly Ala Gly Ser Gly Ala Gly Ala Gly Ser Gly Ala Gly Ala Gly Ser
        35                  40                  45
Gly Ala Gly Ala Gly Ser Gly Ala Gly Ala Gly Ser Gly Ala Gly Ala
    50                  55                  60
Gly Ser Gly Ala Gly Ala Gly Ser Gly Ala Ala Val Thr Gly Arg Gly
65                  70                  75                  80
```

```
Asp Ser Pro Ala Ser Ala Ala Gly Tyr Gly Ala Gly Ala Gly Ser Gly
                85                  90                  95

Ala Gly Ala Gly Ser Gly Ala Gly Ala Gly Ser Gly Ala Gly Ala Gly
            100                 105                 110

Ser Gly Ala Gly Ala Gly Ser Gly Val Gly Val Gly Pro Gly Val Gly
        115                 120                 125

Val Gly Pro Gly Val Val Gly Pro Gly Val Gly Val Gly Pro Gly Val
    130                 135                 140

Gly Val Gly Pro Gly Val Gly Val Gly Pro Gly Val Gly Val Gly Pro
145                 150                 155                 160

Pro Gly Val Gly Val Gly Pro Gly Ala Gly Ala Gly Ser Gly Ala Gly
            165                 170                 175

Ala Gly Ser Gly Ala Gly Ala Gly Ser Gly Ala Gly Ala Gly Ser Gly
        180                 185                 190

Ala Gly Ala Gly Ser Gly Ala Gly Ala Gly Ser Gly Ala Gly Ala Gly
        195                 200                 205

Ser Gly Ala Gly Ala Gly Ser Gly Ala Gly Ala Gly Ser Gly Ala Gly
        210                 215                 220

Ala Gly Ser Gly Ala Gly Ala Gly Ser Gly Ala Gly Ala Gly Ser Gly
225                 230                 235                 240

Ala Ala Val Thr Gly Arg Gly Asp Ser Pro Ala Ser Ala Ala Gly Tyr
            245                 250                 255

Gly Ala Gly Ala Gly Ser Gly Ala Gly Ala Gly Ser Gly Ala Gly Ala
            260                 265                 270

Gly Ser Gly Ala Gly Ala Gly Ser Gly Ala Gly Ala Gly Ser Gly Val
        275                 280                 285

Gly Val Gly Pro Gly Val Gly Val Gly Pro Gly Val Gly Val Gly Pro
    290                 295                 300

Gly Val Gly Val Gly Pro Gly Val Gly Val Gly Pro Gly Val Gly Val
305                 310                 315                 320

Gly Pro Gly Val Gly Val Gly Pro Gly Val Gly Val Gly Pro Gly Ala
            325                 330                 335

Gly Ala Gly Ser Gly Ala Gly Ala Gly Ser Gly Ala Gly Ala Gly Ser
            340                 345                 350

Gly Ala Gly Ala Gly Ser Gly Ala Gly Ala Gly Ser Gly Ala Gly Ala
        355                 360                 365

Gly Ser Gly Ala Gly Ala Gly Ser Gly Ala Gly Ala Gly Ser Gly Ala
        370                 375                 380

Gly Ala Gly Ser Gly Ala Gly Ala Gly Ser Gly Ala Gly Ala Gly Ser
385                 390                 395                 400

Gly Ala Gly Ala Gly Ser Gly Ala Ala Val Thr Gly Arg Gly Asp Ser
            405                 410                 415

Pro Ala Ser Ala Ala Gly Tyr Gly Ala Gly Ala Gly Ser Gly Ala Gly
            420                 425                 430

Ala Gly Ser Gly Ala Gly Ala Gly Ser Gly Ala Gly Ala Gly Ser Gly
        435                 440                 445

Ala Gly Ala Gly Ser Gly Val Gly Val Gly Pro Gly Val Gly Val Gly
        450                 455                 460

Pro Gly Val Gly Val Gly Pro Gly Val Gly Val Gly Pro Gly Val Gly
465                 470                 475                 480

Val Gly Pro Gly Val Gly Val Gly Pro Gly Val Gly Val Gly Pro Gly
            485                 490                 495
```

-continued

```
Val Gly Val Gly Pro Gly Ala Gly Ser Gly Ala Gly
            500             505             510

Ser Gly Ala Gly Ala Gly Ser Gly Ala Gly Ser Gly Ala Gly
            515             520             525

Ala Gly Ser Gly Ala Gly Ala Gly Ser Gly Ala Gly Ala Gly Ser Gly
            530             535             540

Ala Gly Ala Gly Ser Gly Ala Gly Ala Gly Ser Gly Ala Gly Ala Gly
545             550             555             560

Ser Gly Ala Gly Ala Gly Ser Gly Ala Gly Ala Gly Ser Gly Ala Ala
                565             570             575

Val Thr Gly Arg Gly Asp Ser Pro Ala Ser Ala Ala Gly Tyr Gly Ala
            580             585             590

Gly Ala Gly Ser Gly Ala Gly Ala Gly Ser Gly Ala Gly Ala Gly Ser
            595             600             605

Gly Ala Gly Ala Gly Ser Gly Ala Gly Ala Gly Ser Gly Val Gly Val
            610             615             620

Gly Pro Gly Val Gly Val Gly Pro Gly Val Gly Val Gly Pro Gly Val
625             630             635             640

Gly Val Gly Pro Gly Val Gly Val Gly Pro Gly Val Gly Val Gly Pro
                645             650             655

Gly Val Gly Val Gly Pro Gly Val Gly Val Gly Pro Gly Ala Gly Ala
            660             665             670

Gly Ser Gly Ala Gly Ala Gly Ser Gly Ala Gly Ala Gly Ser Gly Ala
            675             680             685

Gly Ala Gly Ser Gly Ala Gly Ala Gly Ser Gly Ala Gly Ala Gly Ser
            690             695             700

Gly Ala Gly Ala Gly Ser Gly Ala Gly Ala Gly Ser Gly Ala Gly Ala
705             710             715             720

Gly Ser Gly Ala Gly Ala Gly Ser Gly Ala Gly Ala Gly Ser Gly Ala
                725             730             735

Gly Ala Gly Ser Gly Ala Ala Val Thr Gly Arg Gly Asp Ser Pro Ala
            740             745             750

Ser Ala Ala Gly Tyr Gly Ala Gly Ala Gly Ser Gly Ala Gly Ala Gly
            755             760             765

Ser Gly Ala Gly Ala Gly Ser Gly Ala Gly Ala Gly Ser Gly Ala Gly
            770             775             780

Ala Gly Ser Gly Val Gly Val Gly Pro Gly Val Gly Val Gly Pro Gly
785             790             795             800

Val Gly Val Gly Pro Gly Val Gly Val Gly Pro Gly Val Gly Val Gly
                805             810             815

Pro Gly Val Gly Val Gly Pro Gly Val Gly Val Gly Pro Gly Val Gly
            820             825             830

Val Gly Pro Gly Ala Gly Ala Gly Ser Gly Ala Gly Ala Gly Ser Gly
            835             840             845

Ala Gly Ala Gly Ser Gly Ala Gly Ala Gly Ser Gly Ala Gly Ala Gly
            850             855             860

Ser Gly Ala Gly Ala Gly Ser Gly Ala Gly Ala Gly Ser Gly Ala Gly
865             870             875             880

Ala Gly Ser Gly Ala Gly Ala Gly Ser Gly Ala Gly Ala Gly Ser Gly
                885             890             895

Ala Gly Ala Gly Ser Gly Ala Gly Ala Gly Ser Gly Ala Ala Val Thr
            900             905             910

Gly Arg Gly Asp Ser Pro Ala Ser Ala Ala Gly Tyr Gly Ala Gly Ala
```

```
            915                 920                 925
Gly Ser Gly Ala Gly Ala Gly Ser Gly Ala Gly Ser Gly Ala
            930                 935                 940

Gly Ala Gly Ser Gly Ala Gly Ala Gly Ser Gly Val Gly Val Gly Pro
945                 950                 955                 960

Gly Val Gly Val Gly Pro Gly Val Gly Val Pro Gly Val Gly Val
                965                 970                 975

Gly Pro Gly Val Gly Val Gly Pro Gly Val Gly Val Pro Gly Val
            980                 985                 990

Gly Val Gly Pro Gly Val Gly Val  Gly Pro
            995                 1000

<210> SEQ ID NO 12
<211> LENGTH: 312
<212> TYPE: PRT
<213> ORGANISM: Artificial sequence
<220> FEATURE:
<223> OTHER INFORMATION: Synthetic construct

<400> SEQUENCE: 12

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
                20                  25                  30

Gly Lys Gly Val Pro Gly Val Gly Val Pro Gly Val Gly Val Pro Gly
            35                  40                  45

Val Gly Val Pro Gly Ala Gly Ala Gly Ser Gly Ala Gly Ala Gly Ser
        50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
        115                 120                 125

Gly Val Pro Gly Val Gly Val Pro Gly Lys Gly Val Pro Gly Val Gly
    130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val Gly
                165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
        195                 200                 205

Gly Ala Gly Ala Gly Ser Gly Ala Gly Ala Gly Ser Gly Val Gly Val
    210                 215                 220

Pro Gly Val Gly Val Pro Gly Val Gly Val Pro Gly Val Gly Val Pro
225                 230                 235                 240

Gly Lys Gly Val Pro Gly Val Gly Val Pro Gly Val Gly Val Pro Gly
                245                 250                 255

Val Gly Val Pro Gly Ala Gly Ala Gly Ser Gly Ala Gly Ala Gly Ser
            260                 265                 270

Gly Val Gly Val Pro Gly Val Gly Val Pro Gly Val Gly Val Pro Gly
```

```
                275                 280                 285
Val Gly Val Pro Gly Lys Gly Val Pro Gly Val Gly Val Pro Gly Val
        290                 295                 300

Gly Val Pro Gly Val Gly Val Pro
305                 310

<210> SEQ ID NO 13
<211> LENGTH: 624
<212> TYPE: PRT
<213> ORGANISM: Artificial sequence
<220> FEATURE:
<223> OTHER INFORMATION: Synthetic construct

<400> SEQUENCE: 13

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
                20                  25                  30

Gly Lys Gly Val Pro Gly Val Gly Val Pro Gly Val Gly Val Pro Gly
        35                  40                  45

Val Gly Val Pro Gly Ala Gly Ala Gly Ser Gly Ala Gly Ala Gly Ser
50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
        115                 120                 125

Gly Val Pro Gly Val Gly Val Pro Gly Lys Gly Val Pro Gly Val Gly
    130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val Gly
                165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
        195                 200                 205

Gly Ala Gly Ala Gly Ser Gly Ala Gly Ala Gly Ser Gly Val Gly Val
    210                 215                 220

Pro Gly Val Gly Val Pro Gly Val Gly Val Pro Gly Val Gly Val Pro
225                 230                 235                 240

Gly Lys Gly Val Pro Gly Val Gly Val Pro Gly Val Gly Val Pro Gly
                245                 250                 255

Val Gly Val Pro Gly Ala Gly Ala Gly Ser Gly Ala Gly Ala Gly Ser
            260                 265                 270

Gly Val Gly Val Pro Gly Val Gly Val Pro Gly Val Gly Val Pro Gly
        275                 280                 285

Val Gly Val Pro Gly Lys Gly Val Pro Gly Val Gly Val Pro Gly Val
    290                 295                 300

Gly Val Pro Gly Val Gly Val Pro Gly Ala Gly Ala Gly Ser Gly Ala
305                 310                 315                 320

Gly Ala Gly Ser Gly Val Gly Val Pro Gly Val Gly Val Pro Gly Val
```

```
                    325                 330                 335
Gly Val Pro Gly Val Gly Val Pro Gly Lys Gly Val Pro Gly Val Gly
                340                 345                 350
Val Pro Gly Val Gly Val Pro Gly Val Gly Val Pro Gly Ala Gly Ala
                355                 360                 365
Gly Ser Gly Ala Gly Ala Gly Ser Gly Val Gly Val Pro Gly Val Gly
                370                 375                 380
Val Pro Gly Val Gly Val Pro Gly Val Gly Val Pro Gly Lys Gly Val
385                 390                 395                 400
Pro Gly Val Gly Val Pro Gly Val Gly Val Pro Gly Val Gly Val Pro
                405                 410                 415
Gly Ala Gly Ala Gly Ser Gly Ala Gly Ala Gly Ser Gly Val Gly Val
                420                 425                 430
Pro Gly Val Gly Val Pro Gly Val Gly Val Pro Gly Val Gly Val Pro
                435                 440                 445
Gly Lys Gly Val Pro Gly Val Gly Val Pro Gly Val Gly Val Pro Gly
                450                 455                 460
Val Gly Val Pro Gly Ala Gly Ala Gly Ser Gly Ala Gly Ala Gly Ser
465                 470                 475                 480
Gly Val Gly Val Pro Gly Val Gly Val Pro Gly Val Gly Val Pro Gly
                485                 490                 495
Val Gly Val Pro Gly Lys Gly Val Pro Gly Val Gly Val Pro Gly Val
                500                 505                 510
Gly Val Pro Gly Val Gly Val Pro Gly Ala Gly Ala Gly Ser Gly Ala
                515                 520                 525
Gly Ala Gly Ser Gly Val Gly Val Pro Gly Val Gly Val Pro Gly Val
                530                 535                 540
Gly Val Pro Gly Val Gly Val Pro Gly Lys Val Pro Gly Val Gly
545                 550                 555                 560
Val Pro Gly Val Gly Val Pro Gly Val Gly Val Pro Gly Ala Gly Ala
                565                 570                 575
Gly Ser Gly Ala Gly Ala Gly Ser Gly Val Gly Val Pro Gly Val Gly
                580                 585                 590
Val Pro Gly Val Gly Val Pro Gly Val Gly Val Pro Gly Lys Gly Val
                595                 600                 605
Pro Gly Val Gly Val Pro Gly Val Gly Val Pro Gly Val Gly Val Pro
            610                 615                 620
```

<210> SEQ ID NO 14
<211> LENGTH: 936
<212> TYPE: PRT
<213> ORGANISM: Artificial sequence
<220> FEATURE:
<223> OTHER INFORMATION: Synthetic construct

<400> SEQUENCE: 14

```
Gly Ala Gly Ala Gly Ser Gly Ala Gly Ala Gly Ser Gly Val Gly Val
1               5                   10                  15
Pro Gly Val Gly Val Pro Gly Val Gly Val Pro Gly Val Gly Val Pro
                20                  25                  30
Gly Lys Gly Val Pro Gly Val Gly Val Pro Gly Val Gly Val Pro Gly
                35                  40                  45
Val Gly Val Pro Gly Ala Gly Ala Gly Ser Gly Ala Gly Ala Gly Ser
                50                  55                  60
Gly Val Gly Val Pro Gly Val Gly Val Pro Gly Val Gly Val Pro Gly
```

```
                65                  70                  75                  80
Val Gly Val Pro Gly Lys Gly Val Pro Gly Val Gly Val Pro Gly Val
                    85                  90                  95
Gly Val Pro Gly Val Gly Val Pro Gly Ala Gly Ala Gly Ser Gly Ala
                    100                 105                 110
Gly Ala Gly Ser Gly Val Gly Val Pro Gly Val Gly Val Pro Gly Val
                    115                 120                 125
Gly Val Pro Gly Val Gly Val Pro Gly Lys Gly Val Pro Gly Val Gly
                    130                 135                 140
Val Pro Gly Val Gly Val Pro Gly Val Gly Val Pro Gly Ala Gly Ala
145                 150                 155                 160
Gly Ser Gly Ala Gly Ala Gly Ser Gly Val Gly Val Pro Gly Val Gly
                    165                 170                 175
Val Pro Gly Val Gly Val Pro Gly Val Gly Val Pro Gly Lys Gly Val
                    180                 185                 190
Pro Gly Val Gly Val Pro Gly Val Gly Val Pro Gly Val Gly Val Pro
                    195                 200                 205
Gly Ala Gly Ala Gly Ser Gly Ala Gly Ala Gly Ser Gly Val Gly Val
                    210                 215                 220
Pro Gly Val Gly Val Pro Gly Val Gly Val Pro Gly Val Gly Val Pro
225                 230                 235                 240
Gly Lys Gly Val Pro Gly Val Gly Val Pro Gly Val Gly Val Pro Gly
                    245                 250                 255
Val Gly Val Pro Gly Ala Gly Ala Gly Ser Gly Ala Gly Ala Gly Ser
                    260                 265                 270
Gly Val Gly Val Pro Gly Val Gly Val Pro Gly Val Gly Val Pro Gly
                    275                 280                 285
Val Gly Val Pro Gly Lys Gly Val Pro Gly Val Gly Val Pro Gly Val
                    290                 295                 300
Gly Val Pro Gly Val Gly Val Pro Gly Ala Gly Ala Gly Ser Gly Ala
305                 310                 315                 320
Gly Ala Gly Ser Gly Val Gly Val Pro Gly Val Gly Val Pro Gly Val
                    325                 330                 335
Gly Val Pro Gly Val Gly Val Pro Gly Lys Gly Val Pro Gly Val Gly
                    340                 345                 350
Val Pro Gly Val Gly Val Pro Gly Val Gly Val Pro Gly Ala Gly Ala
                    355                 360                 365
Gly Ser Gly Ala Gly Ala Gly Ser Gly Val Gly Val Pro Gly Val Gly
                    370                 375                 380
Val Pro Gly Val Gly Val Pro Gly Val Gly Val Pro Gly Lys Gly Val
385                 390                 395                 400
Pro Gly Val Gly Val Pro Gly Val Gly Val Pro Gly Val Gly Val Pro
                    405                 410                 415
Gly Ala Gly Ala Gly Ser Gly Ala Gly Ala Gly Ser Gly Val Gly Val
                    420                 425                 430
Pro Gly Val Gly Val Pro Gly Val Gly Val Pro Gly Val Gly Val Pro
                    435                 440                 445
Gly Lys Gly Val Pro Gly Val Gly Val Pro Gly Val Gly Val Pro Gly
                    450                 455                 460
Val Gly Val Pro Gly Ala Gly Ala Gly Ser Gly Ala Gly Ala Gly Ser
465                 470                 475                 480
Gly Val Gly Val Pro Gly Val Gly Val Pro Gly Val Gly Val Pro Gly
                    485                 490                 495
```

Val Gly Val Pro Gly Lys Gly Val Pro Gly Val Gly Val
            500                 505                 510

Gly Val Pro Gly Val Gly Val Pro Gly Ala Gly Ala Gly Ser Gly Ala
            515                 520                 525

Gly Ala Gly Ser Gly Val Gly Val Pro Gly Val Gly Val Pro Gly Val
        530                 535                 540

Gly Val Pro Gly Val Gly Val Pro Gly Lys Gly Val Pro Gly Val Gly
545                 550                 555                 560

Val Pro Gly Val Gly Val Pro Gly Val Gly Val Pro Gly Ala Gly Ala
                565                 570                 575

Gly Ser Gly Ala Gly Ala Gly Ser Gly Val Gly Val Pro Gly Val Gly
            580                 585                 590

Val Pro Gly Val Gly Val Pro Gly Val Gly Val Pro Gly Lys Gly Val
            595                 600                 605

Pro Gly Val Gly Val Pro Gly Val Gly Val Pro Gly Val Gly Val Pro
            610                 615                 620

Gly Ala Gly Ala Gly Ser Gly Ala Gly Ala Gly Ser Gly Val Gly Val
625                 630                 635                 640

Pro Gly Val Gly Val Pro Gly Val Gly Val Pro Gly Val Gly Val Pro
            645                 650                 655

Gly Lys Gly Val Pro Gly Val Gly Val Pro Gly Val Gly Val Pro Gly
            660                 665                 670

Val Gly Val Pro Gly Ala Gly Ala Gly Ser Gly Ala Gly Ala Gly Ser
            675                 680                 685

Gly Val Gly Val Pro Gly Val Gly Val Pro Gly Val Gly Val Pro Gly
            690                 695                 700

Val Gly Val Pro Gly Lys Gly Val Pro Gly Val Gly Val Pro Gly Val
705                 710                 715                 720

Gly Val Pro Gly Val Gly Val Pro Gly Ala Gly Ala Gly Ser Gly Ala
            725                 730                 735

Gly Ala Gly Ser Gly Val Gly Val Pro Gly Val Gly Val Pro Gly Val
            740                 745                 750

Gly Val Pro Gly Val Gly Val Pro Gly Lys Gly Val Pro Gly Val Gly
            755                 760                 765

Val Pro Gly Val Gly Val Pro Gly Val Gly Val Pro Gly Ala Gly Ala
770                 775                 780

Gly Ser Gly Ala Gly Ala Gly Ser Gly Val Gly Val Pro Gly Val Gly
785                 790                 795                 800

Val Pro Gly Val Gly Val Pro Gly Val Gly Val Pro Gly Lys Gly Val
            805                 810                 815

Pro Gly Val Gly Val Pro Gly Val Gly Val Pro Gly Val Gly Val Pro
            820                 825                 830

Gly Ala Gly Ala Gly Ser Gly Ala Gly Ala Gly Ser Gly Val Gly Val
835                 840                 845

Pro Gly Val Gly Val Pro Gly Val Gly Val Pro Gly Val Gly Val Pro
            850                 855                 860

Gly Lys Gly Val Pro Gly Val Gly Val Pro Gly Val Gly Val Pro Gly
865                 870                 875                 880

Val Gly Val Pro Gly Ala Gly Ala Gly Ser Gly Ala Gly Ala Gly Ser
                885                 890                 895

Gly Val Gly Val Pro Gly Val Gly Val Pro Gly Val Gly Val Pro Gly
                900                 905                 910

```
Val Gly Val Pro Gly Lys Gly Val Pro Gly Val Gly Val Pro Gly Val
        915                 920                 925

Gly Val Pro Gly Val Gly Val Pro
        930                 935

<210> SEQ ID NO 15
<211> LENGTH: 896
<212> TYPE: PRT
<213> ORGANISM: Artificial sequence
<220> FEATURE:
<223> OTHER INFORMATION: Synthetic construct

<400> SEQUENCE: 15

Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
                20                  25                  30

Gly Lys Gly Val Pro Gly Val Gly Val Pro Gly Val Gly Val Pro Gly
            35                  40                  45

Val Gly Val Pro Gly Ala Gly Ala Gly Ser Gly Ala Gly Ala Gly Ser
        50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110

Gly Ala Gly Ser Gly Val Gly Val Pro Gly Val Gly Val Pro Gly Val
        115                 120                 125

Gly Val Pro Gly Val Gly Val Pro Gly Lys Gly Val Pro Gly Val Gly
    130                 135                 140

Val Pro Gly Val Gly Val Pro Gly Val Gly Val Pro Gly Ala Gly Ala
145                 150                 155                 160

Gly Ser Gly Ala Gly Ala Gly Ser Gly Val Gly Val Pro Gly Val Gly
                165                 170                 175

Val Pro Gly Val Gly Val Pro Gly Val Gly Val Pro Gly Lys Gly Val
            180                 185                 190

Pro Gly Val Gly Val Pro Gly Val Gly Val Pro Gly Val Gly Val Pro
        195                 200                 205

Gly Ala Gly Ala Gly Ser Gly Ala Gly Ala Gly Ser Gly Val Gly Val
    210                 215                 220

Pro Gly Val Gly Val Pro Gly Val Gly Val Pro Gly Val Gly Val Pro
225                 230                 235                 240

Gly Lys Gly Val Pro Gly Val Gly Val Pro Gly Val Gly Val Pro Gly
                245                 250                 255

Val Gly Val Pro Gly Ala Gly Ala Gly Ser Gly Ala Gly Ala Gly Ser
            260                 265                 270

Gly Val Gly Val Pro Gly Val Gly Val Pro Gly Val Gly Val Pro Gly
        275                 280                 285

Val Gly Val Pro Gly Lys Gly Val Pro Gly Val Gly Val Pro Gly Val
    290                 295                 300

Gly Val Pro Gly Val Gly Val Pro Gly Ala Gly Ala Gly Ser Gly Ala
305                 310                 315                 320

Gly Ala Gly Ser Gly Val Gly Val Pro Gly Val Gly Val Pro Gly Val
                325                 330                 335
```

-continued

Gly Val Pro Gly Val Gly Val Pro Gly Lys Gly Val Pro Gly Val Gly
                340                 345                 350

Val Pro Gly Val Gly Val Pro Gly Val Gly Val Pro Gly Ala Gly Ala
            355                 360                 365

Gly Ser Gly Ala Gly Ala Gly Ser Gly Val Gly Val Pro Gly Val Gly
            370                 375                 380

Val Pro Gly Val Gly Val Pro Gly Val Gly Val Pro Gly Lys Gly Val
385                 390                 395                 400

Pro Gly Val Gly Val Pro Gly Val Gly Val Pro Gly Val Gly Val Pro
                405                 410                 415

Gly Ala Gly Ala Gly Ser Gly Ala Gly Ala Gly Ser Gly Val Gly Val
            420                 425                 430

Pro Gly Val Gly Val Pro Gly Val Gly Val Pro Gly Val Gly Val Pro
            435                 440                 445

Gly Lys Gly Val Pro Gly Val Gly Val Pro Gly Val Gly Val Pro Gly
        450                 455                 460

Val Gly Val Pro Gly Ala Gly Ala Gly Ser Gly Ala Gly Ala Gly Ser
465                 470                 475                 480

Gly Val Gly Val Pro Gly Val Gly Val Pro Gly Val Gly Val Pro Gly
            485                 490                 495

Val Gly Val Pro Gly Lys Gly Val Pro Gly Val Gly Val Pro Gly Val
            500                 505                 510

Gly Val Pro Gly Val Gly Val Pro Gly Ala Gly Ala Gly Ser Gly Ala
        515                 520                 525

Gly Ala Gly Ser Gly Val Gly Val Pro Gly Val Gly Val Pro Gly Val
        530                 535                 540

Gly Val Pro Gly Val Gly Val Pro Gly Lys Gly Val Pro Gly Val Gly
545                 550                 555                 560

Val Pro Gly Val Gly Val Pro Gly Val Gly Val Pro Gly Ala Gly Ala
            565                 570                 575

Gly Ser Gly Ala Gly Ala Gly Ser Gly Val Gly Val Pro Gly Val Gly
            580                 585                 590

Val Pro Gly Val Gly Val Pro Gly Val Gly Val Pro Gly Lys Gly Val
            595                 600                 605

Pro Gly Val Gly Val Pro Gly Val Gly Val Pro Gly Val Gly Val Pro
    610                 615                 620

Gly Ala Gly Ala Gly Ser Gly Ala Gly Ala Gly Ser Gly Val Gly Val
625                 630                 635                 640

Pro Gly Val Gly Val Pro Gly Val Gly Val Pro Gly Val Gly Val Pro
            645                 650                 655

Gly Lys Gly Val Pro Gly Val Gly Val Pro Gly Val Gly Val Pro Gly
            660                 665                 670

Val Gly Val Pro Gly Ala Gly Ala Gly Ser Gly Ala Gly Ala Gly Ser
        675                 680                 685

Gly Val Gly Val Pro Gly Val Gly Val Pro Gly Val Gly Val Pro Gly
        690                 695                 700

Val Gly Val Pro Gly Lys Gly Val Pro Gly Val Gly Val Pro Gly Val
705                 710                 715                 720

Gly Val Pro Gly Val Gly Val Pro Gly Ala Gly Ala Gly Ser Gly Ala
            725                 730                 735

Gly Ala Gly Ser Gly Val Gly Val Pro Gly Val Gly Val Pro Gly Val
            740                 745                 750

Gly Val Pro Gly Val Gly Val Pro Gly Lys Gly Val Pro Gly Val Gly

```
                755                 760                 765
Val Pro Gly Val Gly Val Pro Gly Val Gly Val Pro Gly Ala Gly Ala
            770                 775                 780

Gly Ser Gly Ala Gly Ala Gly Ser Gly Val Gly Val Pro Gly Val Gly
785                 790                 795                 800

Val Pro Gly Val Gly Val Pro Gly Val Gly Val Pro Gly Lys Gly Val
                805                 810                 815

Pro Gly Val Gly Val Pro Gly Val Gly Val Pro Gly Val Gly Val Pro
            820                 825                 830

Gly Ala Gly Ala Gly Ser Gly Ala Gly Ala Gly Ser Gly Val Gly Val
            835                 840                 845

Pro Gly Val Gly Val Pro Gly Val Gly Val Pro Gly Val Gly Val Pro
            850                 855                 860

Gly Lys Gly Val Pro Gly Val Gly Val Pro Gly Val Gly Val Pro Gly
865                 870                 875                 880

Val Gly Val Pro Gly Ala Gly Ala Gly Ser Gly Ala Gly Ala Gly Ser
            885                 890                 895
```

<210> SEQ ID NO 16
<211> LENGTH: 64
<212> TYPE: PRT
<213> ORGANISM: Artificial sequence
<220> FEATURE:
<223> OTHER INFORMATION: Synthetic construct

<400> SEQUENCE: 16

```
Gly Ala Gly Ala Gly Ser Gly Ala Gly Ala Gly Ser Gly Val Gly Val
1               5                   10                  15

Pro Gly Val Gly Val Pro Gly Val Gly Val Pro Gly Val Gly Val Pro
            20                  25                  30

Gly Lys Gly Val Pro Gly Val Gly Val Pro Gly Val Gly Val Pro Gly
        35                  40                  45

Val Gly Val Pro Gly Ala Gly Ala Gly Ser Gly Ala Gly Ala Gly Ser
    50                  55                  60
```

<210> SEQ ID NO 17
<211> LENGTH: 696
<212> TYPE: PRT
<213> ORGANISM: Artificial sequence
<220> FEATURE:
<223> OTHER INFORMATION: Synthetic construct

<400> SEQUENCE: 17

```
Gly Ala Gly Ala Gly Ser Gly Val Gly Val Pro Gly Val Gly Val Pro
1               5                   10                  15

Gly Val Gly Val Pro Gly Val Gly Val Pro Gly Lys Gly Val Pro Gly
            20                  25                  30

Val Gly Val Pro Gly Val Gly Val Pro Gly Val Gly Val Pro Gly Ala
        35                  40                  45

Gly Ala Gly Ser Gly Ala Gly Ala Gly Ser Gly Ala Gly Ala Gly Ser
    50                  55                  60

Gly Val Gly Val Pro Gly Val Gly Val Pro Gly Val Gly Val Pro Gly
65                  70                  75                  80

Val Gly Val Pro Gly Lys Gly Val Pro Gly Val Gly Val Pro Gly Val
                85                  90                  95

Gly Val Pro Gly Val Gly Val Pro Gly Ala Gly Ala Gly Ser Gly Ala
            100                 105                 110
```

-continued

Gly Ala Gly Ser Gly Ala Gly Ala Gly Ser Gly Val Gly Val Pro Gly
                115                 120                 125

Val Gly Val Pro Gly Val Gly Val Pro Gly Val Gly Val Pro Gly Lys
        130                 135                 140

Gly Val Pro Gly Val Gly Val Pro Gly Val Gly Val Pro Gly Val Gly
145                 150                 155                 160

Val Pro Gly Ala Gly Ala Gly Ser Gly Ala Gly Ala Gly Ser Gly Ala
                165                 170                 175

Gly Ala Gly Ser Gly Val Gly Val Pro Gly Val Gly Val Pro Gly Val
                180                 185                 190

Gly Val Pro Gly Val Gly Val Pro Gly Lys Gly Val Pro Gly Val Gly
                195                 200                 205

Val Pro Gly Val Gly Val Pro Gly Val Gly Val Pro Gly Ala Gly Ala
        210                 215                 220

Gly Ser Gly Ala Gly Ala Gly Ser Gly Ala Gly Ala Gly Ser Gly Val
225                 230                 235                 240

Gly Val Pro Gly Val Gly Val Pro Gly Val Gly Val Pro Gly Val Gly
                245                 250                 255

Val Pro Gly Lys Gly Val Pro Gly Val Gly Val Pro Gly Val Gly Val
        260                 265                 270

Pro Gly Val Gly Val Pro Gly Ala Gly Ala Gly Ser Gly Ala Gly Ala
            275                 280                 285

Gly Ser Gly Ala Gly Ala Gly Ser Gly Val Gly Val Pro Gly Val Gly
        290                 295                 300

Val Pro Gly Val Gly Val Pro Gly Val Gly Val Pro Gly Lys Gly Val
305                 310                 315                 320

Pro Gly Val Gly Val Pro Gly Val Gly Val Pro Gly Val Gly Val Pro
                325                 330                 335

Gly Ala Gly Ala Gly Ser Gly Ala Gly Ala Gly Ser Gly Ala Gly Ala
                340                 345                 350

Gly Ser Gly Val Gly Val Pro Gly Val Gly Val Pro Gly Val Gly Val
        355                 360                 365

Pro Gly Val Gly Val Pro Gly Lys Gly Val Pro Gly Val Gly Val Pro
370                 375                 380

Gly Val Gly Val Pro Gly Val Gly Val Pro Gly Ala Gly Ala Gly Ser
385                 390                 395                 400

Gly Ala Gly Ala Gly Ser Gly Ala Gly Ala Gly Ser Gly Val Gly Val
                405                 410                 415

Pro Gly Val Gly Val Pro Gly Val Gly Val Pro Gly Val Gly Val Pro
        420                 425                 430

Gly Lys Gly Val Pro Gly Val Gly Val Pro Gly Val Gly Val Pro Gly
        435                 440                 445

Val Gly Val Pro Gly Ala Gly Ala Gly Ser Gly Ala Gly Ala Gly Ser
        450                 455                 460

Gly Ala Gly Ala Gly Ser Gly Val Gly Val Pro Gly Val Gly Val Pro
465                 470                 475                 480

Gly Val Gly Val Pro Gly Val Gly Val Pro Gly Lys Gly Val Pro Gly
                485                 490                 495

Val Gly Val Pro Gly Val Gly Val Pro Gly Val Gly Val Pro Gly Ala
            500                 505                 510

Gly Ala Gly Ser Gly Ala Gly Ala Gly Ser Gly Ala Gly Ala Gly Ser
                515                 520                 525

Gly Val Gly Val Pro Gly Val Gly Val Pro Gly Val Gly Val Pro Gly

```
                530             535             540
Val Gly Val Pro Gly Lys Gly Val Pro Gly Val Gly Val Pro Gly Val
545                 550             555                 560

Gly Val Pro Gly Val Gly Val Pro Gly Ala Gly Ala Gly Ser Gly Ala
                565             570             575

Gly Ala Gly Ser Gly Ala Gly Ala Gly Ser Gly Val Gly Val Pro Gly
            580             585             590

Val Gly Val Pro Gly Val Gly Val Pro Gly Val Gly Val Pro Gly Lys
        595             600             605

Gly Val Pro Gly Val Gly Val Pro Gly Val Gly Val Pro Gly Val Gly
    610             615             620

Val Pro Gly Ala Gly Ala Gly Ser Gly Ala Gly Ala Gly Ser Gly Ala
625             630             635             640

Gly Ala Gly Ser Gly Val Gly Val Pro Gly Val Gly Val Pro Gly Val
            645             650             655

Gly Val Pro Gly Val Gly Val Pro Gly Lys Gly Val Pro Gly Val Gly
        660             665             670

Val Pro Gly Val Gly Val Pro Gly Val Gly Val Pro Gly Ala Gly Ala
    675             680             685

Gly Ser Gly Ala Gly Ala Gly Ser
    690             695

<210> SEQ ID NO 18
<211> LENGTH: 612
<212> TYPE: PRT
<213> ORGANISM: Artificial sequence
<220> FEATURE:
<223> OTHER INFORMATION: Synthetic construct

<400> SEQUENCE: 18

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Val Gly Val Pro Gly Val Gly
            100                 105                 110

Val Pro Gly Val Gly Val Pro Gly Val Gly Val Pro Gly Lys Gly Val
        115                 120                 125

Pro Gly Val Gly Val Pro Gly Val Gly Val Pro Gly Val Gly Val Pro
    130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Ala Gly Ala Gly Ser Gly Ala
            180                 185                 190

Gly Ala Gly Ser Gly Ala Gly Ala Gly Ser Gly Ala Gly Ala Gly Ser
```

```
            195                 200                 205
Gly Val Gly Val Pro Val Gly Val Pro Gly Val Gly Val Pro Gly
            210                 215                 220
Val Gly Val Pro Gly Lys Gly Val Pro Gly Val Gly Val Pro Gly Val
225                 230                 235                 240
Gly Val Pro Gly Val Gly Val Pro Gly Val Gly Val Pro Gly Val Gly
                245                 250                 255
Val Pro Gly Val Gly Val Pro Gly Val Gly Val Pro Gly Val Gly Val
            260                 265                 270
Pro Gly Val Gly Val Pro Gly Val Gly Val Pro Gly Val Gly Val Pro
        275                 280                 285
Gly Ala Gly Ala Gly Ser Gly Ala Gly Ala Gly Ser Gly Ala Gly Ala
        290                 295                 300
Gly Ser Gly Ala Gly Ala Gly Ser Gly Val Gly Val Pro Gly Val Gly
305                 310                 315                 320
Val Pro Gly Val Gly Val Pro Gly Val Gly Val Pro Gly Lys Gly Val
            325                 330                 335
Pro Gly Val Gly Val Pro Gly Val Gly Val Pro Gly Val Gly Val Pro
        340                 345                 350
Gly Val Gly Val Pro Gly Val Gly Val Pro Gly Val Gly Val Pro Gly
        355                 360                 365
Val Gly Val Pro Gly Val Gly Val Pro Gly Val Gly Val Pro Gly Val
        370                 375                 380
Gly Val Pro Gly Val Gly Val Pro Gly Ala Gly Ala Gly Ser Gly Ala
385                 390                 395                 400
Gly Ala Gly Ser Gly Ala Gly Ala Gly Ser Gly Ala Gly Ala Gly Ser
                405                 410                 415
Gly Val Gly Val Pro Gly Val Gly Val Pro Gly Val Gly Val Pro Gly
            420                 425                 430
Val Gly Val Pro Gly Lys Gly Val Pro Gly Val Gly Val Pro Gly Val
            435                 440                 445
Gly Val Pro Gly Val Gly Val Pro Gly Val Gly Val Pro Gly Val Gly
        450                 455                 460
Val Pro Gly Val Gly Val Pro Gly Val Gly Val Pro Gly Val Gly Val
465                 470                 475                 480
Pro Gly Val Gly Val Pro Gly Val Gly Val Pro Gly Val Gly Val Pro
                485                 490                 495
Gly Ala Gly Ala Gly Ser Gly Ala Gly Ala Gly Ser Gly Ala Gly Ala
            500                 505                 510
Gly Ser Gly Ala Gly Ala Gly Ser Gly Val Gly Val Pro Gly Val Gly
        515                 520                 525
Val Pro Gly Val Gly Val Pro Gly Val Gly Val Pro Gly Lys Gly Val
        530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Val Gly Val Pro Gly Val
            580                 585                 590
Gly Val Pro Gly Val Gly Val Pro Gly Ala Gly Ala Gly Ser Gly Ala
            595                 600                 605
Gly Ala Gly Ser
        610
```

<210> SEQ ID NO 19
<211> LENGTH: 820
<212> TYPE: PRT
<213> ORGANISM: Artificial sequence
<220> FEATURE:
<223> OTHER INFORMATION: Synthetic construct

<400> SEQUENCE: 19

```
Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Val Gly Val Pro Gly Val Gly
                100                 105                 110

Val Pro Gly Val Gly Val Pro Gly Val Gly Val Pro Gly Lys Gly Val
            115                 120                 125

Pro Gly Val Gly Val Pro Gly Val Gly Val Pro Gly Val Gly Val Pro
        130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

Gly Val Gly Val Pro Gly Val Gly Val Pro Gly Val Gly Val Pro Gly
    210                 215                 220

Val Gly Val Pro Gly Lys Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Ala Gly Ala Gly Ser Gly Ala Gly Ala Gly Ser Gly Ala Gly Ala
    290                 295                 300

Gly Ser Gly Ala Gly Ala Gly Ser Gly Val Gly Val Pro Gly Val Gly
305                 310                 315                 320

Val Pro Gly Val Gly Val Pro Gly Val Gly Val Pro Gly Lys Gly Val
                325                 330                 335

Pro Gly Val Gly Val Pro Gly Val Gly Val Pro Gly Val Gly Val Pro
            340                 345                 350

Gly Val Gly Val Pro Gly Val Gly Val Pro Gly Val Gly Val Pro Gly
        355                 360                 365
```

```
Val Gly Val Pro Gly Val Gly Val Pro Gly Val Gly Val Pro Gly Val
        370                 375                 380

Gly Val Pro Gly Val Gly Val Pro Gly Ala Gly Ala Gly Ser Gly Ala
385                 390                 395                 400

Gly Ala Gly Ser Gly Ala Gly Ala Gly Ser Gly Ala Gly Ala Gly Ser
            405                 410                 415

Gly Val Gly Val Pro Gly Val Gly Val Pro Gly Val Gly Val Pro Gly
        420                 425                 430

Val Gly Val Pro Gly Lys Gly Val Pro Gly Val Gly Val Pro Gly Val
            435                 440                 445

Gly Val Pro Gly Val Gly Val Pro Gly Val Gly Val Pro Gly Val Gly
        450                 455                 460

Val Pro Gly Val Gly Val Pro Gly Val Gly Val Pro Gly Val Gly Val
465                 470                 475                 480

Pro Gly Val Gly Val Pro Gly Val Gly Val Pro Gly Val Gly Val Pro
            485                 490                 495

Gly Ala Gly Ala Gly Ser Gly Ala Gly Ala Gly Ser Gly Ala Gly Ala
        500                 505                 510

Gly Ser Gly Ala Gly Ala Gly Ser Gly Val Gly Val Pro Gly Val Gly
            515                 520                 525

Val Pro Gly Val Gly Val Pro Gly Val Gly Val Pro Gly Lys Gly Val
        530                 535                 540

Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
            565                 570                 575

Val Gly Val Pro Gly Val Gly Val Pro Gly Val Gly Val Pro Gly Val
        580                 585                 590

Gly Val Pro Gly Val Gly Val Pro Gly Ala Gly Ala Gly Ser Gly Ala
            595                 600                 605

Gly Ala Gly Ser Gly Ala Gly Ala Gly Ser Gly Ala Gly Ala Gly Ser
        610                 615                 620

Gly Val Gly Val Pro Gly Val Gly Val Pro Gly Val Gly Val Pro Gly
625                 630                 635                 640

Val Gly Val Pro Gly Lys Gly Val Pro Gly Val Gly Val Pro Gly Val
            645                 650                 655

Gly Val Pro Gly Val Gly Val Pro Gly Val Gly Val Pro Gly Val Gly
            660                 665                 670

Val Pro Gly Val Gly Val Pro Gly Val Gly Val Pro Gly Val Gly Val
        675                 680                 685

Pro Gly Val Gly Val Pro Gly Val Gly Val Pro Gly Val Gly Val Pro
            690                 695                 700

Gly Ala Gly Ala Gly Ser Gly Ala Gly Ala Gly Ser Gly Ala Gly Ala
705                 710                 715                 720

Gly Ser Gly Ala Gly Ala Gly Ser Gly Val Gly Val Pro Gly Val Gly
            725                 730                 735

Val Pro Gly Val Gly Val Pro Gly Val Gly Val Pro Gly Lys Gly Val
            740                 745                 750

Pro Gly Val Gly Val Pro Gly Val Gly Val Pro Gly Val Gly Val Pro
        755                 760                 765

Gly Val Gly Val Pro Gly Val Gly Val Pro Gly Val Gly Val Pro Gly
        770                 775                 780
```

```
Val Gly Val Pro Gly Val Gly Val Pro Gly Val Gly Val Pro Gly Val
785                 790                 795                 800

Gly Val Pro Gly Val Gly Val Pro Gly Ala Gly Ala Gly Ser Gly Ala
            805                 810                 815

Gly Ala Gly Ser
        820

<210> SEQ ID NO 20
<211> LENGTH: 1028
<212> TYPE: PRT
<213> ORGANISM: Artificial sequence
<220> FEATURE:
<223> OTHER INFORMATION: Synthetic construct

<400> SEQUENCE: 20

Gly Val Gly Val Pro Gly Val Gly Val Pro Gly Val Gly Val Pro Gly
1               5                   10                  15

Val Gly Val Pro Gly Lys Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ser Gly Ala Gly Ala
                85                  90                  95

Gly Ser Gly Ala Gly Ala Gly Ser Gly Val Gly Val Pro Gly Val Gly
            100                 105                 110

Val Pro Gly Val Gly Val Pro Gly Val Gly Val Pro Gly Lys Gly Val
        115                 120                 125

Pro Gly Val Gly Val Pro Gly Val Gly Val Pro Gly Val Gly Val Pro
130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

Gly Val Gly Val Pro Gly Val Gly Val Pro Gly Val Gly Val Pro Gly
    210                 215                 220

Val Gly Val Pro Gly Lys Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Ala Gly Ala Gly Ser Gly Ala Gly Ala Gly Ser Gly Ala Gly Ala
    290                 295                 300

Gly Ser Gly Ala Gly Ala Gly Ser Gly Val Gly Val Pro Gly Val Gly
305                 310                 315                 320
```

```
Val Pro Gly Val Gly Val Pro Gly Val Gly Val Pro Gly Lys Gly Val
                325                 330                 335

Pro Gly Val Gly Val Pro Gly Val Gly Val Pro Gly Val Gly Val Pro
            340                 345                 350

Gly Val Gly Val Pro Gly Val Gly Val Pro Gly Val Gly Val Pro Gly
        355                 360                 365

Val Gly Val Pro Gly Val Gly Val Pro Gly Val Gly Val Pro Gly Val
    370                 375                 380

Gly Val Pro Gly Val Gly Val Pro Gly Ala Gly Ala Gly Ser Gly Ala
385                 390                 395                 400

Gly Ala Gly Ser Gly Ala Gly Ala Gly Ser Gly Ala Gly Ala Gly Ser
            405                 410                 415

Gly Val Gly Val Pro Gly Val Gly Val Pro Gly Val Gly Val Pro Gly
        420                 425                 430

Val Gly Val Pro Gly Lys Gly Val Pro Gly Val Gly Val Pro Gly Val
    435                 440                 445

Gly Val Pro Gly Val Gly Val Pro Gly Val Gly Val Pro Gly Val Gly
            450                 455                 460

Val Pro Gly Val Gly Val Pro Gly Val Gly Val Pro Gly Val Gly Val
465                 470                 475                 480

Pro Gly Val Gly Val Pro Gly Val Gly Val Pro Gly Val Gly Val Pro
            485                 490                 495

Gly Ala Gly Ala Gly Ser Gly Ala Gly Ala Gly Ser Gly Ala Gly Ala
        500                 505                 510

Gly Ser Gly Ala Gly Ala Gly Ser Gly Val Gly Val Pro Gly Val Gly
    515                 520                 525

Val Pro Gly Val Gly Val Pro Gly Val Gly Val Pro Gly Lys Gly Val
    530                 535                 540

Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
            565                 570                 575

Val Gly Val Pro Gly Val Gly Val Pro Gly Val Gly Val Pro Gly Val
        580                 585                 590

Gly Val Pro Gly Val Gly Val Pro Gly Ala Gly Ala Gly Ser Gly Ala
    595                 600                 605

Gly Ala Gly Ser Gly Ala Gly Ala Gly Ser Gly Ala Gly Ala Gly Ser
        610                 615                 620

Gly Val Gly Val Pro Gly Val Gly Val Pro Gly Val Gly Val Pro Gly
625                 630                 635                 640

Val Gly Val Pro Gly Lys Gly Val Pro Gly Val Gly Val Pro Gly Val
                645                 650                 655

Gly Val Pro Gly Val Gly Val Pro Gly Val Gly Val Pro Gly Val Gly
            660                 665                 670

Val Pro Gly Val Gly Val Pro Gly Val Gly Val Pro Gly Val Gly Val
        675                 680                 685

Pro Gly Val Gly Val Pro Gly Val Gly Val Pro Gly Val Gly Val Pro
    690                 695                 700

Gly Ala Gly Ala Gly Ser Gly Ala Gly Ala Gly Ser Gly Ala Gly Ala
705                 710                 715                 720

Gly Ser Gly Ala Gly Ala Gly Ser Gly Val Gly Val Pro Gly Val Gly
            725                 730                 735

Val Pro Gly Val Gly Val Pro Gly Val Gly Val Pro Gly Lys Gly Val
```

```
                    740                 745                 750
Pro Gly Val Gly Val Pro Gly Val Gly Val Pro Gly Val Gly Val Pro
                755                 760                 765
Gly Val Gly Val Pro Gly Val Gly Val Pro Gly Val Gly Val Pro Gly
            770                 775                 780
Val Gly Val Pro Gly Val Gly Val Pro Gly Val Gly Val Pro Gly Val
785                 790                 795                 800
Gly Val Pro Gly Val Gly Val Pro Gly Ala Gly Ala Gly Ser Gly Ala
                805                 810                 815
Gly Ala Gly Ser Gly Ala Gly Ala Gly Ser Gly Ala Gly Ala Gly Ser
            820                 825                 830
Gly Val Gly Val Pro Gly Val Gly Val Pro Gly Val Gly Val Pro Gly
        835                 840                 845
Val Gly Val Pro Gly Lys Gly Val Pro Gly Val Gly Val Pro Gly Val
        850                 855                 860
Gly Val Pro Gly Val Gly Val Pro Gly Val Gly Val Pro Gly Val Gly
865                 870                 875                 880
Val Pro Gly Val Gly Val Pro Gly Val Gly Val Pro Gly Val Gly Val
                885                 890                 895
Pro Gly Val Gly Val Pro Gly Val Gly Val Pro Gly Val Gly Val Pro
                900                 905                 910
Gly Ala Gly Ala Gly Ser Gly Ala Gly Ala Gly Ser Gly Ala Gly Ala
            915                 920                 925
Gly Ser Gly Ala Gly Ala Gly Ser Val Gly Val Pro Gly Val Gly
        930                 935                 940
Val Pro Gly Val Gly Val Pro Gly Val Gly Val Pro Gly Lys Gly Val
945                 950                 955                 960
Pro Gly Val Gly Val Pro Gly Val Gly Val Pro Gly Val Gly Val Pro
                965                 970                 975
Gly Val Gly Val Pro Gly Val Gly Val Pro Gly Val Gly Val Pro Gly
            980                 985                 990
Val Gly Val Pro Gly Val Gly Val  Pro Gly Val Gly Val  Pro Gly Val
        995                 1000                1005
Gly Val  Pro Gly Val Gly Val  Pro Gly Ala Gly Ala  Gly Ser Gly
    1010                1015                1020
Ala Gly  Ala Gly Ser
    1025

<210> SEQ ID NO 21
<211> LENGTH: 768
<212> TYPE: PRT
<213> ORGANISM: Artificial sequence
<220> FEATURE:
<223> OTHER INFORMATION: Synthetic construct

<400> SEQUENCE: 21

Gly Ala Gly Ser Gly Ala Gly Ala Gly Ser Gly Ala Gly Ala Gly Ser
1               5                   10                  15
Gly Val Gly Val Pro Gly Val Gly Val Pro Gly Val Gly Val Pro Gly
            20                  25                  30
Val Gly Val Pro Gly Lys Gly Val Pro Gly Val Gly Val Pro Gly Val
        35                  40                  45
Gly Val Pro Gly Val Gly Val Pro Gly Val Gly Val Pro Gly Val Gly
    50                  55                  60
Val Pro Gly Val Gly Val Pro Gly Val Gly Val Pro Gly Val Gly Val
```

```
                65                  70                  75                  80
        Pro Gly Val Gly Val Pro Gly Val Gly Val Pro Gly Val Gly Val Pro
                            85                  90                  95
        Gly Ala Gly Ala Gly Ser Gly Ala Gly Ala Gly Ser Gly Ala Gly Ala
                           100                 105                 110
        Gly Ser Gly Ala Gly Ala Gly Ser Gly Ala Gly Ala Gly Ser Gly Ala
                    115                 120                 125
        Gly Ala Gly Ser Gly Ala Gly Ala Gly Ser Gly Ala Gly Ala Gly Ser
                    130                 135                 140
        Gly Val Gly Val Pro Gly Val Gly Val Pro Gly Val Gly Val Pro Gly
        145                 150                 155                 160
        Val Gly Val Pro Gly Lys Gly Val Pro Gly Val Gly Val Pro Gly Val
                    165                 170                 175
        Gly Val Pro Gly Val Gly Val Pro Gly Val Gly Val Pro Gly Val Gly
                    180                 185                 190
        Val Pro Gly Val Gly Val Pro Gly Val Gly Val Pro Gly Val Gly Val
                    195                 200                 205
        Pro Gly Val Gly Val Pro Gly Val Gly Val Pro Gly Val Gly Val Pro
        210                 215                 220
        Gly Ala Gly Ala Gly Ser Gly Ala Gly Ala Gly Ser Gly Ala Gly Ala
        225                 230                 235                 240
        Gly Ser Gly Ala Gly Ala Gly Ser Gly Ala Gly Ala Gly Ser Gly Ala
                    245                 250                 255
        Gly Ala Gly Ser Gly Ala Gly Ala Gly Ser Gly Ala Gly Ala Gly Ser
                    260                 265                 270
        Gly Val Gly Val Pro Gly Val Gly Val Pro Gly Val Gly Val Pro Gly
                    275                 280                 285
        Val Gly Val Pro Gly Lys Gly Val Pro Gly Val Gly Val Pro Gly Val
                    290                 295                 300
        Gly Val Pro Gly Val Gly Val Pro Gly Val Gly Val Pro Gly Val Gly
        305                 310                 315                 320
        Val Pro Gly Val Gly Val Pro Gly Val Gly Val Pro Gly Val Gly Val
                    325                 330                 335
        Pro Gly Val Gly Val Pro Gly Val Gly Val Pro Gly Val Gly Val Pro
                    340                 345                 350
        Gly Ala Gly Ala Gly Ser Gly Ala Gly Ala Gly Ser Gly Ala Gly Ala
                    355                 360                 365
        Gly Ser Gly Ala Gly Ala Gly Ser Gly Ala Gly Ala Gly Ser Gly Ala
                    370                 375                 380
        Gly Ala Gly Ser Gly Ala Gly Ala Gly Ser Gly Ala Gly Ala Gly Ser
        385                 390                 395                 400
        Gly Val Gly Val Pro Gly Val Gly Val Pro Gly Val Gly Val Pro Gly
                    405                 410                 415
        Val Gly Val Pro Gly Lys Gly Val Pro Gly Val Gly Val Pro Gly Val
                    420                 425                 430
        Gly Val Pro Gly Val Gly Val Pro Gly Val Gly Val Pro Gly Val Gly
                    435                 440                 445
        Val Pro Gly Val Gly Val Pro Gly Val Gly Val Pro Gly Val Gly Val
                    450                 455                 460
        Pro Gly Val Gly Val Pro Gly Val Gly Val Pro Gly Val Gly Val Pro
        465                 470                 475                 480
        Gly Ala Gly Ala Gly Ser Gly Ala Gly Ala Gly Ser Gly Ala Gly Ala
                    485                 490                 495
```

-continued

Gly Ser Gly Ala Gly Ala Gly Ser Gly Ala Gly Ala Gly Ser Gly Ala
                500                 505                 510

Gly Ala Gly Ser Gly Ala Gly Ala Gly Ser Gly Ala Gly Ala Gly Ser
            515                 520                 525

Gly Val Gly Val Pro Gly Val Gly Val Pro Gly Val Gly Val Pro Gly
        530                 535                 540

Val Gly Val Pro Gly Lys Gly Val Pro Gly Val Gly Val Pro Gly Val
545                 550                 555                 560

Gly Val Pro Gly Val Gly Val Pro Gly Val Gly Val Pro Gly Val Gly
                565                 570                 575

Val Pro Gly Val Gly Val Pro Gly Val Gly Val Pro Gly Val Gly Val
            580                 585                 590

Pro Gly Val Gly Val Pro Gly Val Gly Val Pro Gly Val Gly Val Pro
        595                 600                 605

Gly Ala Gly Ala Gly Ser Gly Ala Gly Ala Gly Ser Gly Ala Gly Ala
    610                 615                 620

Gly Ser Gly Ala Gly Ala Gly Ser Gly Ala Gly Ala Gly Ser Gly Ala
625                 630                 635                 640

Gly Ala Gly Ser Gly Ala Gly Ala Gly Ser Gly Ala Gly Ala Gly Ser
                645                 650                 655

Gly Val Gly Val Pro Gly Val Gly Val Pro Gly Val Gly Val Pro Gly
            660                 665                 670

Val Gly Val Pro Gly Lys Gly Val Pro Gly Val Gly Val Pro Gly Val
        675                 680                 685

Gly Val Pro Gly Val Gly Val Pro Gly Val Gly Val Pro Gly Val Gly
    690                 695                 700

Val Pro Gly Val Gly Val Pro Gly Val Gly Val Pro Gly Val Gly Val
705                 710                 715                 720

Pro Gly Val Gly Val Pro Gly Val Gly Val Pro Gly Val Gly Val Pro
                725                 730                 735

Gly Ala Gly Ala Gly Ser Gly Ala Gly Ala Gly Ser Gly Ala Gly Ala
            740                 745                 750

Gly Ser Gly Ala Gly Ala Gly Ser Gly Ala Gly Ala Gly Ser Gly Ala
        755                 760                 765

<210> SEQ ID NO 22
<211> LENGTH: 882
<212> TYPE: PRT
<213> ORGANISM: Artificial sequence
<220> FEATURE:
<223> OTHER INFORMATION: Synthetic construct

<400> SEQUENCE: 22

Gly Ala Gly Ala Gly Ser Gly Ala Gly Ala Gly Ser Gly Val Gly Val
1               5                   10                  15

Pro Leu Gly Pro Leu Gly Pro Gly Val Gly Val Pro Gly Val Gly Val
                20                  25                  30

Pro Gly Val Gly Val Pro Gly Lys Gly Val Pro Gly Val Gly Val Pro
            35                  40                  45

Gly Val Gly Val Pro Gly Val Gly Val Pro Gly Ala Gly Ala Gly Ser
        50                  55                  60

Gly Ala Gly Ala Gly Ser Gly Val Gly Val Pro Leu Gly Pro Leu Gly
65                  70                  75                  80

Pro Gly Val Gly Val Pro Gly Val Gly Val Pro Gly Val Gly Val Pro
                85                  90                  95

```
Gly Lys Gly Val Pro Gly Val Gly Val Pro Gly Val Gly Val Pro Gly
            100                 105                 110
Val Gly Val Pro Gly Ala Gly Ala Gly Ser Gly Ala Gly Ala Gly Ser
            115                 120                 125
Gly Val Gly Val Pro Leu Gly Pro Leu Gly Pro Gly Val Gly Val Pro
            130                 135                 140
Gly Val Gly Val Pro Gly Val Gly Val Pro Gly Lys Gly Val Pro Gly
145                 150                 155                 160
Val Gly Val Pro Gly Val Gly Val Pro Gly Val Gly Val Pro Gly Ala
            165                 170                 175
Gly Ala Gly Ser Gly Ala Gly Ala Gly Ser Gly Val Gly Val Pro Leu
            180                 185                 190
Gly Pro Leu Gly Pro Gly Val Gly Val Pro Gly Val Gly Val Pro Gly
            195                 200                 205
Val Gly Val Pro Gly Lys Gly Val Pro Gly Val Gly Val Pro Gly Val
            210                 215                 220
Gly Val Pro Gly Val Gly Val Pro Gly Ala Gly Ala Gly Ser Gly Ala
225                 230                 235                 240
Gly Ala Gly Ser Gly Val Gly Val Pro Leu Gly Pro Leu Gly Pro Gly
            245                 250                 255
Val Gly Val Pro Gly Val Gly Val Pro Gly Val Gly Val Pro Gly Lys
            260                 265                 270
Gly Val Pro Gly Val Gly Val Pro Gly Val Gly Val Pro Gly Val Gly
            275                 280                 285
Val Pro Gly Ala Gly Ala Gly Ser Gly Ala Gly Ala Gly Ser Gly Val
            290                 295                 300
Gly Val Pro Leu Gly Pro Leu Gly Pro Gly Val Gly Val Pro Gly Val
305                 310                 315                 320
Gly Val Pro Gly Val Gly Val Pro Gly Lys Gly Val Pro Gly Val Gly
            325                 330                 335
Val Pro Gly Val Gly Val Pro Gly Val Gly Val Pro Gly Ala Gly Ala
            340                 345                 350
Gly Ser Gly Ala Gly Ala Gly Ser Gly Val Gly Val Pro Leu Gly Pro
            355                 360                 365
Leu Gly Pro Gly Val Gly Val Pro Gly Val Gly Val Pro Gly Val Gly
            370                 375                 380
Val Pro Gly Lys Gly Val Pro Gly Val Gly Val Pro Gly Val Gly Val
385                 390                 395                 400
Pro Gly Val Gly Val Pro Gly Ala Gly Ala Gly Ser Gly Ala Gly Ala
            405                 410                 415
Gly Ser Gly Val Gly Val Pro Leu Gly Pro Leu Gly Pro Gly Val Gly
            420                 425                 430
Val Pro Gly Val Gly Val Pro Gly Val Gly Val Pro Gly Lys Gly Val
            435                 440                 445
Pro Gly Val Gly Val Pro Gly Val Gly Val Pro Gly Val Gly Val Pro
            450                 455                 460
Gly Ala Gly Ala Gly Ser Gly Ala Gly Ala Gly Ser Gly Val Gly Val
465                 470                 475                 480
Pro Leu Gly Pro Leu Gly Pro Gly Val Gly Val Pro Gly Val Gly Val
            485                 490                 495
Pro Gly Val Gly Val Pro Gly Lys Gly Val Pro Gly Val Gly Val Pro
            500                 505                 510
```

```
Gly Val Gly Val Pro Gly Val Gly Val Pro Gly Ala Gly Ala Gly Ser
            515                 520                 525
Gly Ala Gly Ala Gly Ser Gly Val Gly Val Pro Leu Gly Pro Leu Gly
        530                 535                 540
Pro Gly Val Gly Val Pro Gly Val Gly Val Pro Gly Val Gly Val Pro
545                 550                 555                 560
Gly Lys Gly Val Pro Gly Val Gly Val Pro Gly Val Gly Val Pro Gly
                565                 570                 575
Val Gly Val Pro Gly Ala Gly Ala Gly Ser Gly Ala Gly Ala Gly Ser
            580                 585                 590
Gly Val Gly Val Pro Leu Gly Pro Leu Gly Pro Gly Val Gly Val Pro
        595                 600                 605
Gly Val Gly Val Pro Gly Val Gly Val Pro Gly Lys Gly Val Pro Gly
    610                 615                 620
Val Gly Val Pro Gly Val Gly Val Pro Gly Val Gly Val Pro Gly Ala
625                 630                 635                 640
Gly Ala Gly Ser Gly Ala Gly Ala Gly Ser Gly Val Gly Val Pro Leu
                645                 650                 655
Gly Pro Leu Gly Pro Gly Val Gly Val Pro Gly Val Gly Val Pro Gly
            660                 665                 670
Val Gly Val Pro Gly Lys Gly Val Pro Gly Val Gly Val Pro Gly Val
        675                 680                 685
Gly Val Pro Gly Val Gly Val Pro Gly Ala Gly Ala Gly Ser Gly Ala
    690                 695                 700
Gly Ala Gly Ser Gly Val Gly Val Pro Leu Gly Pro Leu Gly Pro Gly
705                 710                 715                 720
Val Gly Val Pro Gly Val Gly Val Pro Gly Val Gly Val Pro Gly Lys
                725                 730                 735
Gly Val Pro Gly Val Gly Val Pro Gly Val Gly Val Pro Gly Val Gly
            740                 745                 750
Val Pro Gly Ala Gly Ala Gly Ser Gly Ala Gly Ala Gly Ser Gly Val
        755                 760                 765
Gly Val Pro Leu Gly Pro Leu Gly Pro Gly Val Gly Val Pro Gly Val
    770                 775                 780
Gly Val Pro Gly Val Gly Val Pro Gly Lys Gly Val Pro Gly Val Gly
785                 790                 795                 800
Val Pro Gly Val Gly Val Pro Gly Val Gly Val Pro Gly Ala Gly Ala
                805                 810                 815
Gly Ser Gly Ala Gly Ala Gly Ser Gly Val Gly Val Pro Leu Gly Pro
            820                 825                 830
Leu Gly Pro Gly Val Gly Val Pro Gly Val Gly Val Pro Gly Val Gly
        835                 840                 845
Val Pro Gly Lys Gly Val Pro Gly Val Gly Val Pro Gly Val Gly Val
    850                 855                 860
Pro Gly Val Gly Val Pro Gly Ala Gly Ala Gly Ser Gly Ala Gly Ala
865                 870                 875                 880

Gly Ser

<210> SEQ ID NO 23
<211> LENGTH: 912
<212> TYPE: PRT
<213> ORGANISM: Artificial sequence
<220> FEATURE:
<223> OTHER INFORMATION: Synthetic construct
```

```
<400> SEQUENCE: 23

Gly Ala Gly Ala Gly Ser Gly Ala Gly Ala Gly Ser Gly Val Gly Val
1               5                   10                  15

Pro Gly Phe Phe Val Arg Ala Arg Arg Gly Val Gly Val Pro Gly Val
            20                  25                  30

Gly Val Pro Gly Val Gly Val Pro Gly Lys Gly Val Pro Gly Val Gly
        35                  40                  45

Val Pro Gly Val Gly Val Pro Gly Val Gly Val Pro Gly Ala Gly Ala
    50                  55                  60

Gly Ser Gly Ala Gly Ala Gly Ser Gly Val Gly Val Pro Gly Phe Phe
65                  70                  75                  80

Val Arg Ala Arg Arg Gly Val Gly Val Pro Gly Val Gly Val Pro Gly
                85                  90                  95

Val Gly Val Pro Gly Lys Gly Val Pro Gly Val Gly Val Pro Gly Val
            100                 105                 110

Gly Val Pro Gly Val Gly Val Pro Gly Ala Gly Ala Gly Ser Gly Ala
            115                 120                 125

Gly Ala Gly Ser Gly Val Gly Val Pro Gly Phe Phe Val Arg Ala Arg
    130                 135                 140

Arg Gly Val Gly Val Pro Gly Val Gly Val Pro Gly Val Gly Val Pro
145                 150                 155                 160

Gly Lys Gly Val Pro Gly Val Gly Val Pro Gly Val Gly Val Pro Gly
                165                 170                 175

Val Gly Val Pro Gly Ala Gly Ala Gly Ser Gly Ala Gly Ala Gly Ser
            180                 185                 190

Gly Val Gly Val Pro Gly Phe Phe Val Arg Ala Arg Arg Gly Val Gly
        195                 200                 205

Val Pro Gly Val Gly Val Pro Gly Val Gly Val Pro Gly Lys Gly Val
    210                 215                 220

Pro Gly Val Gly Val Pro Gly Val Gly Val Pro Gly Val Gly Val Pro
225                 230                 235                 240

Gly Ala Gly Ala Gly Ser Gly Ala Gly Ala Gly Ser Gly Val Gly Val
                245                 250                 255

Pro Gly Phe Phe Val Arg Ala Arg Arg Gly Val Gly Val Pro Gly Val
            260                 265                 270

Gly Val Pro Gly Val Gly Val Pro Gly Lys Gly Val Pro Gly Val Gly
        275                 280                 285

Val Pro Gly Val Gly Val Pro Gly Val Gly Val Pro Gly Ala Gly Ala
    290                 295                 300

Gly Ser Gly Ala Gly Ala Gly Ser Gly Val Gly Val Pro Gly Phe Phe
305                 310                 315                 320

Val Arg Ala Arg Arg Gly Val Gly Val Pro Gly Val Gly Val Pro Gly
                325                 330                 335

Val Gly Val Pro Gly Lys Gly Val Pro Gly Val Gly Val Pro Gly Val
            340                 345                 350

Gly Val Pro Gly Val Gly Val Pro Gly Ala Gly Ala Gly Ser Gly Ala
            355                 360                 365

Gly Ala Gly Ser Gly Val Gly Val Pro Gly Phe Phe Val Arg Ala Arg
    370                 375                 380

Arg Gly Val Gly Val Pro Gly Val Gly Val Pro Gly Val Gly Val Pro
385                 390                 395                 400

Gly Lys Gly Val Pro Gly Val Gly Val Pro Gly Val Gly Val Pro Gly
                405                 410                 415
```

```
Val Gly Val Pro Gly Ala Gly Ala Gly Ser Gly Ala Gly Ala Gly Ser
            420                 425                 430

Gly Val Gly Val Pro Gly Phe Phe Val Arg Ala Arg Gly Val Gly
        435                 440                 445

Val Pro Gly Val Gly Val Pro Gly Val Gly Val Pro Gly Lys Gly Val
    450                 455                 460

Pro Gly Val Gly Val Pro Gly Val Gly Val Pro Gly Val Gly Val Pro
465                 470                 475                 480

Gly Ala Gly Ala Gly Ser Gly Ala Gly Ala Gly Ser Gly Val Gly Val
                485                 490                 495

Pro Gly Phe Phe Val Arg Ala Arg Gly Val Gly Val Pro Gly Val
        500                 505                 510

Gly Val Pro Gly Val Gly Val Pro Gly Lys Gly Val Pro Gly Val Gly
        515                 520                 525

Val Pro Gly Val Gly Val Pro Gly Val Gly Val Pro Gly Ala Gly Ala
    530                 535                 540

Gly Ser Gly Ala Gly Ala Gly Ser Gly Val Gly Val Pro Gly Phe Phe
545                 550                 555                 560

Val Arg Ala Arg Arg Gly Val Gly Val Pro Gly Val Gly Val Pro Gly
            565                 570                 575

Val Gly Val Pro Gly Lys Gly Val Pro Gly Val Gly Val Pro Gly Val
        580                 585                 590

Gly Val Pro Gly Val Gly Val Pro Gly Ala Gly Ala Gly Ser Gly Ala
        595                 600                 605

Gly Ala Gly Ser Gly Val Gly Val Pro Gly Phe Phe Val Arg Ala Arg
        610                 615                 620

Arg Gly Val Gly Val Pro Gly Val Gly Val Pro Gly Val Gly Val Pro
625                 630                 635                 640

Gly Lys Gly Val Pro Gly Val Gly Val Pro Gly Val Gly Val Pro Gly
            645                 650                 655

Val Gly Val Pro Gly Ala Gly Ala Gly Ser Gly Ala Gly Ala Gly Ser
            660                 665                 670

Gly Val Gly Val Pro Gly Phe Phe Val Arg Ala Arg Gly Val Gly
        675                 680                 685

Val Pro Gly Val Gly Val Pro Gly Val Gly Val Pro Gly Lys Gly Val
    690                 695                 700

Pro Gly Val Gly Val Pro Gly Val Gly Val Pro Gly Val Gly Val Pro
705                 710                 715                 720

Gly Ala Gly Ala Gly Ser Gly Ala Gly Ala Gly Ser Gly Val Gly Val
                725                 730                 735

Pro Gly Phe Phe Val Arg Ala Arg Arg Gly Val Gly Val Pro Gly Val
            740                 745                 750

Gly Val Pro Gly Val Gly Val Pro Gly Lys Gly Val Pro Gly Val Gly
        755                 760                 765

Val Pro Gly Val Gly Val Pro Gly Val Gly Val Pro Gly Ala Gly Ala
    770                 775                 780

Gly Ser Gly Ala Gly Ala Gly Ser Gly Val Gly Val Pro Gly Phe Phe
785                 790                 795                 800

Val Arg Ala Arg Arg Gly Val Gly Val Pro Gly Val Gly Val Pro Gly
            805                 810                 815

Val Gly Val Pro Gly Lys Gly Val Pro Gly Val Gly Val Pro Gly Val
        820                 825                 830
```

-continued

Gly Val Pro Gly Val Gly Val Pro Gly Ala Gly Ala Gly Ser Gly Ala
            835                 840                 845

Gly Ala Gly Ser Gly Val Gly Val Pro Gly Phe Phe Val Arg Ala Arg
    850                 855                 860

Arg Gly Val Gly Val Pro Gly Val Gly Val Pro Gly Val Gly Val Pro
865                 870                 875                 880

Gly Lys Gly Val Pro Gly Val Gly Val Pro Gly Val Gly Val Pro Gly
                885                 890                 895

Val Gly Val Pro Gly Ala Gly Ala Gly Ser Gly Ala Gly Ala Gly Ser
            900                 905                 910

<210> SEQ ID NO 24
<211> LENGTH: 820
<212> TYPE: PRT
<213> ORGANISM: Artificial sequence
<220> FEATURE:
<223> OTHER INFORMATION: Synthetic construct

<400> SEQUENCE: 24

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Val Gly Val Pro Gly Val Gly Val Pro Gly Val Gly Val Pro
    50                  55                  60

Gly Val Gly Val Pro Gly Lys Gly Val Pro Gly Val Gly Val Pro Gly
65                  70                  75                  80

Val Gly Val Pro Gly Val Gly Val Pro Gly Val Gly Val Pro Gly Val
            85                  90                  95

Gly Val Pro Gly Val Gly Val Pro Gly Val Gly Val Pro Gly Val Gly
                100                 105                 110

Val Pro Gly Val Gly Val Pro Gly Val Gly Val Pro Gly Val Gly Val
            115                 120                 125

Pro Gly Ala Gly Ala Gly Ser Gly Ala Gly Ala Gly Ser Gly Ala Gly
        130                 135                 140

Ala Gly Ser Gly Ala Gly Ala Gly Ser Gly Ala Gly Ala Gly Ser Gly
145                 150                 155                 160

Ala Gly Ala Gly Ser Gly Ala Gly Ala Gly Ser Gly Ala Gly Ala Gly
                165                 170                 175

Ser Gly Val Gly Val Pro Gly Val Gly Val Pro Gly Val Gly Val Pro
            180                 185                 190

Gly Val Gly Val Pro Gly Lys Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Val Gly Val
                245                 250                 255

Pro Gly Ala Gly Ala Gly Ser Gly Ala Gly Ala Gly Ser Gly Ala Gly
            260                 265                 270

Ala Gly Ser Gly Ala Gly Ala Gly Ser Gly Ala Gly Ala Gly Ser Gly
        275                 280                 285

```
Ala Gly Ala Gly Ser Gly Ala Gly Ala Gly Ser Gly Ala Gly Ala Gly
    290                 295                 300
Ser Gly Val Gly Val Pro Gly Val Gly Val Pro Gly Val Gly Val Pro
305                 310                 315                 320
Gly Val Gly Val Pro Gly Lys Gly Val Pro Gly Val Gly Val Pro Gly
                325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
        355                 360                 365
Val Pro Gly Val Gly Val Pro Gly Val Gly Val Pro Gly Val Gly Val
370                 375                 380
Pro Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
                405                 410                 415
Ala Gly Ala Gly Ser Gly Ala Gly Ala Gly Ser Gly Ala Gly Ala Gly
            420                 425                 430
Ser Gly Val Gly Val Pro Gly Val Gly Val Pro Gly Val Gly Val Pro
        435                 440                 445
Gly Val Gly Val Pro Gly Lys Gly Val Pro Gly Val Gly Val Pro Gly
    450                 455                 460
Val Gly Val Pro Gly Val Gly Val Pro Gly Val Gly Val Pro Gly Val
465                 470                 475                 480
Gly Val Pro Gly Val Gly Val Pro Gly Val Gly Val Pro Gly Val Gly
                485                 490                 495
Val Pro Gly Val Gly Val Pro Gly Val Gly Val Pro Gly Val Gly Val
            500                 505                 510
Pro Gly Ala Gly Ala Gly Ser Gly Ala Gly Ala Gly Ser Gly Ala Gly
        515                 520                 525
Ala Gly Ser Gly Ala Gly Ala Gly Ser Gly Ala Gly Ala Gly Ser Gly
    530                 535                 540
Ala Gly Ala Gly Ser Gly Ala Gly Ala Gly Ser Gly Ala Gly Ala Gly
545                 550                 555                 560
Ser Gly Val Gly Val Pro Gly Val Gly Val Pro Gly Val Gly Val Pro
                565                 570                 575
Gly Val Gly Val Pro Gly Lys Gly Val Pro Gly Val Gly Val Pro Gly
            580                 585                 590
Val Gly Val Pro Gly Val Gly Val Pro Gly Val Gly Val Pro Gly Val
        595                 600                 605
Gly Val Pro Gly Val Gly Val Pro Gly Val Gly Val Pro Gly Val Gly
    610                 615                 620
Val Pro Gly Val Gly Val Pro Gly Val Gly Val Pro Gly Val Gly Val
625                 630                 635                 640
Pro Gly Ala Gly Ala Gly Ser Gly Ala Gly Ala Gly Ser Gly Ala Gly
                645                 650                 655
Ala Gly Ser Gly Ala Gly Ala Gly Ser Gly Ala Gly Ala Gly Ser Gly
            660                 665                 670
Ala Gly Ala Gly Ser Gly Ala Gly Ala Gly Ser Gly Ala Gly Ala Gly
        675                 680                 685
Ser Gly Val Gly Val Pro Gly Val Gly Val Pro Gly Val Gly Val Pro
    690                 695                 700
Gly Val Gly Val Pro Gly Lys Gly Val Pro Gly Val Gly Val Pro Gly
```

```
                705                 710                 715                 720
Val Gly Val Pro Gly Val Gly Val Pro Gly Val Gly Val Pro Gly Val
                    725                 730                 735

Gly Val Pro Gly Val Gly Val Pro Gly Val Gly Val Pro Gly Val Gly
                740                 745                 750

Val Pro Gly Val Gly Val Pro Gly Val Gly Val Pro Gly Val Gly Val
            755                 760                 765

Pro Gly Ala Gly Ala Gly Ser Gly Ala Gly Ala Gly Ser Gly Ala Gly
        770                 775                 780

Ala Gly Ser Gly Ala Gly Ala Gly Ser Gly Ala Gly Ala Gly Ser Gly
785                 790                 795                 800

Ala Gly Ala Met Asp Pro Gly Arg Tyr Gln Asp Leu Arg Ser His His
                805                 810                 815

His His His His
        820

<210> SEQ ID NO 25
<211> LENGTH: 877
<212> TYPE: PRT
<213> ORGANISM: Artificial sequence
<220> FEATURE:
<223> OTHER INFORMATION: Synthetic construct

<400> SEQUENCE: 25

Met Asp Pro Val Val Leu Gln Arg Arg Asp Trp Glu Asn Pro Gly Val
1               5                   10                  15

Thr Gln Leu Val Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
                85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
        195                 200                 205

Gly Val Pro Gly Ala Gly Ala Gly Ser Gly Ala Gly Ala Gly Ser Gly
    210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
```

245                 250                 255
Lys Gly Val Pro Gly Val Gly Val Pro Gly Val Gly Val Pro Gly Val
            260                 265                 270
Gly Val Pro Gly Ala Gly Ala Gly Ser Gly Ala Gly Ala Gly Ser Gly
            275                 280                 285
Ala Gly Ala Gly Ser Gly Ala Gly Ala Gly Ser Gly Val Gly Val Pro
            290                 295                 300
Gly Val Gly Val Pro Gly Val Gly Val Pro Gly Val Gly Val Pro Gly
305                 310                 315                 320
Lys Gly Val Pro Gly Val Gly Val Pro Gly Val Gly Val Pro Gly Val
            325                 330                 335
Gly Val Pro Gly Ala Gly Ala Gly Ser Gly Ala Gly Ala Gly Ser Gly
            340                 345                 350
Ala Gly Ala Gly Ser Gly Ala Gly Ala Gly Ser Gly Val Gly Val Pro
            355                 360                 365
Gly Val Gly Val Pro Gly Val Gly Val Pro Gly Val Gly Val Pro Gly
            370                 375                 380
Lys Gly Val Pro Gly Val Gly Val Pro Gly Val Gly Val Pro Gly Val
385                 390                 395                 400
Gly Val Pro Gly Ala Gly Ala Gly Ser Gly Ala Gly Ala Gly Ser Gly
            405                 410                 415
Ala Gly Ala Gly Ser Gly Ala Gly Ala Gly Ser Gly Val Gly Val Pro
            420                 425                 430
Gly Val Gly Val Pro Gly Val Gly Val Pro Gly Val Gly Val Pro Gly
            435                 440                 445
Lys Gly Val Pro Gly Val Gly Val Pro Gly Val Gly Val Pro Gly Val
            450                 455                 460
Gly Val Pro Gly Ala Gly Ala Gly Ser Gly Ala Gly Ala Gly Ser Gly
465                 470                 475                 480
Ala Gly Ala Gly Ser Gly Ala Gly Ala Gly Ser Gly Val Gly Val Pro
            485                 490                 495
Gly Val Gly Val Pro Gly Val Gly Val Pro Gly Val Gly Val Pro Gly
            500                 505                 510
Lys Gly Val Pro Gly Val Gly Val Pro Gly Val Gly Val Pro Gly Val
            515                 520                 525
Gly Val Pro Gly Ala Gly Ala Gly Ser Gly Ala Gly Ala Gly Ser Gly
            530                 535                 540
Ala Gly Ala Gly Ser Gly Ala Gly Ala Gly Ser Gly Val Gly Val Pro
545                 550                 555                 560
Gly Val Gly Val Pro Gly Val Gly Val Pro Gly Val Gly Val Pro Gly
            565                 570                 575
Lys Gly Val Pro Gly Val Gly Val Pro Gly Val Gly Val Pro Gly Val
            580                 585                 590
Gly Val Pro Gly Ala Gly Ala Gly Ser Gly Ala Gly Ala Gly Ser Gly
            595                 600                 605
Ala Gly Ala Gly Ser Gly Ala Gly Ala Gly Ser Gly Val Gly Val Pro
            610                 615                 620
Gly Val Gly Val Pro Gly Val Gly Val Pro Gly Val Gly Val Pro Gly
625                 630                 635                 640
Lys Gly Val Pro Gly Val Gly Val Pro Gly Val Gly Val Pro Gly Val
            645                 650                 655
Gly Val Pro Gly Ala Gly Ala Gly Ser Gly Ala Gly Ala Gly Ser Gly
            660                 665                 670

```
Ala Gly Ala Gly Ser Gly Ala Gly Ala Gly Ser Gly Val Gly Val Pro
        675                 680                 685
Gly Val Gly Val Pro Gly Val Gly Val Pro Gly Val Gly Val Pro Gly
    690                 695                 700
Lys Gly Val Pro Gly Val Gly Val Pro Gly Val Gly Val Pro Gly Val
705                 710                 715                 720
Gly Val Pro Gly Ala Gly Ala Gly Ser Gly Ala Gly Ala Gly Ser Gly
                725                 730                 735
Ala Gly Ala Gly Ser Gly Ala Gly Ala Gly Ser Gly Val Gly Val Pro
        740                 745                 750
Gly Val Gly Val Pro Gly Val Gly Val Pro Gly Val Gly Val Pro Gly
    755                 760                 765
Lys Gly Val Pro Gly Val Gly Val Pro Gly Val Gly Val Pro Gly Val
770                 775                 780
Gly Val Pro Gly Ala Gly Ala Gly Ser Gly Ala Gly Ala Gly Ser Gly
785                 790                 795                 800
Ala Gly Ala Gly Ser Gly Ala Gly Ala Gly Ser Gly Val Gly Val Pro
        805                 810                 815
Gly Val Gly Val Pro Gly Val Gly Val Pro Gly Val Gly Val Pro Gly
    820                 825                 830
Lys Gly Val Pro Gly Val Gly Val Pro Gly Val Gly Val Pro Gly Ala
        835                 840                 845
Gly Ala Gly Ser Gly Ala Gly Ala Gly Ser Gly Ala Met Asp Pro Gly
    850                 855                 860
Arg Tyr Gln Asp Leu Arg Ser His His His His His
865                 870                 875

<210> SEQ ID NO 26
<211> LENGTH: 8
<212> TYPE: PRT
<213> ORGANISM: Artificial sequence
<220> FEATURE:
<223> OTHER INFORMATION: Synthetic construct

<400> SEQUENCE: 26

Ala Pro Gly Gln Ile Ala Gly Gln
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic construct

<400> SEQUENCE: 27

Gly Pro Gln Gly Leu Ala Gly Gln
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic construct

<400> SEQUENCE: 28

Gly Pro Leu Gly Ile Ala Gly Ile
1               5
```

<210> SEQ ID NO 29
<211> LENGTH: 8
<212> TYPE: PRT
<213> ORGANISM: Artificial sequence
<220> FEATURE:
<223> OTHER INFORMATION: Synthetic construct

<400> SEQUENCE: 29

Ile Pro Glu Asn Phe Phe Gly Val
1               5

<210> SEQ ID NO 30
<211> LENGTH: 8
<212> TYPE: PRT
<213> ORGANISM: Artificial sequence
<220> FEATURE:
<223> OTHER INFORMATION: Synthetic construct

<400> SEQUENCE: 30

Met Ala Ala Ser Ala Lys Arg Glu
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic construct

<400> SEQUENCE: 31

Pro Phe Ser Pro Leu Val Ala Thr
1               5

<210> SEQ ID NO 32
<211> LENGTH: 8
<212> TYPE: PRT
<213> ORGANISM: Artificial sequence
<220> FEATURE:
<223> OTHER INFORMATION: Synthetic construct

<400> SEQUENCE: 32

Gly Pro Gln Gly Ile Phe Gly Gln
1               5

<210> SEQ ID NO 33
<211> LENGTH: 8
<212> TYPE: PRT
<213> ORGANISM: Artificial sequence
<220> FEATURE:
<223> OTHER INFORMATION: Synthetic construct

<400> SEQUENCE: 33

Arg Ala Ile His Ile Gln Ala Glu
1               5

<210> SEQ ID NO 34
<211> LENGTH: 8
<212> TYPE: PRT
<213> ORGANISM: Artificial sequence
<220> FEATURE:
<223> OTHER INFORMATION: Synthetic construct

<400> SEQUENCE: 34

Gly Pro Leu Gly Ile Ala Gly Gln
1               5

```
<210> SEQ ID NO 35
<211> LENGTH: 8
<212> TYPE: PRT
<213> ORGANISM: Artificial sequence
<220> FEATURE:
<223> OTHER INFORMATION: Synthetic construct

<400> SEQUENCE: 35

Gly Pro Gln Ala Ile Ala Gly Gln
1               5

<210> SEQ ID NO 36
<211> LENGTH: 810
<212> TYPE: PRT
<213> ORGANISM: Artificial sequence
<220> FEATURE:
<223> OTHER INFORMATION: Synthetic construct

<400> SEQUENCE: 36

Gly Ala Gly Ser Gly Ala Gly Ala Gly Ser Gly Ala Gly Ala Gly Ser
1               5                   10                  15

Gly Val Gly Val Pro Gly Val Gly Val Pro Gly Val Gly Val Pro Gly
            20                  25                  30

Val Gly Gly Pro Gln Gly Ile Phe Gly Gln Pro Gly Lys Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
            85                  90                  95

Val Pro Gly Val Gly Val Pro Gly Ala Gly Ala Gly Ser Gly Ala Gly
            100                 105                 110

Ala Gly Ser Gly Ala Gly Ala Gly Ser Gly Ala Gly Ala Gly Ser Gly
        115                 120                 125

Ala Gly Ala Gly Ser Gly Ala Gly Ala Gly Ser Gly Ala Gly Ala Gly
        130                 135                 140

Ser Gly Ala Gly Ala Gly Ser Gly Val Gly Val Pro Gly Val Gly Val
145                 150                 155                 160

Pro Gly Val Gly Val Pro Gly Val Gly Gly Pro Gln Gly Ile Phe Gly
            165                 170                 175

Gln Pro Gly Lys Gly Val Pro Gly Val Gly Val Pro Gly Val Gly Val
        180                 185                 190

Pro Gly Val Gly Val Pro Gly Val Gly Val Pro Gly Val Gly Val Pro
    195                 200                 205

Gly Val Gly Val Pro Gly Val Gly Val Pro Gly Val Gly Val Pro Gly
    210                 215                 220

Val Gly Val Pro Gly Val Gly Val Pro Gly Val Gly Val Pro Gly Ala
225                 230                 235                 240

Gly Ala Gly Ser Gly Ala Gly Ala Gly Ser Gly Ala Gly Ala Gly Ser
            245                 250                 255

Gly Ala Gly Ala Gly Ser Gly Ala Gly Ala Gly Ser Gly Ala Gly Ala
        260                 265                 270

Gly Ser Gly Ala Gly Ala Gly Ser Gly Ala Gly Ala Gly Ser Gly Val
        275                 280                 285

Gly Val Pro Gly Val Gly Val Pro Gly Val Gly Val Pro Gly Val Gly
    290                 295                 300
```

```
Gly Pro Gln Gly Ile Phe Gly Gln Pro Gly Lys Gly Val Pro Gly Val
305                 310                 315                 320

Gly Val Pro Gly Val Gly Val Pro Gly Val Gly Val Pro Gly Val Gly
                325                 330                 335

Val Pro Gly Val Gly Val Pro Gly Val Gly Val Pro Gly Val Gly Val
            340                 345                 350

Pro Gly Val Gly Val Pro Gly Val Gly Val Pro Gly Val Gly Val Pro
        355                 360                 365

Gly Val Gly Val Pro Gly Ala Gly Ala Gly Ser Gly Ala Gly Ala Gly
    370                 375                 380

Ser Gly Ala Gly Ala Gly Ser Gly Ala Gly Ala Gly Ser Gly Ala Gly
385                 390                 395                 400

Ala Gly Ser Gly Ala Gly Ala Gly Ser Gly Ala Gly Ala Gly Ser Gly
                405                 410                 415

Ala Gly Ala Gly Ser Gly Val Gly Val Pro Gly Val Gly Val Pro Gly
            420                 425                 430

Val Gly Val Pro Gly Val Gly Gly Pro Gln Gly Ile Phe Gly Gln Pro
        435                 440                 445

Gly Lys Gly Val Pro Gly Val Gly Val Pro Gly Val Gly Val Pro Gly
    450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
                485                 490                 495

Val Pro Gly Val Gly Val Pro Gly Val Gly Val Pro Gly Ala Gly Ala
            500                 505                 510

Gly Ser Gly Ala Gly Ala Gly Ser Gly Ala Gly Ala Gly Ser Gly Ala
        515                 520                 525

Gly Ala Gly Ser Gly Ala Gly Ala Gly Ser Gly Ala Gly Ala Gly Ser
    530                 535                 540

Gly Ala Gly Ala Gly Ser Gly Ala Gly Ala Gly Ser Gly Val Gly Val
545                 550                 555                 560

Pro Gly Val Gly Val Pro Gly Val Gly Val Pro Gly Val Gly Gly Pro
                565                 570                 575

Gln Gly Ile Phe Gly Gln Pro Gly Lys Gly Val Pro Gly Val Gly Val
            580                 585                 590

Pro Gly Val Gly Val Pro Gly Val Gly Val Pro Gly Val Gly Val Pro
        595                 600                 605

Gly Val Gly Val Pro Gly Val Gly Val Pro Gly Val Gly Val Pro Gly
    610                 615                 620

Val Gly Val Pro Gly Val Gly Val Pro Gly Val Gly Val Pro Gly Val
625                 630                 635                 640

Gly Val Pro Gly Ala Gly Ala Gly Ser Gly Ala Gly Ala Gly Ser Gly
                645                 650                 655

Ala Gly Ala Gly Ser Gly Ala Gly Ala Gly Ser Gly Ala Gly Ala Gly
            660                 665                 670

Ser Gly Ala Gly Ala Gly Ser Gly Ala Gly Ala Gly Ser Gly Ala Gly
        675                 680                 685

Ala Gly Ser Gly Val Gly Val Pro Gly Val Gly Val Pro Gly Val Gly
    690                 695                 700

Val Pro Gly Val Gly Gly Pro Gln Gly Ile Phe Gly Gln Pro Gly Lys
705                 710                 715                 720

Gly Val Pro Gly Val Gly Val Pro Gly Val Gly Val Pro Gly Val Gly
```

-continued

```
                725                 730                 735
Val Pro Gly Val Gly Val Pro Gly Val Gly Val Pro Gly Val Gly Val
            740                 745                 750

Pro Gly Val Gly Val Pro Gly Val Gly Val Pro Gly Val Gly Val Pro
            755                 760                 765

Gly Val Gly Val Pro Gly Val Gly Val Pro Gly Ala Gly Ala Gly Ser
        770                 775             780

Gly Ala Gly Ala Gly Ser Gly Ala Gly Ala Gly Ser Gly Ala Gly Ala
785                 790                 795                 800

Gly Ser Gly Ala Gly Ala Gly Ser Gly Ala
                805                 810
```